(12) United States Patent
Yasuda

(10) Patent No.: US 8,052,025 B2
(45) Date of Patent: Nov. 8, 2011

(54) HOLLOW TISSUE INOSCULATION APPARATUS

(75) Inventor: Mamoru Yasuda, Hino (JP)

(73) Assignee: Olympus Corporation, Tokyo (JP)

(*) Notice: Subject to any disclaimer, the term of this patent is extended or adjusted under 35 U.S.C. 154(b) by 257 days.

(21) Appl. No.: 12/542,950

(22) Filed: Aug. 18, 2009

(65) Prior Publication Data

US 2010/0038402 A1 Feb. 18, 2010

(30) Foreign Application Priority Data

Aug. 18, 2008 (JP) ................................. 2008-210028

(51) Int. Cl.
*A61B 17/068* (2006.01)

(52) U.S. Cl. .................... 227/176.1; 227/19; 227/175.1; 606/139; 606/219

(58) Field of Classification Search ............... 227/19, 227/175.1, 176.1, 175.2, 180.1; 606/139, 606/151, 153, 219
See application file for complete search history.

(56) References Cited

U.S. PATENT DOCUMENTS

| | | | |
|---|---|---|---|
| 4,319,576 A | 3/1982 | Rothfuss | |
| 5,007,921 A | 4/1991 | Brown | |
| 5,242,457 A | 9/1993 | Akopov et al. | |
| 5,395,030 A | 3/1995 | Kuramoto et al. | |
| 5,573,543 A | 11/1996 | Akopov et al. | |
| 5,658,300 A * | 8/1997 | Bito et al. .................... | 606/143 |
| 5,695,504 A | 12/1997 | Gifford, III et al. | |
| 5,749,895 A | 5/1998 | Sawyer et al. | |
| 5,891,160 A * | 4/1999 | Williamson et al. ........... | 606/144 |
| 5,893,856 A | 4/1999 | Jacob et al. | |
| 6,183,486 B1 | 2/2001 | Snow et al. | |
| 6,248,117 B1 | 6/2001 | Blatter | |
| 6,348,064 B1 | 2/2002 | Kanner | |
| 6,652,543 B2 | 11/2003 | Spence et al. | |
| 6,874,669 B2 * | 4/2005 | Adams et al. ................ | 227/175.1 |
| 6,890,338 B1 | 5/2005 | Davis et al. | |
| 7,032,798 B2 * | 4/2006 | Whitman et al. ............ | 227/175.1 |
| 7,300,444 B1 | 11/2007 | Nielsen et al. | |
| 7,472,815 B2 * | 1/2009 | Shelton et al. ............... | 227/176.1 |
| 7,559,450 B2 * | 7/2009 | Wales et al. .................. | 227/175.1 |
| 7,699,859 B2 | 4/2010 | Bombard et al. | |
| 7,713,284 B2 | 5/2010 | Crofford | |
| 2003/0014064 A1 | 1/2003 | Blatter | |
| 2004/0002721 A1 | 1/2004 | Podmore et al. | |
| 2004/0097992 A1 | 5/2004 | Spence et al. | |
| 2005/0080437 A1 | 4/2005 | Wright | |

(Continued)

FOREIGN PATENT DOCUMENTS

JP A H6-47050 2/1994

(Continued)

*Primary Examiner* — Scott A. Smith
(74) *Attorney, Agent, or Firm* — Scully, Scott, Murphy & Presser, P.C.

(57) ABSTRACT

A hollow tissue inosculation apparatus is to inosculate two hollow tissues to each other with a staple having a plurality of elastically deformable bent staple pins. The hollow tissue inosculation apparatus includes a staple holder to hold the staple, a curvature control mechanism to control curvature of the staple pins of the staple held in the staple holder, and a gap control mechanism to control gaps of the hollow tissues with respect to the staple holder. The curvature control mechanism substantially straightens the staple pins. The gap control mechanism reduces the gaps to cause the substantially straightened staple pins to penetrate through the hollow tissues. The hollow tissue inosculation apparatus also includes a detector to detect the staple pins of the staple that have penetrated through the hollow tissue.

4 Claims, 46 Drawing Sheets

U.S. PATENT DOCUMENTS

| | | |
|---|---|---|
| 2006/0069401 A1 | 3/2006 | Wright |
| 2007/0093869 A1 | 4/2007 | Bloom et al. |
| 2007/0119902 A1 | 5/2007 | Vargas et al. |
| 2009/0188964 A1 | 7/2009 | Orlov |
| 2010/0038402 A1 | 2/2010 | Yasuda |
| 2010/0072249 A1 | 3/2010 | Yasuda |
| 2010/0072250 A1 | 3/2010 | Yasuda |
| 2010/0076466 A1 | 3/2010 | Yasuda |
| 2010/0076468 A1 | 3/2010 | Yasuda |
| 2010/0076469 A1 | 3/2010 | Yasuda |
| 2010/0181363 A1 | 7/2010 | Yasuda |

FOREIGN PATENT DOCUMENTS

| | | |
|---|---|---|
| JP | A 2001-190557 | 7/2001 |

\* cited by examiner

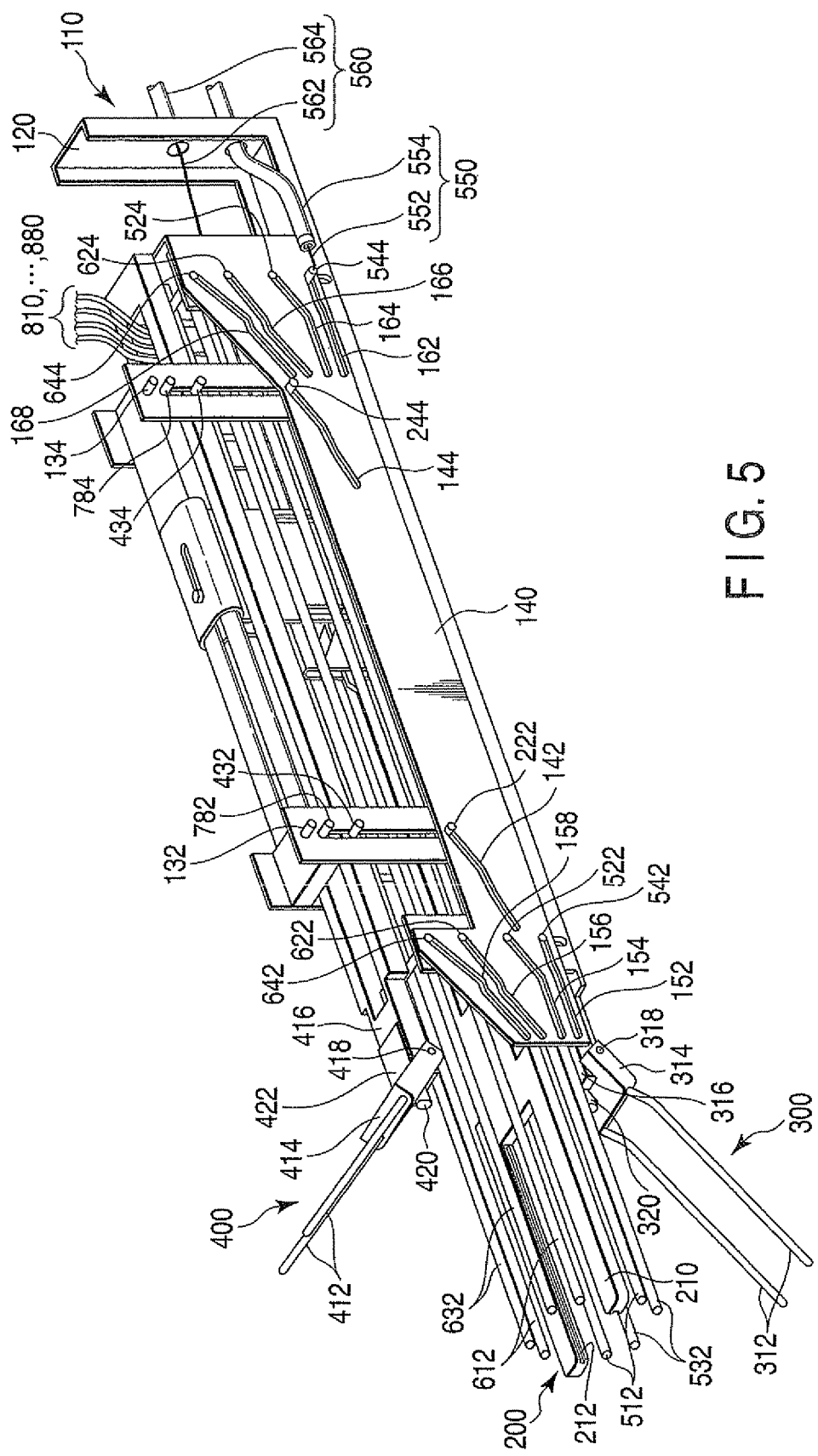
F I G. 5

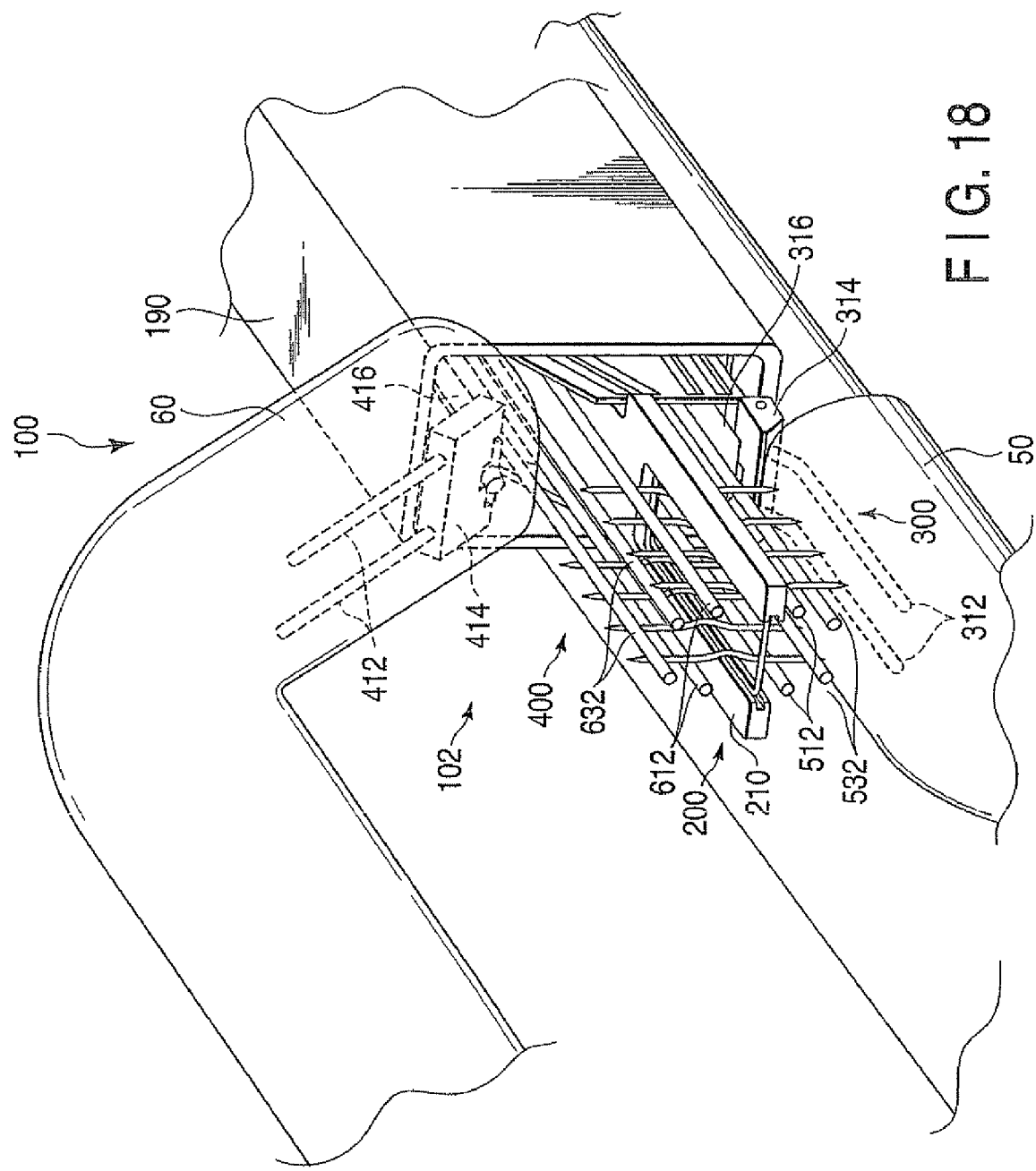
F I G. 18

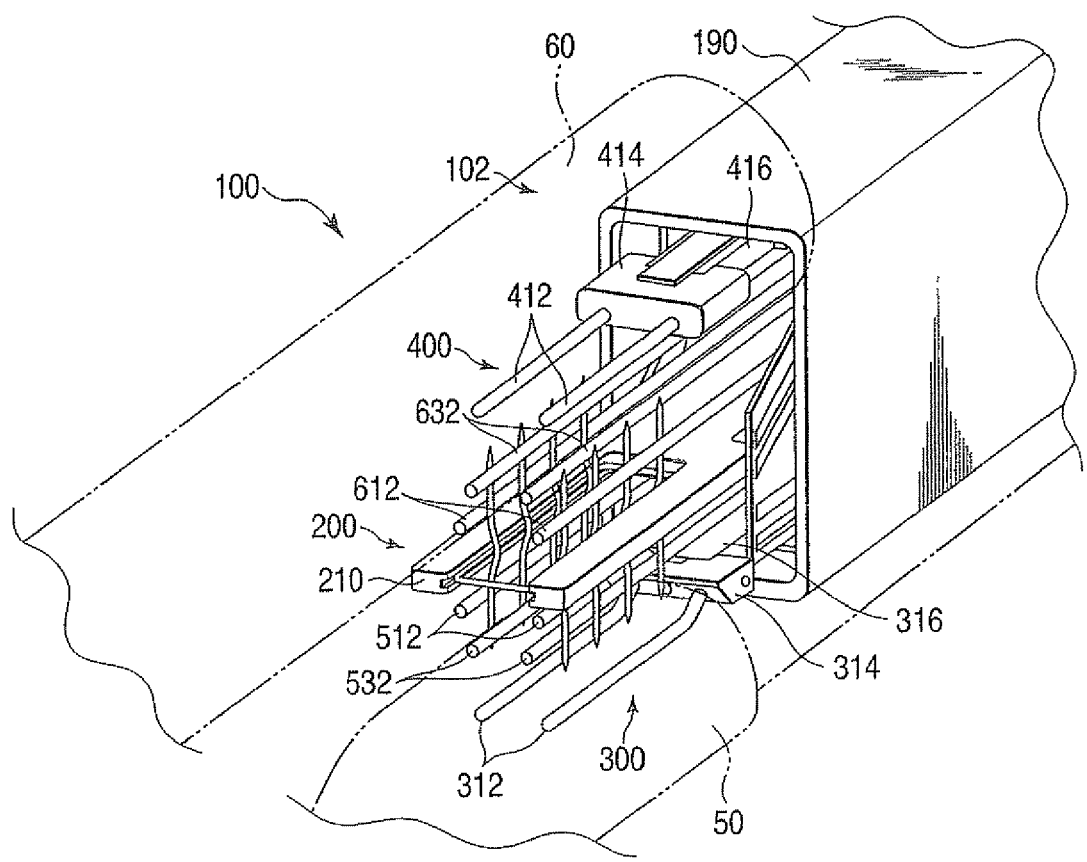
F I G. 20
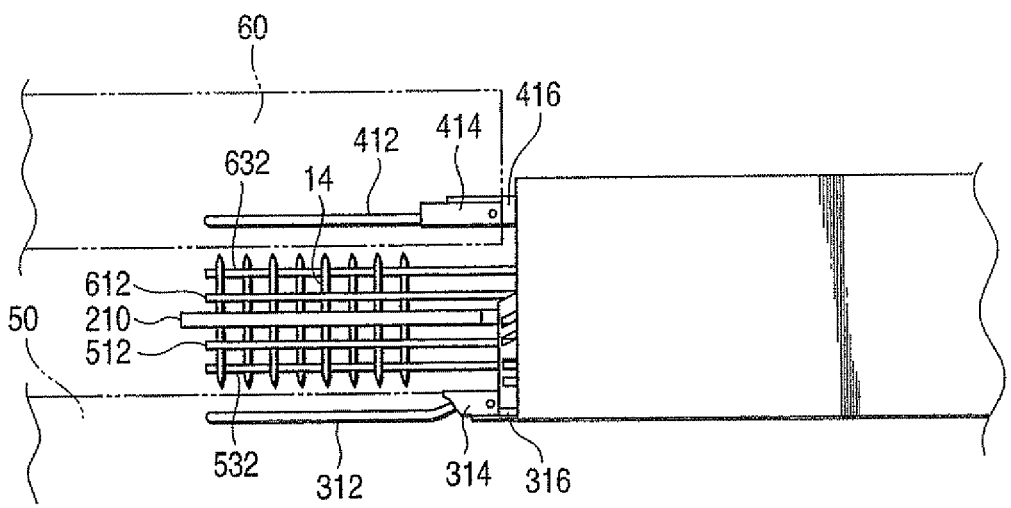
F I G. 21

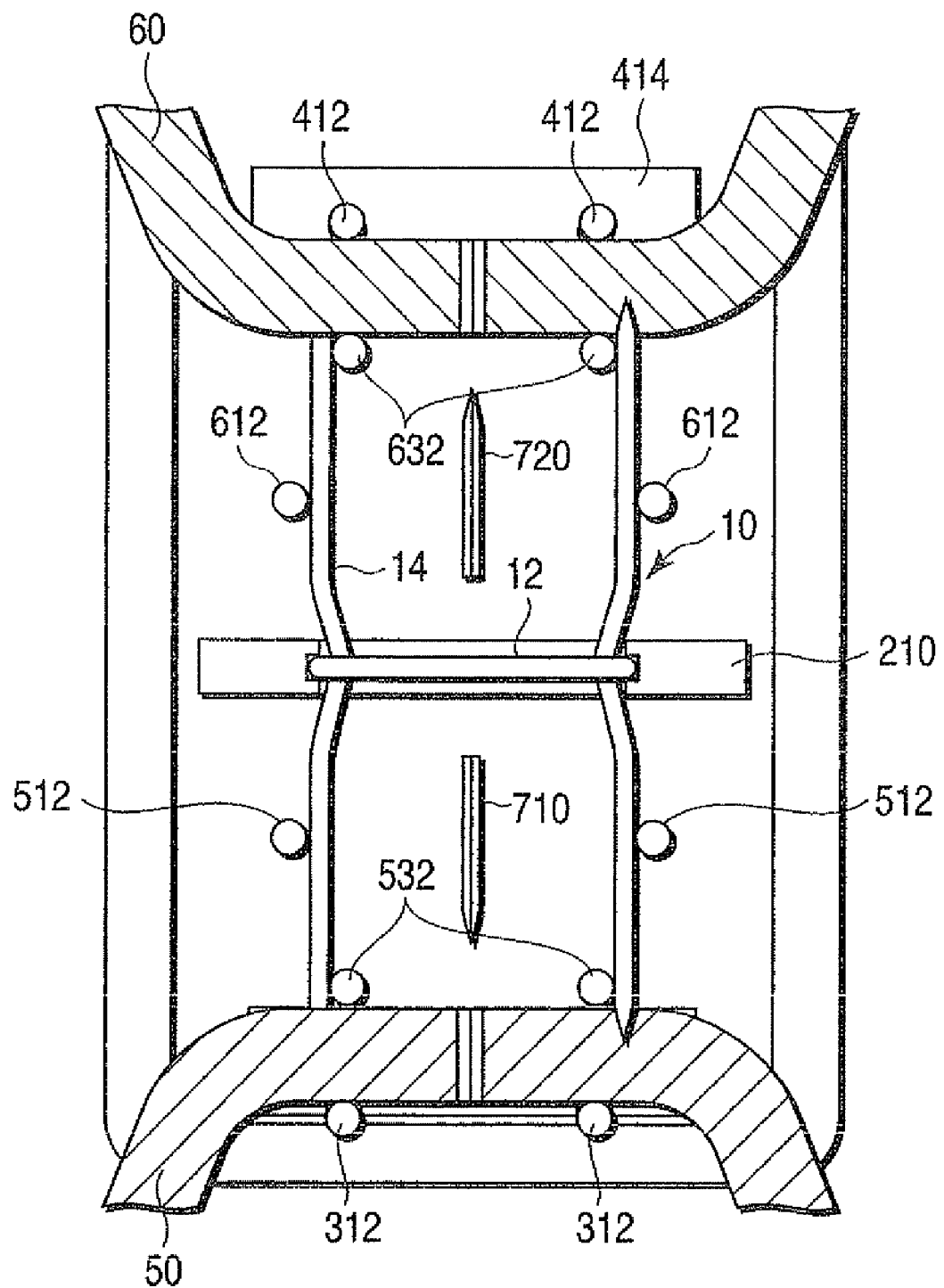
F I G. 34

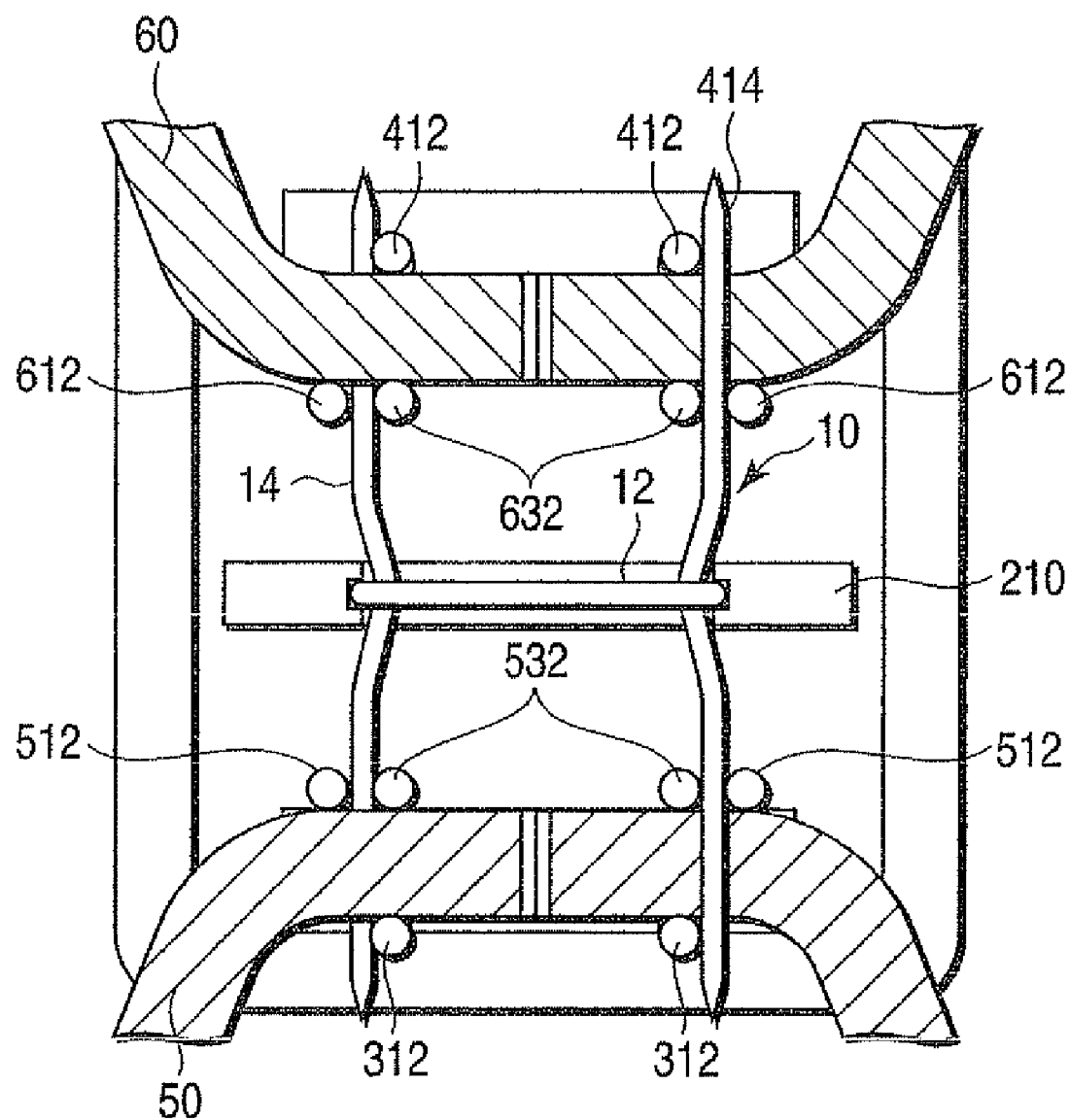
F I G. 40

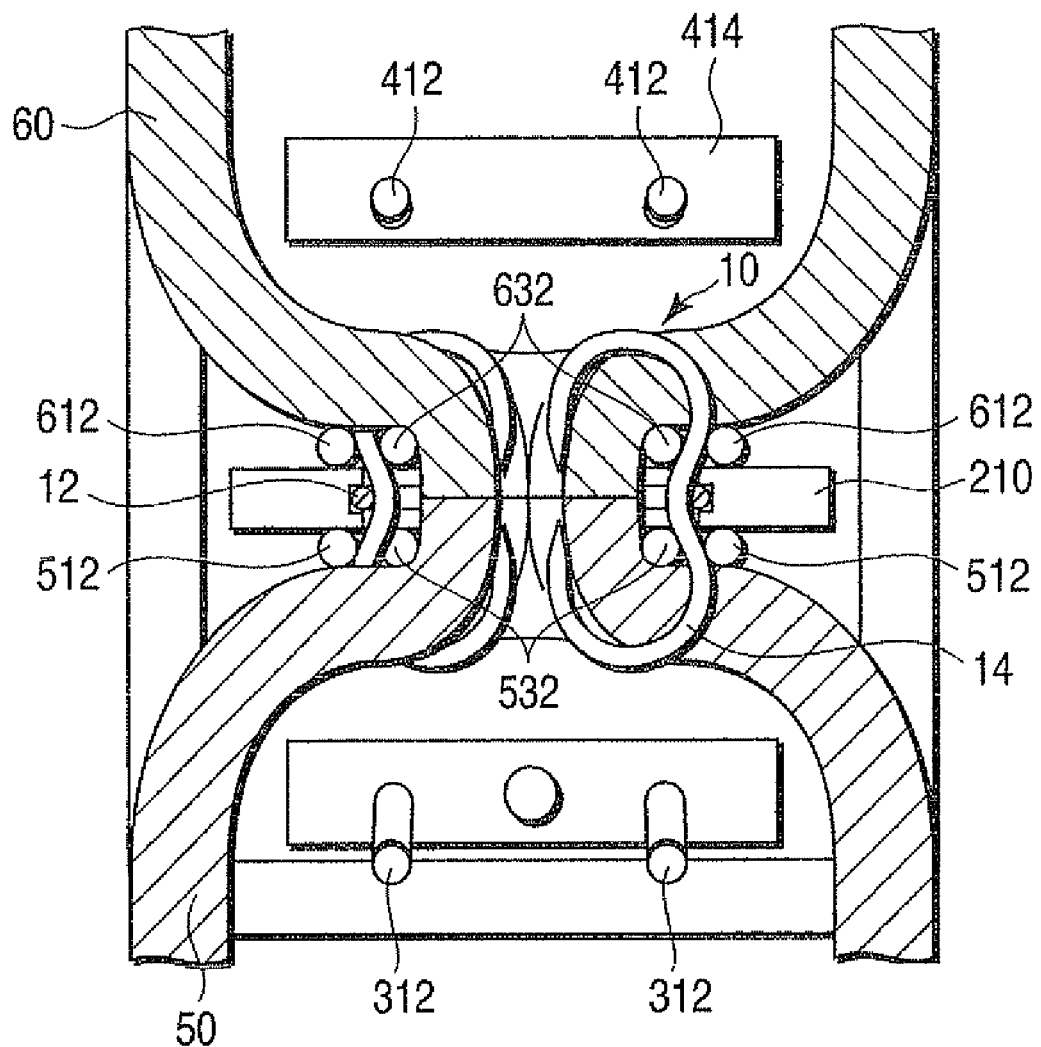
F I G. 46

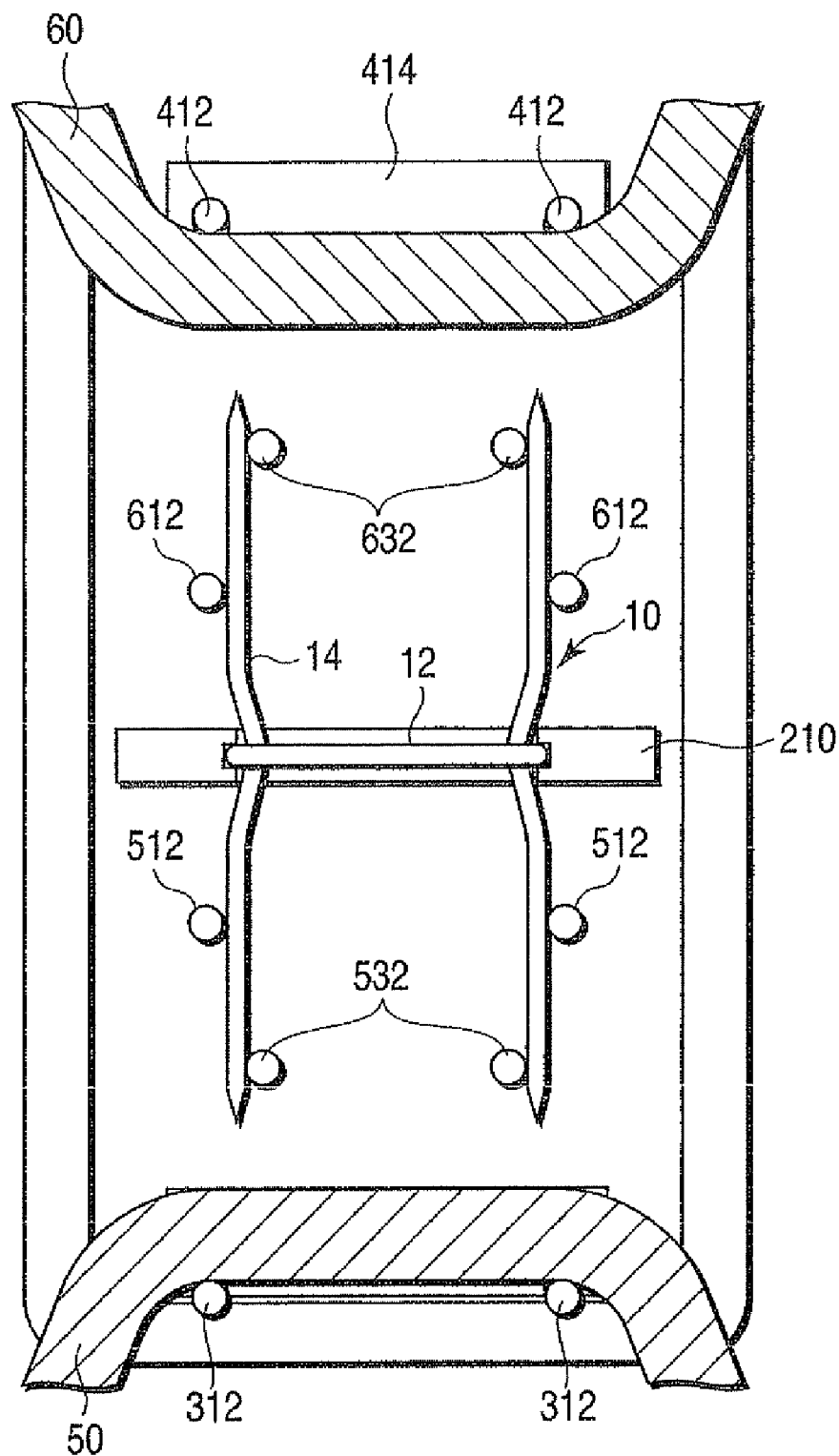
F I G. 55

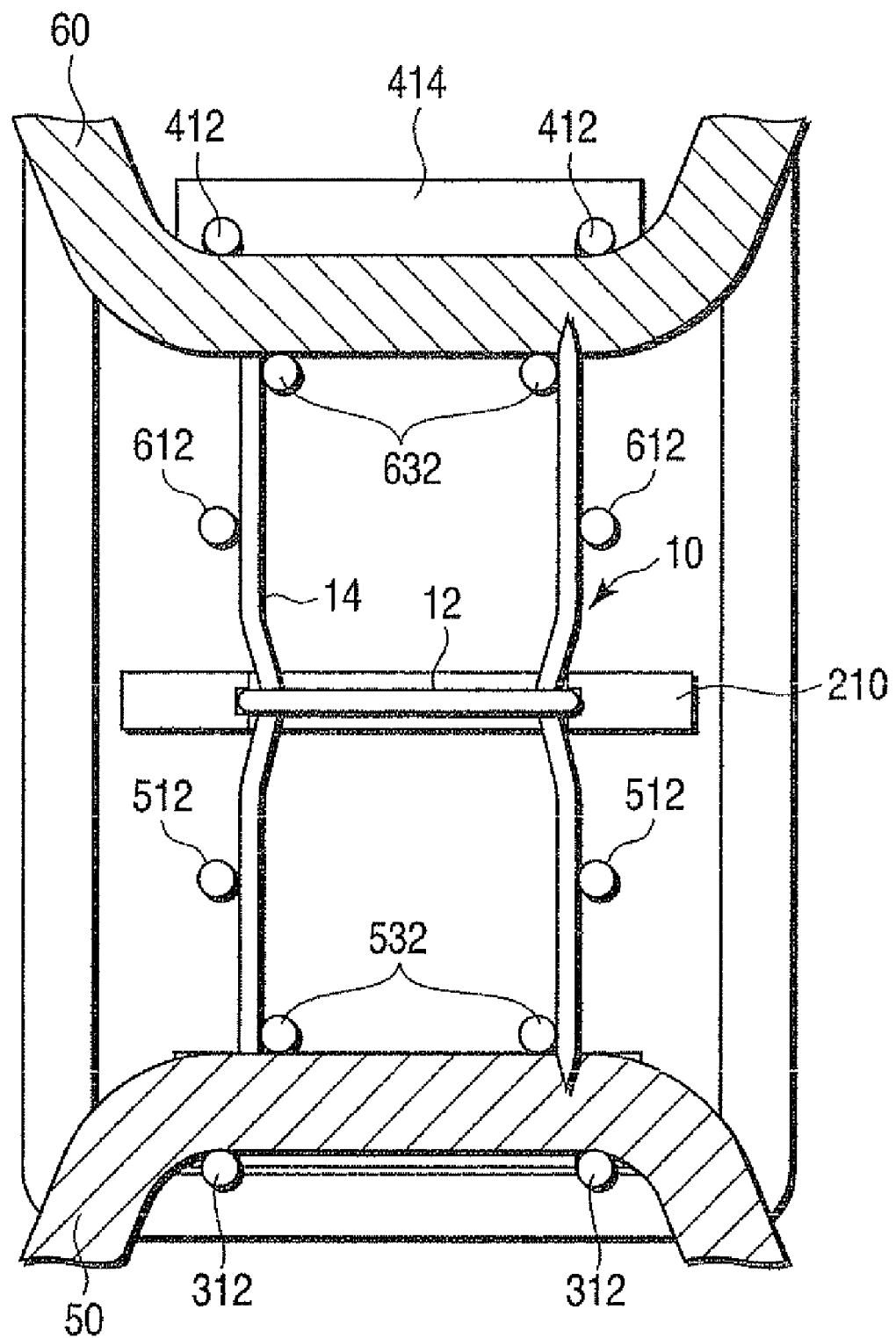
F I G. 56

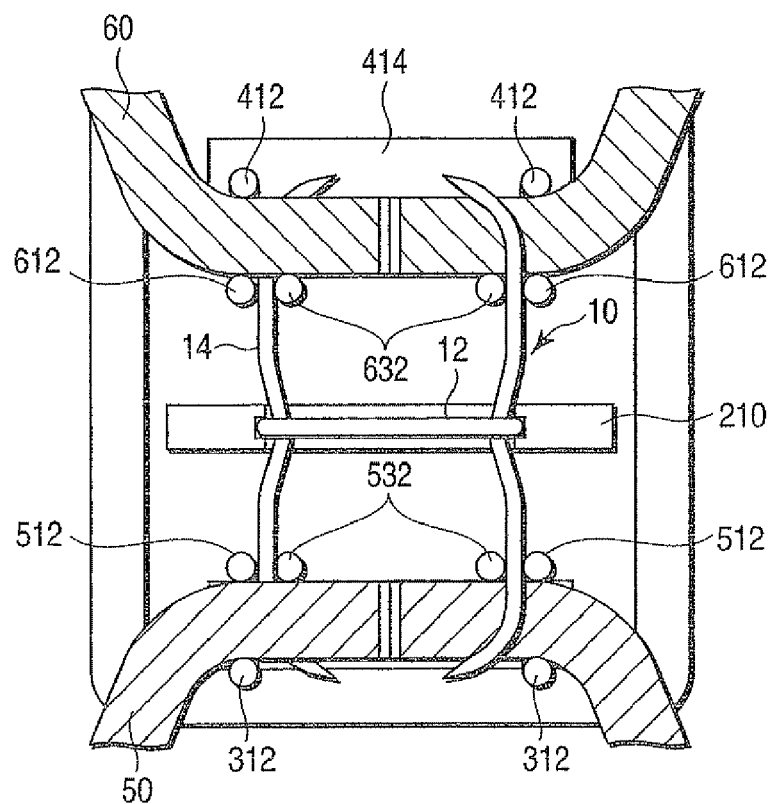
F I G. 61
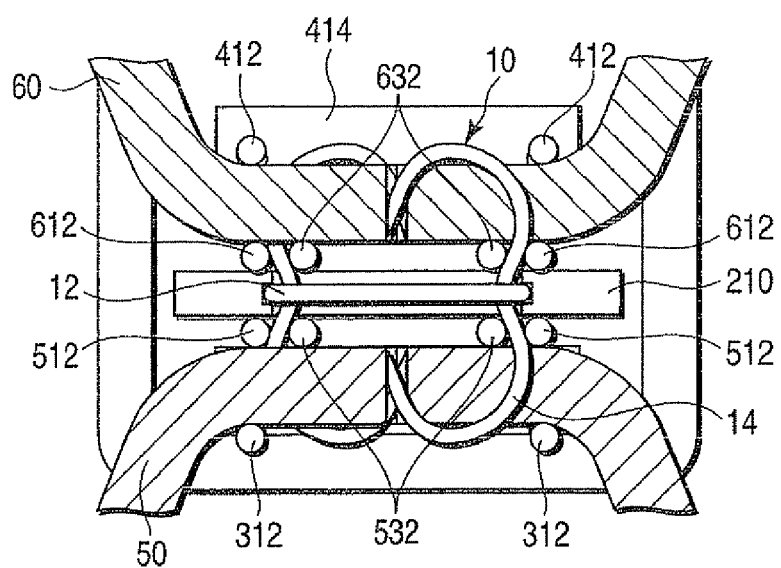
F I G. 62

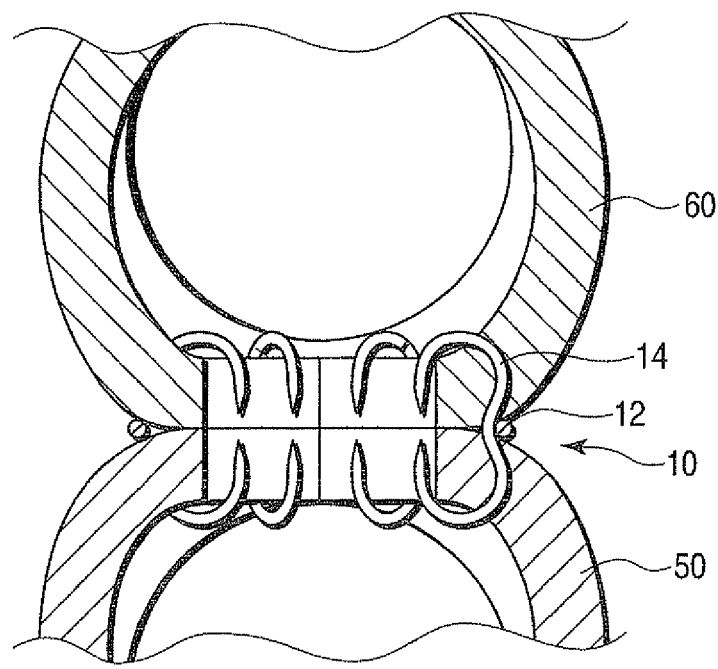
F I G. 65
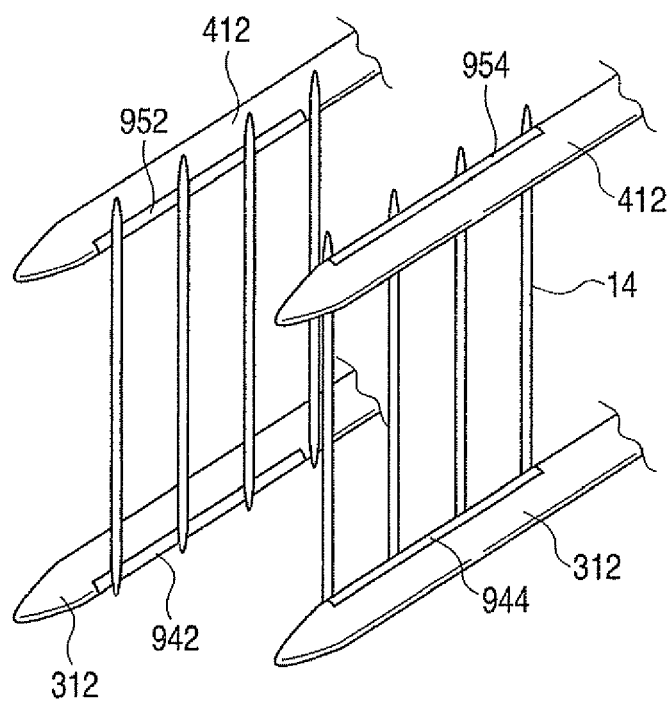
F I G. 66

HOLLOW TISSUE INOSCULATION APPARATUS

CROSS-REFERENCE TO RELATED APPLICATIONS

This application is based upon and claims the benefit of priority from prior Japanese Patent Application No. 2008-210028, filed Aug. 18, 2008, the entire contents of which are incorporated herein by reference.

BACKGROUND OF THE INVENTION

1. Field of the Invention

The present invention relates to a hollow tissue inosculation apparatus to inosculate two hollow tissues to each other.

2. Description of the Related Art

A hollow tissue inosculation apparatus includes an anastomotic apparatus to anastomose blood vessels as hollow tissues in coronary-artery bypass surgery, for example.

For example, JP-A 2001-190557 (KOKAI) discloses an instrument to hold and fix a bypass blood vessel when inosculating the bypass blood vessel to a coronary artery. When this equipment is moved, e.g., pulled up, an inner cavity can be seen to confirm an inosculated state without directly touching the bypass blood vessel.

JP-A H6-47050 (KOKAI) discloses a tissue suture instrument having observing means provided to a tissue suture member. This tissue suture instrument allows a sutured state to be observed and confirmed in use of the observing means.

BRIEF SUMMARY OF THE INVENTION

The present invention is directed to a hollow tissue inosculation apparatus to inosculate two hollow tissues to each other with a staple having a plurality of elastically deformable bent staple pins. The hollow tissue inosculation apparatus includes a staple holder to hold the staple, a curvature control mechanism to control curvature of the staple pins of the staple held in the staple holder, and a gap control mechanism to control gaps of the hollow tissues with respect to the staple holder. The curvature control mechanism substantially straightens the staple pins. The gap control mechanism reduces the gaps to cause the substantially straightened staple pins to penetrate through the hollow tissues. The hollow tissue inosculation apparatus also includes a detector to detect the staple pins of the staple that have penetrated through the hollow tissue.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 shows the inner mechanism of the treatment unit with an outer slider removed from the state depicted in FIG. 4;

FIG. 18 is a perspective view of the treatment unit in which coronary-artery supports are inserted in a coronary artery and graft supports are inserted in a graft;

FIG. 20 is a perspective view of the treatment nit in which the graft support mechanism is closed;

FIG. 21 is a side view of the treatment unit depicted in FIG. 20;

FIG. 34 is a front view of the treatment unit depicted in FIG. 32;

FIG. 40 is a front view of the treatment unit depicted in FIG. 38;

FIG. 46 is a front view of the treatment unit depicted in FIG. 44;

FIG. 55 is a front view of a treatment unit in which a coronary-artery support mechanism and a graft support mechanism support a coronary artery and a graft, respectively, in a hollow tissue inosculation apparatus according to a second embodiment of the present invention;

FIG. 56 is a front view of the treatment unit in which end portions of stable pins of a staple are stuck into the graft and the coronary artery;

FIG. 61 is a front view of the treatment unit in which the end portions of the staple pins of the staple have penetrated through the graft and the coronary artery;

FIG. 62 is a front view of the treatment unit in which the graft supports, coronary-artery supports, and pillars have been moved closer to the staple holder;

FIG. 65 is cross-sectional view of the graft and the coronary artery that are inosculated to each other and shown in FIG. 63;

FIG. 66 shows a coronary-artery supports and a graft supports including optical sensors to detect the staple pins of the staple that have penetrated through the coronary artery and the graft.

DETAILED DESCRIPTION OF THE INVENTION

An embodiment according to the present invention will now be described hereinafter with reference to the accompanying drawings.

First Embodiment

This embodiment concerns a staple and a hollow tissue inosculation apparatus to inosculate two hollow tissues to each other. The hollow tissues are specifically blood vessels.

Figure 1:
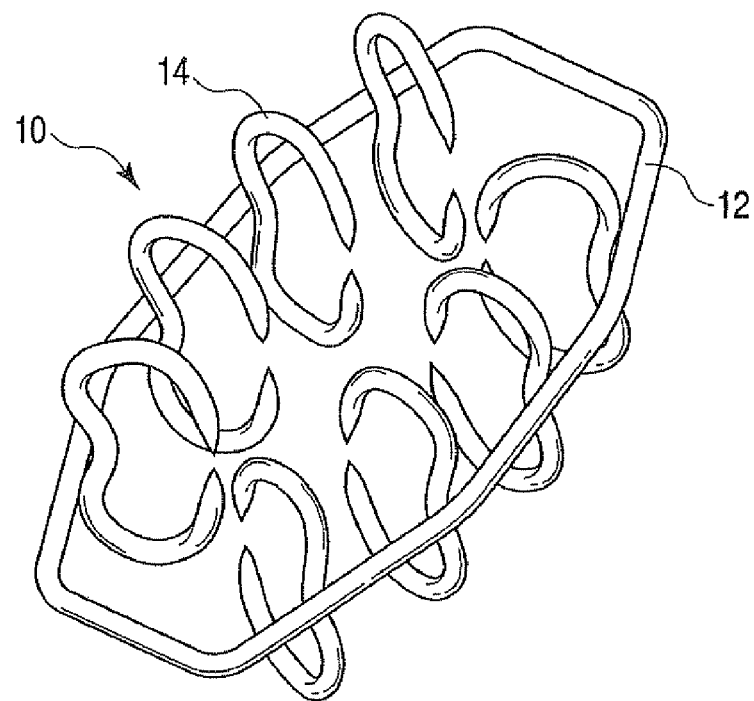
FIG. 1 shows a staple in a natural state according to an embodiment of the present invention.
Figure 2:
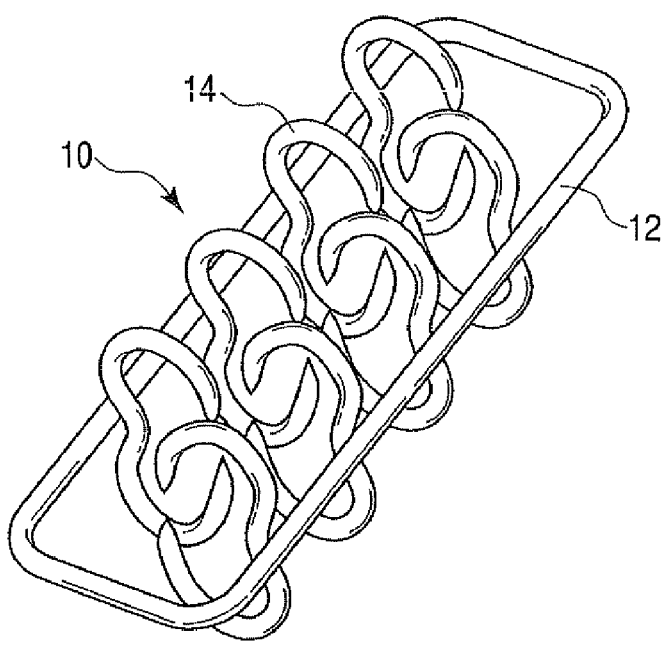
FIG. 2 shows the staple when inserted into a hollow tissue inosculation apparatus according to an embodiment of the present invention.

The staple as a fastening to inosculate two hollow tissues will be first described with reference to FIGS. 1 and 2. Each of FIGS. 1 and 2 is a perspective view of the staple according to this embodiment. FIG. 1 shows the staple in a natural state, and FIG. 2 shows the staple inserted into the hollow tissue inosculation apparatus.

As shown in FIGS. 1 and 2, the staple 10 has an elastically deformable ring-like ring member 12 and a plurality of elastically deformable bent staple pins 14. Each staple pin 14 is fixed on the inner side of the ring member 12. An axis of the ring member 12 is on a plane, an axis of each staple pin 14 is on a different plane, and these planes are substantially orthogonal to each other. Here, an axis of a member means a line extending along this member. For example, an axis of the member is a line running through the center of a cross section obtained by cutting away each portion of this member based on a plane running through its center of curvature.

The ring member 12 has a shape expanded toward the outside in a natural state. The ring member 12 has a closed ring shape.

Part of each staple pin 14 close to a position fixed to the ring member 12 is bent toward the outside of the ring member 12, and the other parts, which are closer to ends than that part, are bent in a C-like shape toward the inside of the ring member 12. Both ends of each staple pin 14 face each other in the natural state. These staple pins 14 are arranged so as not to come into contact with each other. For example, the same number of staple pins 14 are arranged on two sides, the staple pins on both sides are arranged at the same fixed pitch, and the staple pins 14 on one side deviate from the staple pins 14 on the other side at a half pitch.

Although the ring member 12 is, herein, formed of a wire rod, the present invention is not restricted thereto, and the ring member 12 may be formed of a plate material or a molding material. Although each staple pin 14 is also, herein, formed of a wire rod the present invention is not restricted thereto, and each staple pin 14 may be formed of a plate material or a molding material. The ring member 12 and the staple pins 14 are formed by bonding different members, for example, but the present invention is not restricted thereto, and they may be integrally formed. Although the staple 10 has the eight staple pins 14 here, the number of the staple pins 14 is not restricted thereto, and it may be freely changed. Further, a gap, a relative position, or a relative direction of the staple pins 14 can be also freely changed.

For example, the ring member 12 is formed of a hyperelastic material, and the staple pins 14 are also formed of a hyperelastic material. Here, the "hyperelastic material" means a material that shows a hyperelastic effect.

The "hyperelastic effect" means that strain is immediately eliminated to restore the member to its original shape when stress is removed even though deformation strain (approximately 8%) exceeding Hook's law is given. In a regular metal material, when deformation strain (approximately 0.5% or above) exceeding an elastic area is given, strain corresponding to elastic deformation alone is eliminated and permanent strain remains even though stress is removed.

In hyperelasticity generation mechanism, when force is applied in a parent phase, martensite is generated from the parent phase, and each crystal sequentially changes its direction, thereby producing macroscopic deformation of an outer shape. When the force is removed, the parent phase is restored while maintaining connection between crystals, and hence the microscopic shape returns to the original state.

Alloy having the hyperelastic effect includes not only a titanium-nickel (Ti—Ni) alloy but also a copper-aluminum-nickel alloy, a copper-zinc-aluminum alloy, and a nickel-aluminum alloy. In recent years, it further includes an Fe—Al-based alloy that shows great hyperelasticity without changing a martensite conformation.

The ring member 12 and the staple pins 14 are not restricted to the hyperelastic materials, and they may be formed of an arbitrary biocompatible material having a wide elasticity range including plastic or ceramic.

Figure 3:
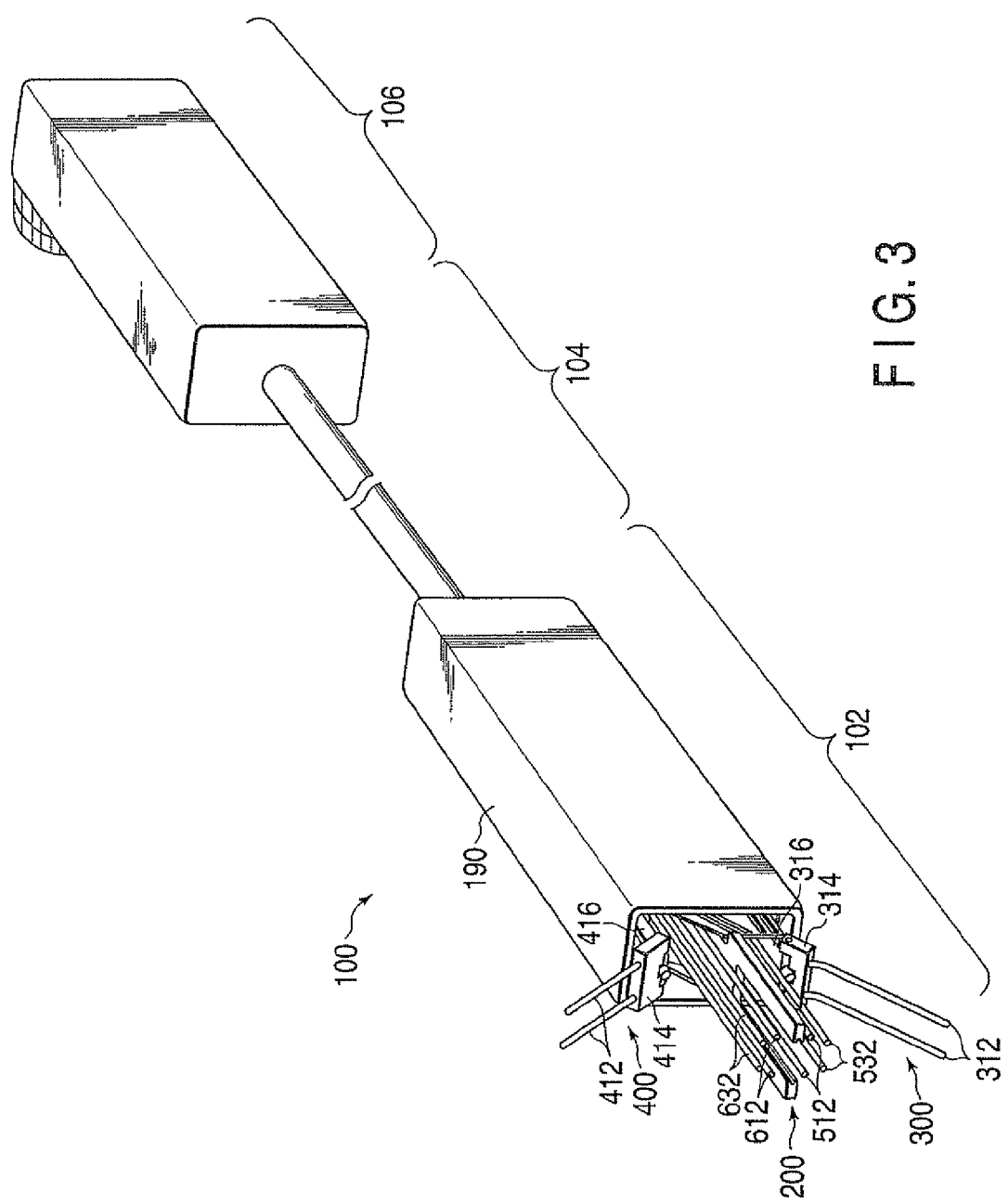
FIG. 3 shows an appearance of the hollow tissue inosculation apparatus according to an embodiment of the present invention.
Figure 4:
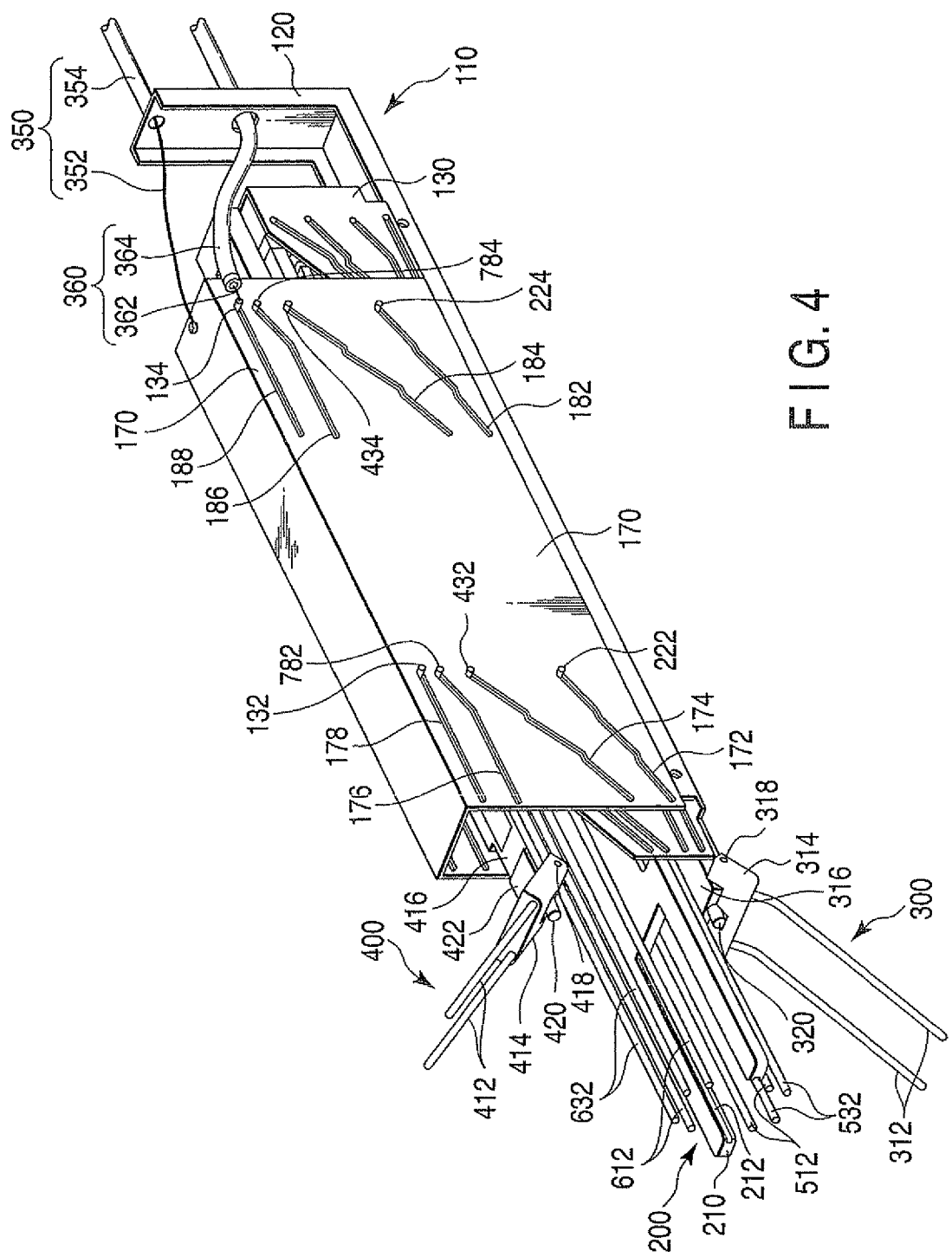
FIG. 4 shows an inner mechanism of a treatment unit depicted in FIG. 3.
Figure 6:
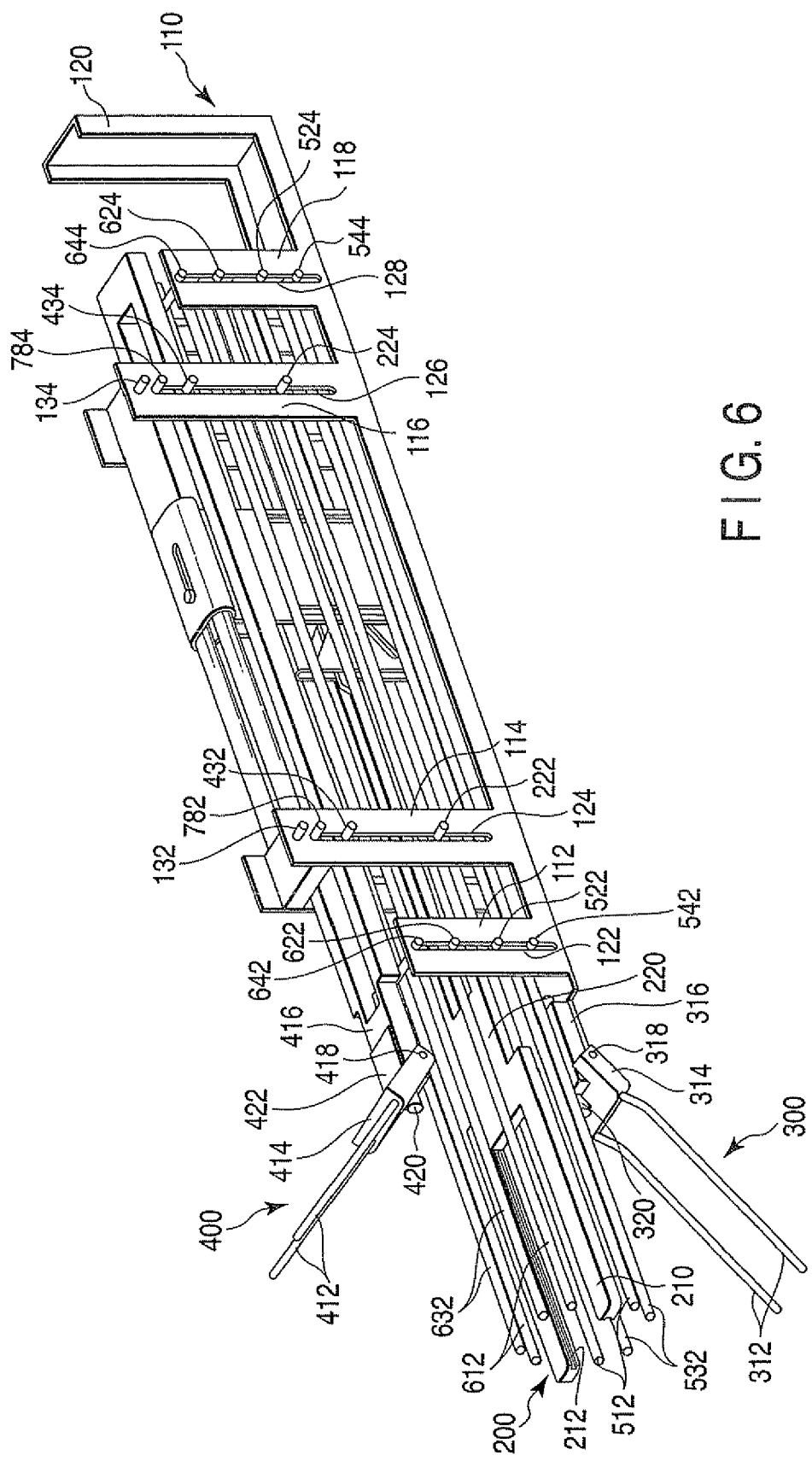
FIG. 6 shows the inner mechanism of the treatment unit with an inner slider removed from the state depicted in FIG. 5.
Figure 7:
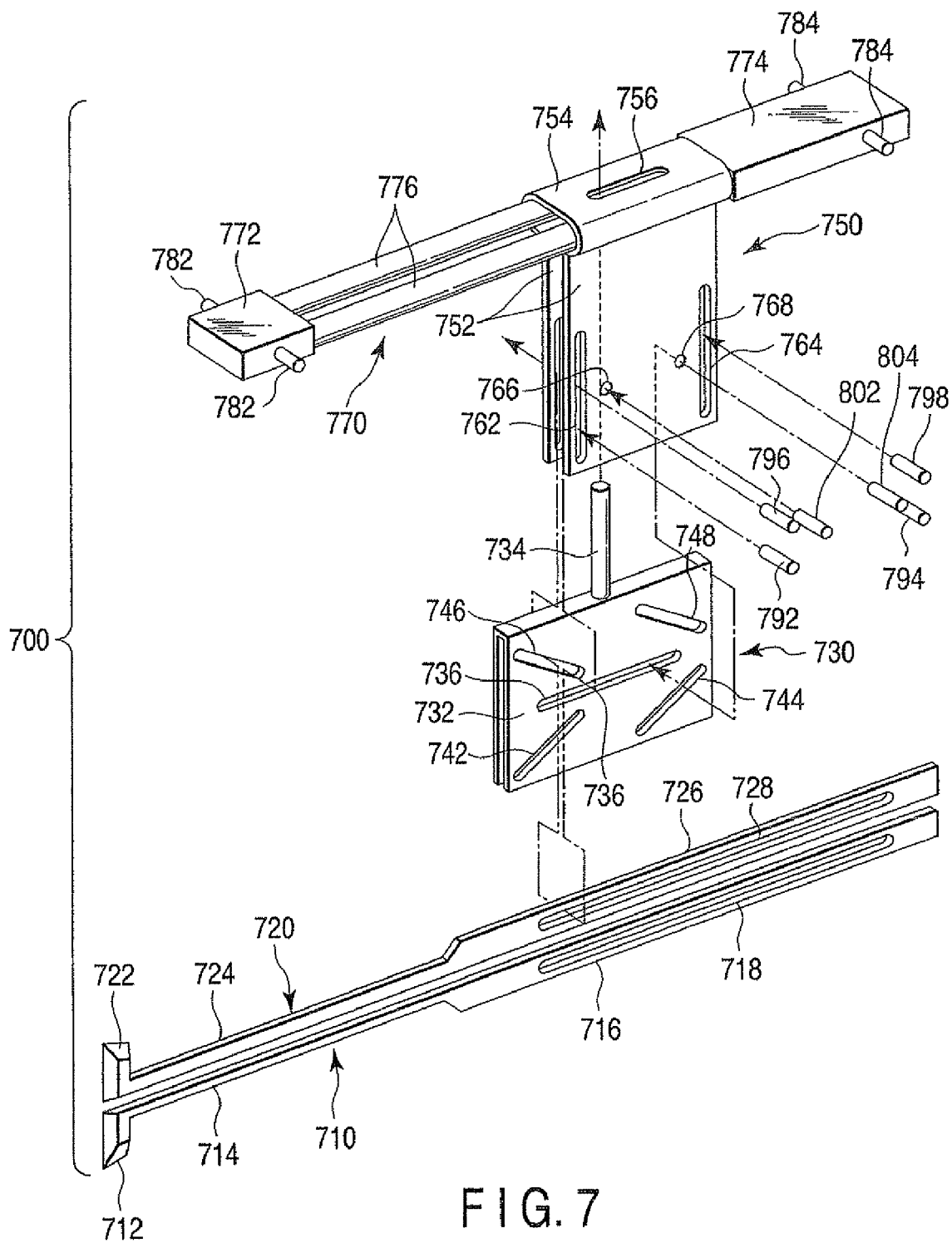
FIG. 7 is an exploded perspective view of an incision mechanism built in the treatment unit depicted in FIG. 3.
Figure 8:
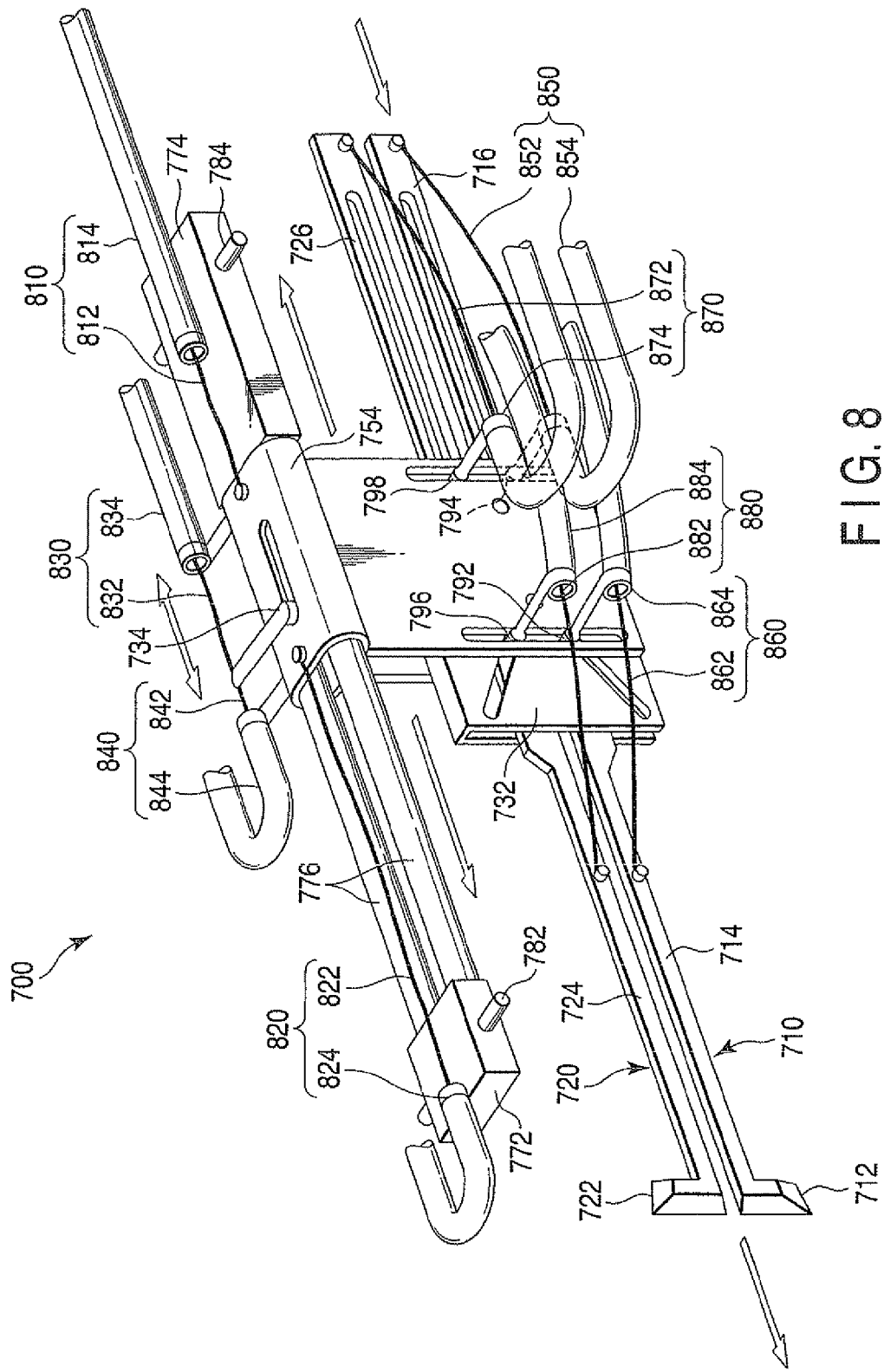
FIG. 8 is an assembly completion diagram of the incision mechanism depicted in FIG. 7.

The hollow tissue inosculation apparatus to inosculate two hollow tissues by using the staple depicted in FIGS. 1 and 2 will now be described with reference to FIGS. 3 to 8. FIG. 3 shows an appearance of the hollow tissue inosculation apparatus according to this embodiment. FIGS. 4 to 6 show an inner mechanism of a treatment unit depicted in FIG. 3. FIGS. 7 and 8 show an incision mechanism built in the treatment unit depicted in FIG. 3.

In the following description, the hollow tissue inosculation apparatus is a so-called anastomosing apparatus used in coronary-artery bypass surgery, which inosculates a different blood vessel (a graft) to a coronary artery that is narrowed or blocked. That is, one of the two hollow tissues is the coronary artery, and the other is the graft. These tissues are reflected in names of respective members.

As shown in FIG. 3, the hollow tissue inosculation apparatus 100 has a treatment unit 102 to inosculate the coronary artery to the graft, an operation unit 106 to operate the treatment unit 102, and a connecting rod 104 connecting the treatment unit 102 to the operation unit 106. The operation unit 106 is provided with operation knobs to operate each portion in the treatment unit 102.

As shown in FIG. 3, the treatment unit 102 has a staple holder 200 to hold the staple 10, a coronary-artery support mechanism 300 to support the coronary artery, and a graft support mechanism 400 to support the graft.

As shown in FIGS. 4 to 6, the staple holder 200 has two prismatic staple holding members 210 to hold the staple. The staple holding members 210 are arranged at a fixed interval narrower than a width of the ring member 12 of the staple 10 in the natural state therebetween, and they extends in parallel in the forward direction from a base member 220. Each staple holding member 210 has a groove 212 to receive the ring member 12 of the staple on a surface facing a counterpart. The staple holding members 210 and the base member 220 are integrally formed, for example.

In the following description, directions perpendicular to a plane including a central axis of the two staple holding members 210 will be referred to as upward-and-downward directions, directions along which the two staple holding members 210 extends will be referred to as a forward-and-backward directions, and directions perpendicular to the upward-and-downward directions and the forward-and-backward directions will be referred to as lateral directions for convenience of explanation. Moreover, in regard to the upward-and-downward directions, a direction that the graft support mechanism 400 is placed with respect to the staple holder 200 will be referred to as an upward direction, and a direction that the coronary-artery support mechanism 300 is placed will be referred to as a downward direction. Additionally, in regard to the forward-and-backward directions, a direction extending from a fixed end of the staple holding member 210 toward a free end of the same will be referred to as a forward direction, and its opposite direction will be referred to as a backward direction.

As shown in FIGS. 4 to 6, the coronary-artery support mechanism 300 includes a pair of coronary-artery supports 312 extending in parallel to each other, a fixing portion 314 to which the coronary-artery supports 312 are fixed, and a base portion 316 to which the fixing portion 314 is disposed. The fixing portion 314 is coupled with the base portion 316 through a shaft 318 so as to swivel with respect to the base portion 316 on the center of the shaft 318. The base portion 316 is fixed to the frame 110.

As shown in FIGS. 4 to 6, the graft support mechanism 400 includes a pair of graft supports 412 extending in parallel to each other, a fixing portion 414 to which the graft supports 412 are fixed, a base portion 416 to which the fixing portion 414 is fixed. The fixing portion 414 is coupled with the base portion 416 through a shaft 418 so as to swivel with respect to the base portion 416 on the center of the shaft 418.

As shown in FIGS. 4 to 6, the treatment unit 102 also has a pair of outer pillars 512 extending in parallel to each other and a pair of inner pillars 532 extending in parallel in order to control curvature of the staple pins 14 on the lower side, i.e., the coronary artery side, of the staple 10. The outer pillars 512 are coupled with each other, and a relative positional relationship of these pillars is maintained constant. The inner pillars 532 are coupled with each other, and a relative positional relationship of these pillars is maintained constant. The outer pillars 512 come into contact with the outer side of the staple pins 14 of the staple 10 held in the staple holder 200, and the inner pillars 532 come into contact with the inner side of the staple pins 14 of the staple 10 held in the staple holder 200.

Likewise, as shown in FIGS. 4 to 6, the treatment unit 102 has a pair of outer pillars 612 extending in parallel to each other and a pair of inner pillars 632 extending in parallel to each other in order to control curvature of the staple pins 14 on the upper side, i.e., the graft side, of the staple 10. The outer pillars 612 are coupled with each other, and a relative positional relationship of these pillars is maintained constant. The inner pillars 632 are coupled with each other, and a relative positional relationship of these pillars is maintained constant. The outer pillars 612 come into contact with the outer side of the staple pins 14 of the staple 10 held in the staple holder 200, and the inner pillars 632 come into contact with the inner side of the staple pins 14 of the staple 10 held in the staple holder 200.

The staple holder 200, the graft support mechanism 400, the outer pillars 512, the inner pillars 532, the outer pillars 612, and the inner pillars 632 are allowed to move in the upward-and-downward directions by a groove cam mechanism, which will be explained later. This groove cam mechanism is covered with a cover 190 as shown in FIG. 3.

The treatment unit 102 includes an incision mechanism 700 to incise the coronary artery and the graft.

The incision mechanism 700 includes a cutter 710 to incise the coronary artery and a cutter 720 to incise the graft as shown in FIGS. 7 and 8. The cutter 710 has a support portion 716 having a long groove 718, an arm 714 extending from the support portion 716, and a blade 712 provided at an end portion of the arm 714. The cutter 720 has substantially the same structure as the cutter 710, and has a support portion 726 having a long groove 728, an arm 724 extending from the support portion 726, and a blade 722 provided at an end portion of the arm 724 like the cutter 710.

The incision mechanism 700 has a support member 730 to support the cutters 710 and 720, a support member 750 to support the support member 730, and a guide 770 to support the support member 750.

The support member 730 has a plate-like member 732 bent into an inverted U shape and a columnar pin 734 fixed to the plate-like member 732. The plate-like member 732 has, on each of lateral both sides, a groove 736 positioned at a central portion, grooves 742 and 744 positioned below the groove 736, and grooves 746 and 748 positioned above the groove 736. The groove 736 linearly extends in the forward-and-backward directions. The grooves 742 and 744 obliquely linearly extend with respect to the forward-and-backward directions, and a front end portion of each of the grooves 742 and 744 is positioned below a rear end portion of the same. The grooves 746 and 748 obliquely linearly extend with respect to the forward-and-backward directions, and a front end portion of each of the groove 746 and 748 is positioned above a rear end portion of the same. The pin 734 extends in the upward-and-downward directions.

The support member 750 is formed of a bent plate-like member, and has two plate-like portions 752 parallel to each other and a bent portion 754 extending to be bent in a C-like shape between the two plate-like portions 752. Each of the plate-like portions 752 has a groove 762 positioned on the front side, a groove 764 positioned on the rear side, a hole 766 at the back of the groove 762, and a hole 768 in front of the groove 764. The grooves 762 and 764 extend in the upward-and-downward directions in parallel to each other. The holes 766 and 768 are positioned near the center in relation to the upward-and-downward directions. The bent portion 754 has a groove 756 into which the pin 734 of the support member 730 is inserted on the upper side thereof. The groove 756 extends in the forward-and-backward directions.

The guide 770 includes two rails 776 running on the inside of the bent portion 754 of the support member 750, a front fixing portion 772 to which front end portions of the rails 776 are fixed, and a rear fixing portion 774 to which rear end portions of the rails 776 are fixed. The rails 776 support the support member 750 to be movable in the forward-and-backward directions. The front fixing portion 772 has a pair of pins 782 protruding laterally. The rear fixing portion 774 has a pair of pins 784 protruding laterally.

The support member 730 is arranged so that the pin 734 is inserted in the groove 756 of the support member 750, the plate-like member 732 is placed between the plate-like portions 752 of the support member 750, and the grooves 736 are aligned with the holes 766 and 768 of the support member 750, and a pin 802 is inserted into the holes 766 of the support member 750 and the grooves 736 of the support member 730. Further, a pin 804 is inserted into the holes 768 of the support member 750 and the grooves 736 of the support member 730. The support member 730 is supported to be movable in the forward-and-backward directions with respect to the support member 750 by such a groove mechanism.

The cutter 720 is arranged so that the support portion 726 is placed inside the plate-like member 732 of the support member 730, the long groove 728 is aligned with an overlapping portion of the grooves 746 of the support member 730 and the grooves 762 of the support member 750 and also aligned with an overlapping portion of the grooves 748 of the support member 730 and the grooves 764 of the support member 750. Furthermore, a pin 796 is inserted into the grooves 762 of the support member 750, the grooves 746 of the support member 730, and the long groove 728 of the cutter 720, and a pin 798 is inserted into the grooves 764 of the support member 750, the grooves 748 of the support member 730, and the long groove 728 of the cutter 720. The cutter 720 is supported to be movable in the upward-and-downward directions with respect to the support member 750 and movable in the forward-and-backward directions with respect to the support member 730 by such a groove cam mechanism.

The cutter 710 is arranged so that the support portion 716 is placed inside the plate-like member 732 of the support member 730 and the long groove 718 is aligned with an overlapping portion of the grooves 742 of the support member 730 and the grooves 762 of the support member 750 and also aligned with an overlapping portion of the grooves 744 of the support member 730 and the grooves 764 of the support member 750. Furthermore, a pin 792 is inserted into the grooves 762 of the support member 750, the grooves 742 of the support member 730, and the long groove 718 of the cutter 710, and a pin 794 is inserted into the grooves 764 of the support member 750, the grooves 744 of the support member 730, and the long groove 718 of the cutter 710. The cutter 710 is supported to be movable in the upward-and-downward directions with respect to the support member 750 and also movable in the forward-and-backward directions with respect to the support member 730 by such a groove cam mechanism.

In the thus configured incision mechanism 700, the cutter 710 and the cutter 720 move in the forward-and-backward directions for movement of the support member 750 in the forward-and-backward directions with respect to the guide 770. Furthermore, the cutter 710 moves in the downward direction and the cutter 720 moves in the upward direction for movement of the support member 730 in the backward direction with respect to the support member 750. Contrarily, the cutter 710 moves up and the cutter 720 moves down for movement of the support member 730 in the forward direction with respect to the support member 750.

As shown in FIG. 8, wire assemblies 810, 820, 830, 840, 850, 860, 870, and 880 to operate the incision mechanism 700 are disposed to the incision mechanism 700.

The wire assemblies 810 and 820 are to move the support member 750 in the forward-and-backward directions with respect to the guide 770. The wire assembly 810 includes a wire 812 fixed to the support member 750 and a wire outer tube 814 fixed to a rear fixing portion 774 of the guide 770. Moreover, the wire assembly 820 includes a wire 822 fixed to the support member 750 and a wire outer tube 824 fixed to a front fixing portion 772 of the guide 770. The wire assemblies 810 and 820 extend to the operation unit 106 through the connecting rod 104, and the wires 812 and 822 are coupled with the operation knob.

When the operation unit 106 is operated to pull the wire 822, the support member 750 is moved in the forward direction with respect to the guide 770. As a result, the support member 730 and the cutters 710 and 720 are integrally moved in the forward direction. Additionally, when the operation unit 106 is operated to pull the wire 812, the support member 750 is moved in the backward direction with respect to the guide 770. As a result, the support member 730 and the cutters 710 and 720 are integrally moved in the backward direction.

The wire assemblies 830 and 840 are to move the support member 730 in the forward-and-backward directions with respect to the support member 750. The wire assembly 830 includes a wire 832 fixed to the pin 734 of the support member 730 and a wire outer tube 834 fixed to a rear portion of the support member 750. Further, the wire assembly 840 includes a wire 842 fixed to the pin 734 of the support member 730 and a wire outer tube 844 fixed to a front portion of the support member 750. The wire assemblies 830 and 840 extend to the operation unit 106 through the connecting rod 104, and the wires 832 and 842 are coupled with the operation knob.

When the operation unit 106 is operated to pull the wire 842, the support member 730 is moved in the forward direction with respect to the support member 750. As a result, the pins 792 and 794 are moved in the upward direction, the cutter 710 is moved in the upward direction, the pins 796 and 798 are moved in the downward direction, and the cutter 720 is moved in the downward direction. Moreover, when the operation unit 106 is operated to pull the wire 832, the support member 730 is moved in the backward direction with respect to the support member 750. As a result, the pins 792 and 794 are moved in the downward direction, the cutter 710 is moved in the downward direction, the pins 796 and 798 are moved in the upward direction, and the cutter 720 is moved in the upward direction.

The wire assemblies 850 and 860 are to move the cutter 710 in the forward-and-backward directions with respect to the support member 730. The wire assembly 850 includes a wire 852 fixed to a rear portion of the support portion 716 of the cutter 710 and a wire outer tuber 854 fixed to the pin 794. Additionally, the wire assembly 860 includes a wire 862 fixed to the arm 714 of the cutter 710 and a wire outer tube 864 fixed to the pin 792. The wire assemblies 850 and 860 extend to the operation unit 106 through the connecting rod 104, and the wires 852 and 862 are coupled with the operation knob.

When the operation unit 106 is operated to pull the wire 852, the cutter 710 is moved in the forward direction with respect to the support member 730. Further, when the operation unit 106 is operated to pulled the wire 862, the support member 750 is moved in the backward direction with respect to the cutter 710.

Likewise, the wire assemblies 870 and 880 are to move the cutter 720 in the forward-and-backward directions with respect to the support member 730. The wire assembly 870 includes a wire 872 fixed to the rear portion of the support portion 726 of the cutter 720 and a wire outer tube 874 fixed to the pin 798. Furthermore, the wire assembly 880 includes a wire 882 fixed to the arm 724 of the cutter 720 and a wire outer tube 884 fixed to the pin 796. The wire assemblies 870 and 880 extend to the operation unit 106 through the connecting rod 104, and the wires 872 and 882 are coupled with the operation knob.

When the operation unit 106 is operated to pull the wire 872, the cutter 720 is moved in the forward direction with respect to the support member 730. Further, when the operation unit 106 is operated to pull the wire 882, the support member 750 is moved in the backward direction with respect to the cutter 720.

As explained above, in the incision mechanism 700, the cutter 710 and the cutter 720 can be independently operated in the upward-and-downward directions and the forward-and-backward directions.

As shown in FIGS. 4 to 6, the staple holder 200, the coronary-artery support mechanism 300, the graft support mechanism 400, the inner pillars 532, the outer pillars 612, the inner pillars 632, and the incision mechanism 700 are all mounted in the frame 110.

As shown in FIG. 6, the frame 110 has four pairs of side wall portions 112, 114, 116, and 118 extending upward in parallel to each other on lateral both sides, and also has one rear end wall portion 120 extending upward at a rear end portion. The side wall portions 112 and 118 have the same height. The side wall portions 114 and 116 have the same height. The height of the side wall portions 114 and 116 is larger than the height of the side wall portions 112 and 118. The side wall portions 112 and 118 have grooves 122 and 128 extending in the upward-and-downward directions, respectively. The grooves 122 and 128 have the same length. The side wall portions 114 and 116 have grooves 124 and 126 extending in the upward-and-downward directions, respectively. The grooves 124 and 126 have the same length. The side wall portions 114 have a pair of pins 132 protruding laterally at upper portions of the grooves 124. Furthermore, the side wall portions 116 have a pair of pins 134 protruding laterally at upper portions of the grooves 126.

The base portion 416 of the graft support mechanism 400 has a groove extending in the forward-and-backward directions, and both side portions of this groove extend on lateral both sides of the plate-like portions 752 of the support member 750 of the incision mechanism 700. The base member 220 of the staple holder 200 has a groove extending in the forward-and-backward directions, and both side portions of this groove extend on lateral both sides of the plate-like portions 752 of the support member 750 of the incision mechanism 700. The outer pillars 512 and the inner pillars 532 extend on lateral both sides of the plate-like portions 752 of the support member 750 of the incision mechanism 700. Likewise, the outer pillars 612 and the inner pillars 632 extend on lateral both sides of the plate-like portions 752 of the support member 750 of the incision mechanism 700.

As explained above, the front fixing portion 772 of the guide 770 of the incision mechanism 700 has the pair of pins 782 protruding laterally, and the rear fixing portion 774 has the pair of pins 784 protruding laterally. The pins 782 of the front fixing portion 772 run through the grooves 124 of the side wall portions 114 of the frame 110, and the pins 784 of the rear fixing portion 774 run through the grooves 126 of the side wall portions 116 of the frame 110. Further, the base portion 416 of the graft support mechanism 400 has two pairs of pins 432 and 434 protruding laterally. The pins 432 run through the grooves 124 of the side wall portions 114 of the frame 110, and the pins 434 run through the grooves 126 of the side wall portions 116 of the frame 110. Furthermore, the base member 220 of the staple holder 200 has two pairs of pins 222 and 224 protruding laterally. The pins 222 run through the grooves 124 of the side wall portions 114 of the frame 110, and the pins 224 run through the grooves 126 of the side wall portions 116 of the frame 110.

The inner pillars 632 have two pairs of pins 642 and 644 protruding laterally. The pins 642 run through the grooves 122 of the side wall portions 112 of the frame 110, and the pins 644 run through the grooves 128 of the side wall portions 118 of the frame 110. Moreover, the outer pillars 612 have two pairs of pins 622 and 624 protruding laterally. The pins 622 run through the grooves 122 of the side wall portions 112 of the frame 110, and the pins 624 run through the grooves 128 of the side wall portions 118 of the frame 110. Additionally, the outer pillars 512 have two pairs of pins 522 and 524 protruding laterally. The pins 522 run through the grooves 122 of the side wall portions 112 of the frame 110, and the pins 524 run through the grooves 128 of the side wall portions 118 of the frame 110. Further, the inner pillars 532 have two pairs of pins 542 and 544 protruding laterally. The pins 542 run through the grooves 122 of the side wall portions 112 of the frame 110, and the pins 544 run through the grooves 128 of the side wall portions 118 of the frame 110.

As shown in FIG. 5, an inner slider 140 is disposed to the frame 110 to be movable in the forward-and-backward directions with respect to the frame 110. The inner slider 140 is formed of a plate material that is bent in a substantially U-like shape as viewed from above, and has side wall portions that are parallel to each other on lateral both sides.

The inner slider 140 has grooves 152, 154, 156, and 158 in a forward part of each side wall portion and grooves 162, 164, 166, and 168 in a backward part of each side wall portion. The grooves 152, 154, 156, and 158 have the same shapes as the grooves 162, 164, 166, and 168. The grooves 152 and 162 entirely linearly extend in the forward-and-backward directions. Each of the grooves 154 and 164 has a forward part linearly extending in the forward-and-backward directions and a backward part obliquely linearly extending with respect to the forward-and-backward directions. The backward part of each of the grooves 154 and 164 is upwardly inclined in the backward direction. Each of the grooves 156 and 166 has a forward part and a backward part, both of which linearly extend with inclined with respect to the forward-and-backward directions. Both the forward part and the backward part of each of the grooves 156 and 166 are upwardly inclined in the backward direction. Each of the grooves 158 and 168 has a forward part and a backward part, both of which linearly extend with inclined with respect to the forward-and-backward directions. Both the forward part and the backward part of each of the grooves 158 and 168 are likewise upwardly inclined in the backward direction, and inclination of the backward part is larger than that of the forward part.

The pins 542 and 544 of the inner pillars 532 protruding through the grooves 122 and 128 of the side wall portions 112 and 118 of the frame 110 are inserted in the grooves 152 and 162, respectively. The pins 522 and 524 of the outer pillars 512 protruding through the grooves 122 and 128 of the side wall portions 112 and 118 of the frame 110 are inserted in the grooves 154 and 164, respectively. The pins 622 and 624 of the outer pillars 612 protruding through the groves 122 and 128 of the side wall portions 112 and 118 of the frame 110 are inserted in the grooves 156 and 166, respectively. The pins 642 and 644 of the inner pillars 632 protruding through the grooves 122 and 128 of the side wall portions 112 and 118 of the frame 110 are inserted in the grooves 158 and 168, respectively.

Further, each side wall portion of the inner slider 140 also has a groove 142 at the back of the grooves 152, 154, 156, and 158 and a groove 144 in front of the grooves 162, 164, 166, and 168. The groove 142 and the groove 144 have the same shape. Each of the grooves 142 and 144 has a forward part and a backward part, both of which linearly extend with inclined with respect to the forward-and-backward directions. Both the forward part and the backward part of each of the grooves 42 and 144 are upwardly inclined in the backward direction, and inclination of the backward part is larger than that of the forward part.

The pins 222 and 224 of the staple holder 200 protruding through the grooves 124 and 126 of the side wall portions 114 and 116 of the frame 110 are inserted in the grooves 142 and 144, respectively.

With such a groove cam mechanism, backward movement of the inner slider 140 with respect to the frame 110 causes the outer pillars 512, the staple holder 200, the outer pillars 612, the inner pillars 632, and the inner pillars 532 to move closer to each other, so that a relative gap of these members in the upward-and-downward directions is narrowed. Contrarily, forward movement of the inner slider 140 with respect to the frame 110 causes the outer pillars 512, the staple holder 200, the outer pillars 612, the inner pillars 632, and the inner pillars 532 to move away from each other, so that the relative gap of these members in the upward-and-downward directions is widened.

Wire assemblies 550 and 560 to move the inner slider 140 in the forward-and-backward directions with respect to the frame 110 are provided. The wire assembly 550 includes a wire 552 fixed to the pin 544 and a wire outer tube 554 fixed at a rear end portion of the inner slider 140. Furthermore, the wire assembly 560 includes a wire 562 fixed at the rear end portion of the inner slider 140 and a wire outer tube 564 fixed at the rear end wall portion 120 of the frame 110. The wire assemblies 550 and 560 extend to the operation unit 106 through the connecting rod 104, and the wires 552 and 562 are coupled with the operation knob.

When the operation unit 106 is operated to pull the wire 562, the inner slider 140 is moved in the backward direction with respect to the frame 110. Consequently, as explained above, the relative gap of the inner pillars 532, the outer pillars 512, the staple holder 200, the outer pillars 612, and the inner pillars 632 is narrowed. Furthermore, when the operation unit 106 is operated to pull the wire 552, the inner slider 140 is moved in the forward direction with respect to the frame 110. Consequently, as explained above, the relative gap of the inner pillars 532, the outer pillars 512, the staple holder 200, the outer pillars 612, and the inner pillars 632 is widened.

As will be described later in detail, when the inner pillars 532, the outer pillars 512, the outer pillars 612, and the inner pillars 632 are moved away from the staple holder 200 from a state where they are close to the staple holder 200, the staple pins 14 of the staples 10 held in the staple holder 200 are stretched substantially straight from the bent state. Moreover, when the inner pillars 532, the outer pillars 512, the outer pillars 612, and the inner pillars 632 are moved closer to the staple holder 200 from the state where they are apart from the staple holder 200, the staple pins 14 of the staple 10 are restored to the naturally bent state from the straightened state. That is, the inner pillars 532, the outer pillars 512, the outer pillars 612, the inner pillars 632, and the mechanism to move these members in the upward-and-downward directions constitute a curvature control mechanism to control curvature of the staple pins 14 of the staple 10.

As shown in FIG. 4, an outer slider 170 is disposed to the frame 110 to be movable in the forward-and-backward directions with respect to the frame 110. The outer slider 170 is formed of a plate material that is bent in a substantially-U-like shape, and has side wall portions that are parallel to each other on lateral both sides.

The outer slider 170 has grooves 172, 174, 176, and 178 in a forward part of each side wall portion and grooves 182, 184, 186, and 188 in a backward part of each side wall portion. The grooves 172, 174, 176, and 178 have the same shapes as the grooves 182, 184, 186, and 188, respectively. Each of the grooves 172 and 178 has a forward part, a central part, and a backward part, which linearly extend with inclined in the forward-and-backward directions. The forward part, the central part, and the backward part of each of the grooves 172 and 182 are all inclined upward in the backward direction. Each of the grooves 174 and 184 also has a forward part, a central part, and a backward part, which linearly extend with inclined in the forward-and-backward directions. The forward part, the central part, and the backward part of each of the grooves 174 and 184 are all inclined upward in the backward direction. Each of the grooves 176 and 186 has a forward part and a central part, which linearly extend in the forward-and-backward directions, and a backward part, which linearly extends with inclined in the forward-and-backward directions. The backward part of each of the grooves 176 and 186 is inclined upward in the backward direction. The grooves 178 and 188 entirely linearly extend in the forward-and-backward directions.

The pins 222 and 224 of the staple holder 200 protruding through the grooves 124 and 126 in the side wall portions 114 and 116 of the frame 110 are inserted in the grooves 172 and 182, respectively. The pins 432 and 434 of the graft support mechanism 400 protruding through the grooves 124 and 126 in the side wall portions 114 and 116 of the frame 110 are inserted in the grooves 174 and 184, respectively. The pins 782 and 784 of the incision mechanism 700 protruding through the grooves 124 and 126 in the side wall portions 114 and 116 of the frame 110 are inserted in the grooves 176 and 186, respectively. The pins 132 and 134 of the frame 110 are inserted in the grooves 178 and 188, respectively.

When such a groove cam mechanism is adopted, backward movement of the outer slider 170 with respect to the frame 110 causes the staple holder 200 and the graft support mechanism 400 to move downward to get closer to the coronary-artery support mechanism 300, so that the relative gap of these members in the upward-and-downward directions is narrowed. Meanwhile, the incision mechanism 700 is moved downward only while the relative gap of the staple holder 200, the graft support mechanism 400, and the coronary-artery support mechanism 300 is large, but otherwise maintained this height. Contrarily, forward movement of the outer slider 170 with respect to the frame 110 causes the staple holder 200 and the graft support mechanism 400 to move upward to get away from the coronary-artery support mechanism 300, so that the relative gap of these members in the upward-and-downward directions is widened. Meanwhile the incision mechanism 700 is moved upward only while the relative gap of the staple holder 200, the graft support mechanism 400, and the coronary-artery support mechanism 300 is large, but otherwise maintained this height.

Wire assemblies 350 and 360 to move the outer slider 170 in the forward-and-backward directions with respect to the frame 110 are provided. The wire assembly 350 includes a wire 352 fixed at the rear end portion of the outer slider 170 and a wire outer tube 354 fixed at the rear end wall portion 120 of the frame 110. Additionally, the wire assembly 360 includes a wire 362 fixed at the pin 134 of each side wall portion 116 of the frame 110 and a wire outer tube 364 fixed at the rear end portion of the outer slider 170. The wire assemblies 350 and 360 extend to the operation unit 106 through the connecting rod 104, and the wires 352 and 362 are coupled with the operation knob.

When the operation unit 106 is operated to pull the wire 352, the inner slider 140 is moved in the backward direction with respect to the frame 110. Consequently, as described above, the relative gap of the staple holder 200, the graft support mechanism 400, and the coronary-artery support mechanism 300 is narrowed. Further, when the operation unit 106 is operated to pull the wire 362, the inner slider 140 is moved forward with respect to the frame 110. Consequently, as explained above, the relative gap of the staple holder 200, the graft support mechanism 400, and the coronary-artery support mechanism 300 is widened.

The staple holder 200, the graft support mechanism 400, and the mechanism to move these members constitute a gap control mechanism to control gaps of two hollow tissues, i.e., the coronary artery and the graft, with respect to the staple holder 200.

This gap control mechanism to control gaps of the coronary artery and the graft is driven when the outer slider 170 is moved in the forward-and-backward directions with respect to the frame 110. Further, the curvature control mechanism to control curvature of the staple pins 14 of the staple 10 is driven when the inner slider 140 is moved in the forward-and-backward directions with respect to the frame 110. That is, the gap control mechanism and the curvature control mechanism are independent from each other.

The graft support mechanism 400 will now be described in detail with reference to FIGS. 9 to 14.

Figure 9:
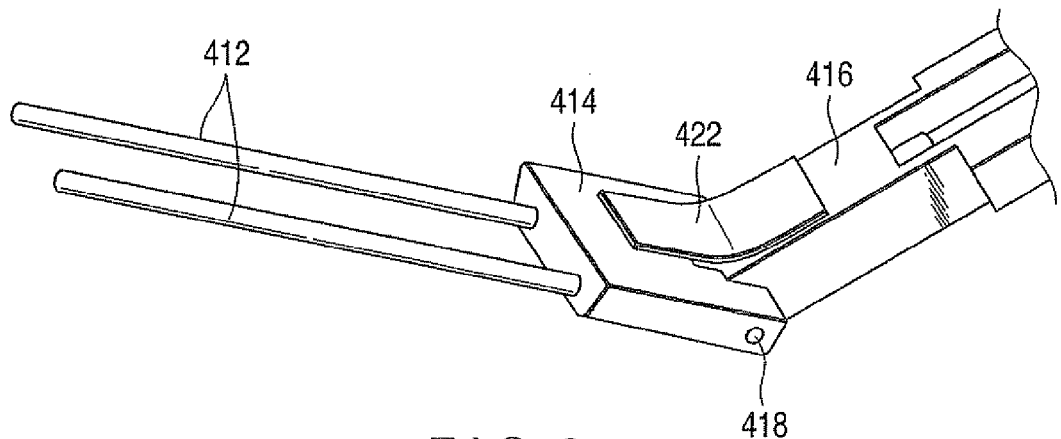
FIG. 9 is a perspective view showing an opened graft support mechanism as viewed from an obliquely upper position.
Figure 10:
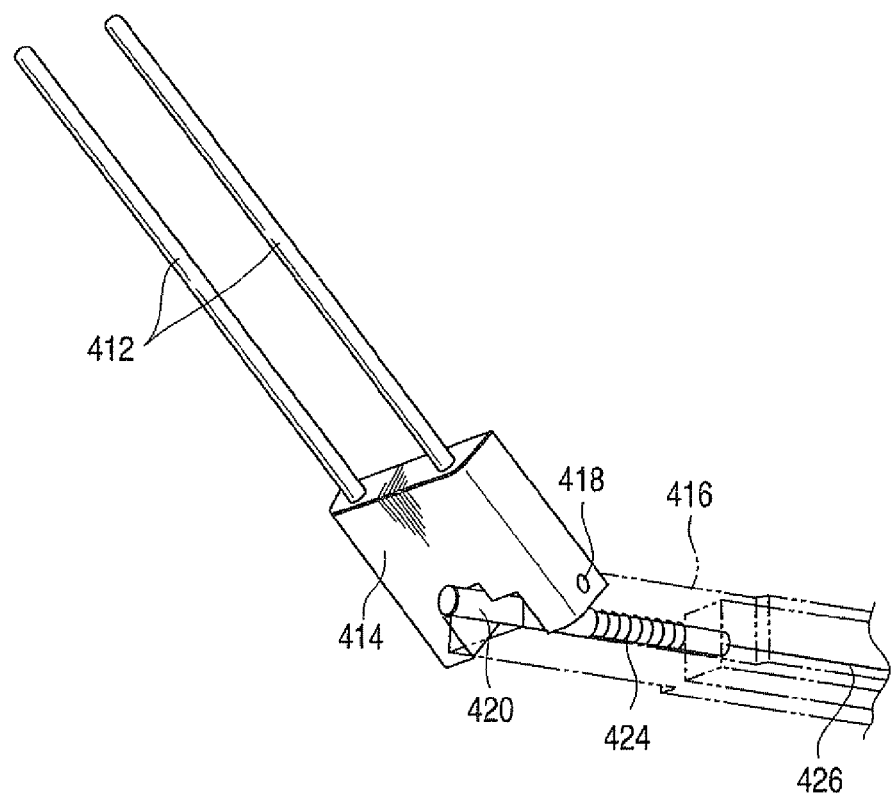
FIG. 10 is a perspective view showing the graft support mechanism depicted in FIG. 9 as viewed from an obliquely lower position.

As shown in FIG. 9, a leaf spring 422 is disposed to the fixing portion 414 and the base portion 416. The leaf spring 422 urges the fixing portion 414 to become straight with respect to the base portion 416, i.e., urges the fixing portion 414 to eliminate its inclination with respect to the base portion 416. Further, as shown in FIG. 10, a through hole is formed in the base portion 416, and a pin 420 is accommodated in this through hole. The pin 420 can move forward/backward in the through hole of the base portion 416. A coil spring 424 is incorporated in the through hole of the base portion 416. The coil spring 424 urges the pin 420 to protrude from the base portion 416. A wire 426 is connected with the pin 420. The wire 426 extends to the operation unit 106 through the connecting rod 104 to be coupled with the operation knob.

Figure 11:
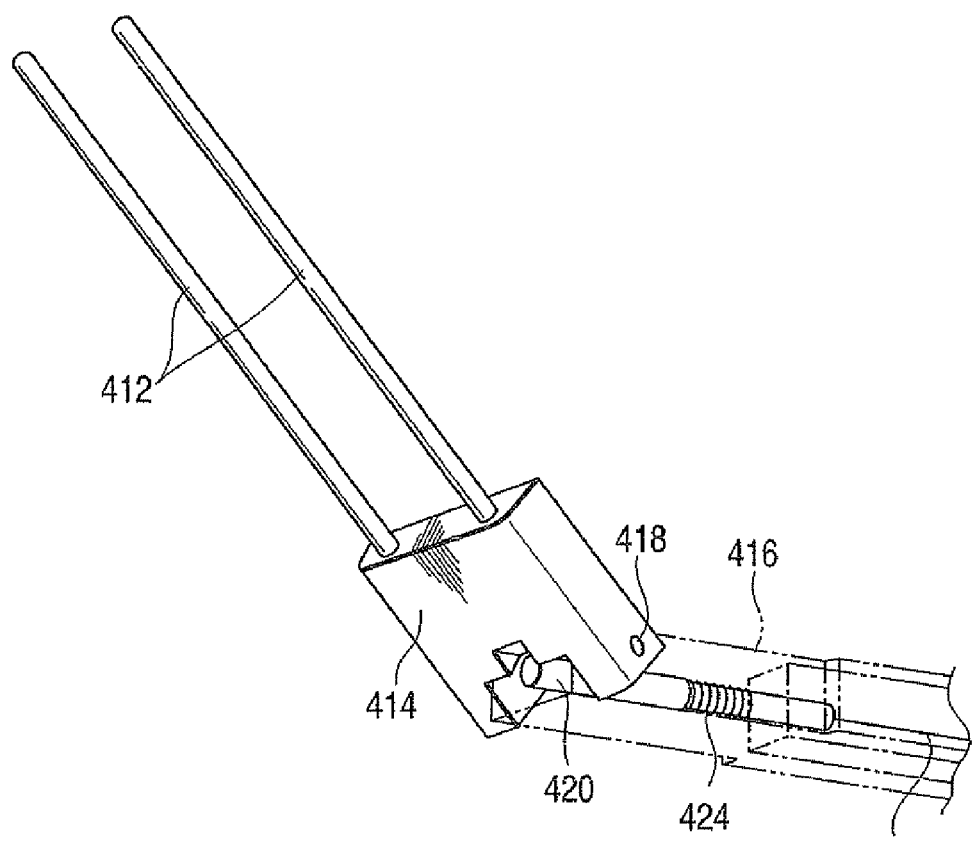
FIG. 11 is a perspective view showing the graft support mechanism that is unlocked when a pin is retracted into a base portion from a state depicted in FIG. 10 as viewed from an obliquely lower position.
Figure 12:
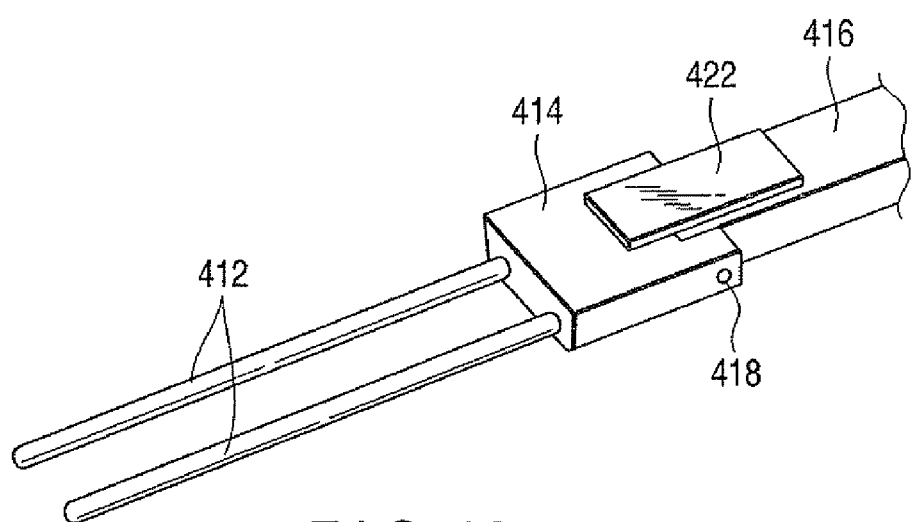
FIG. 12 is a perspective view showing the graft support mechanism in a state where a fixing portion linearly extends with respect to the base portion as viewed from an obliquely upper position.
Figure 13:
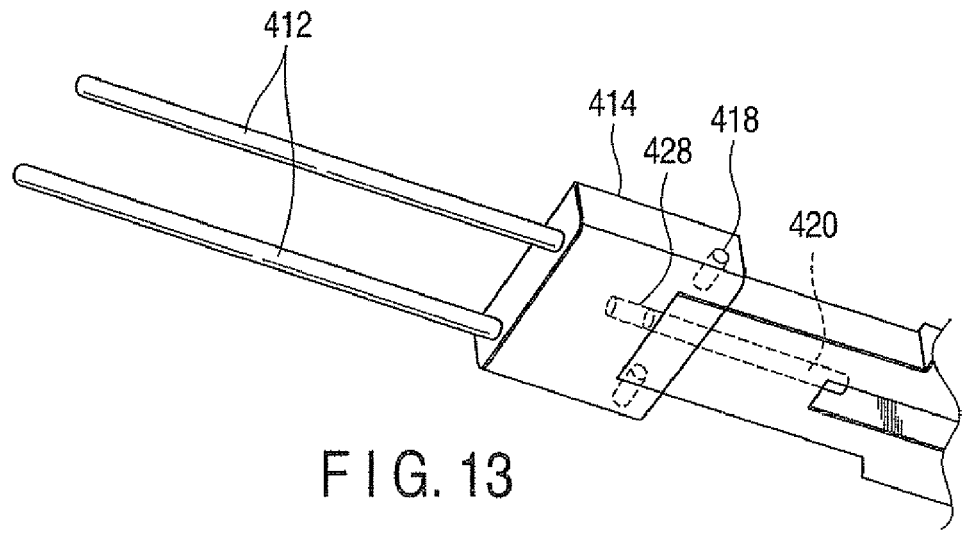
FIG. 13 is a perspective view showing the closed graft support mechanism as viewed from an obliquely lower position.

In a state depicted in FIGS. 9 and 10, the fixing portion 414 urged by the leaf spring 422 is contact with the pin 420 protruding from the base portion 416. As a result, the fixing portion 414 is locked in a posture in which the fixing portion 414 is inclined with respect to the base portion 416. In this specification, this state is called an opened state. When the wire 426 is pulled from this opened state against elastic force of the coil spring 424, the pin 420 is pulled into the base portion 416, so that the fixing portion 414 is unlocked as shown in FIG. 11. The fixing portion 414 swivels on the shaft 418 by utilizing on force received from the leaf spring 422. Swiveling of the fixing portion 414 is stopped when an end face of the fixing portion 414 comes into contact with the base portion 416. As a result, the fixing portion 414 gets still in a posture in which the fixing portion 414 linearly extends with respect to the base portion 416 as shown in FIG. 12. Then, when the wire 426 is loosened, the pin 420 protrudes from the base portion 416 based on elastic force of the coil spring 424 and enters the hole of the fixing portion 414. As a result, the fixing portion 414 is locked in a posture in which the fixing portion 414 linearly extends with respect to the base portion 416. In this specification, this state is called a closed state.

Basically, the coronary-artery support mechanism 300 also has the same structure as the graft support mechanism 400. That is, in the coronary-artery support mechanism 300, when the fixing portion 314 urged by a leaf spring is contact with a pin 320 protruding from the base portion 316, the fixing portion 314 is locked in a posture in which the fixing portion 314 is inclined with respect to the base portion 316. That is, the coronary-artery support mechanism 300 is in the opened state. When the pin 320 is drawn into the base portion 316 from this state, so that the fixing portion 314 is unlocked, the fixing portion 314 swivels on the shaft 318 and gets still in a posture in which the fixing portion 314 linearly extends to the base portion 316. Then, the pin 320 protrudes from the base portion 316 to enter the hole of the fixing portion 314, causing the fixing portion 314 to be locked in a posture in which the fixing portion 314 linearly extends with respect to the base portion. That is, the coronary-artery support mechanism 300 enters the closed state.

As one of differences between the graft support mechanism 400 and the coronary-artery support mechanism 300, since the graft supports 412 of the graft support mechanism 400 are inserted into the graft from its end face, the graft supports 412 are straight, whereas since the coronary-artery supports 312 of the coronary-artery support mechanism 300 are stuck into the coronary artery from a side surface of the coronary artery, root portions of the coronary-artery supports 312 are bent downward, and portions of the coronary-artery supports 312 that are actually inserted into the coronary artery deviate from a position fixed to the fixing portion 314 in the downward direction.

Figure 14:
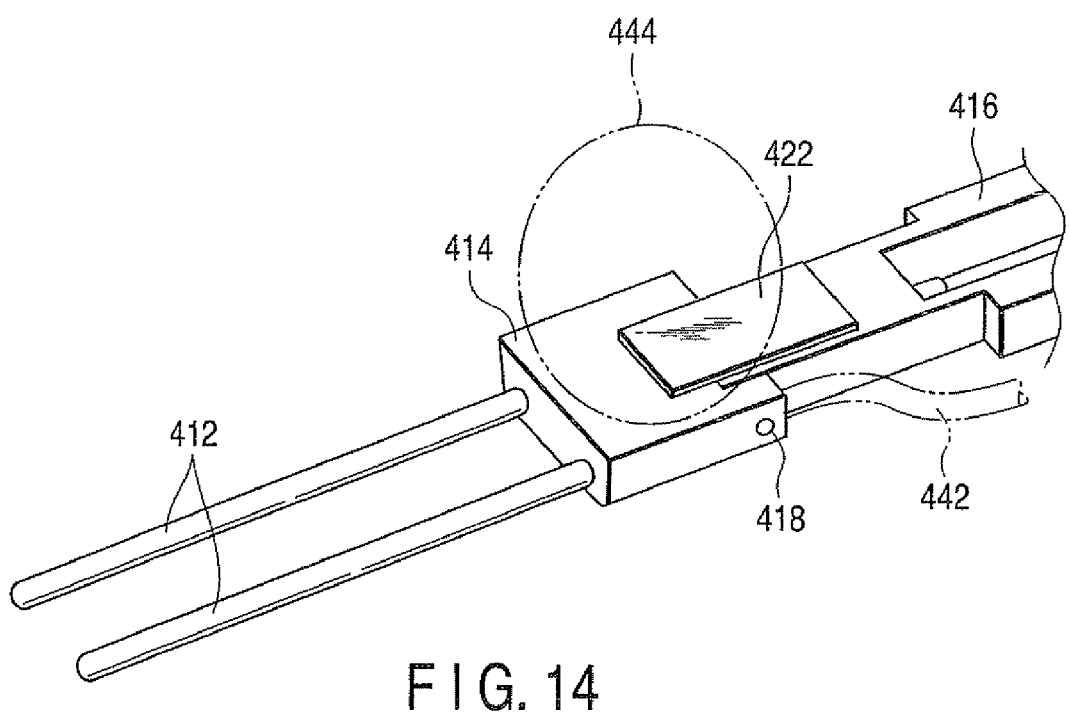
FIG. 14 schematically shows a graft holding mechanism provided to the graft support mechanism.

Furthermore, as another difference from the coronary-artery support mechanism 300, the graft support mechanism 400 has a graft holding mechanism to hold the graft. Therefore, as shown in FIG. 14, a tube 442 through which a gas is supplied is connected with the fixing portion 414. For example, a suction hole that is opened in a surface contacting with the graft is provided in the fixing portion 414. The suction hole is connected with a negative-pressure source through the tube 442. In this configuration, a pressure in the tube 442 is reduced by the negative-pressure source, causing the graft to be adsorbed to the fixing portion 414, so that the graft is held by the fixing portion 414. As another example, a balloon 444 is disposed to the fixing portion. The balloon 444 is connected with a gas supply source through the tube 442. In this configuration, a gas is supplied to the balloon 444 from the gas supply source, inflating the balloon in the graft, so that the graft is held by the fixing portion 414.

An operation of inosculating the coronary artery and the graft with the staple 10 by using the hollow tissue inosculation apparatus 100 will now be described hereinafter with reference to FIGS. 15 to 51.

Figure 15:
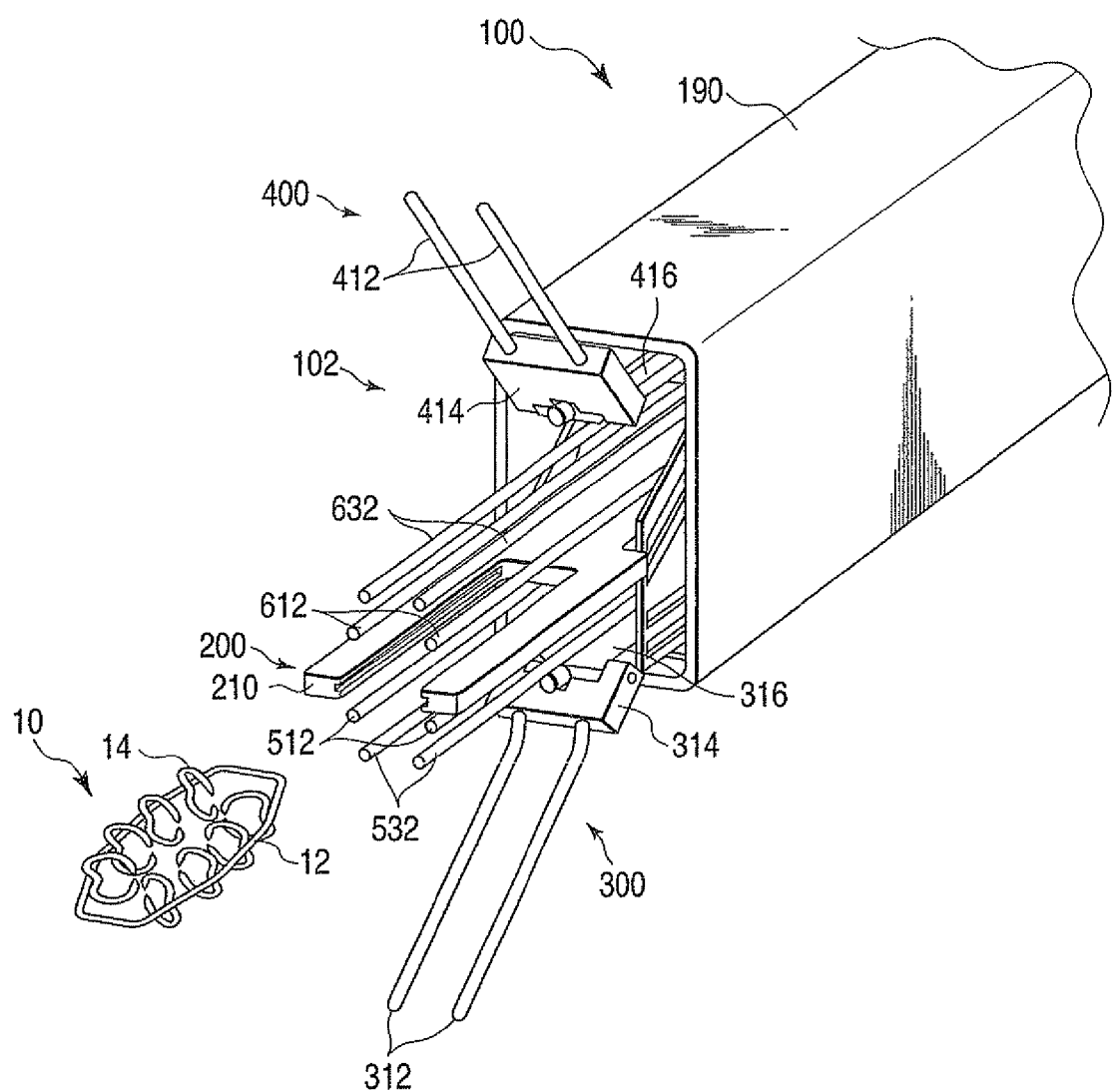
FIG. 15 shows the staple in the natural state and the treatment unit of the hollow tissue inosculation apparatus.

As shown in FIG. 15, the hollow tissue inosculation apparatus 100 is adjusted to a state where the coronary-artery support mechanism 300 and the graft support mechanism 400 are opened. Moreover, the outer pillars 512, the inner pillars 532, the outer pillars 612, and the inner pillars 632 are moved closer to the staple holder 200 in advance. The staple 10 is arranged in front of the staple holder 200 so that the ring member 12 is aligned in the grooves 212 of the staple holding members 210.

Then, the ring member 12 is pushed into a space between the grooves 212 of the staple holding members 210, so that the staple 10 is attached to the staple holder 200. At this time, the ring member 12 is slid along the grooves 212 of the staple holding members 210 while being squashed. As a result, the staple 10 is deformed into the deformed state depicted in FIG. 2 from the natural state shown in FIG. 1. Additionally, the outer pillars 512, the inner pillars 532, the outer pillars 612, and the inner pillars 632 are moved away from the staple holder 200 to straighten the staple pins 14 of the staple 10.

Figure 16:
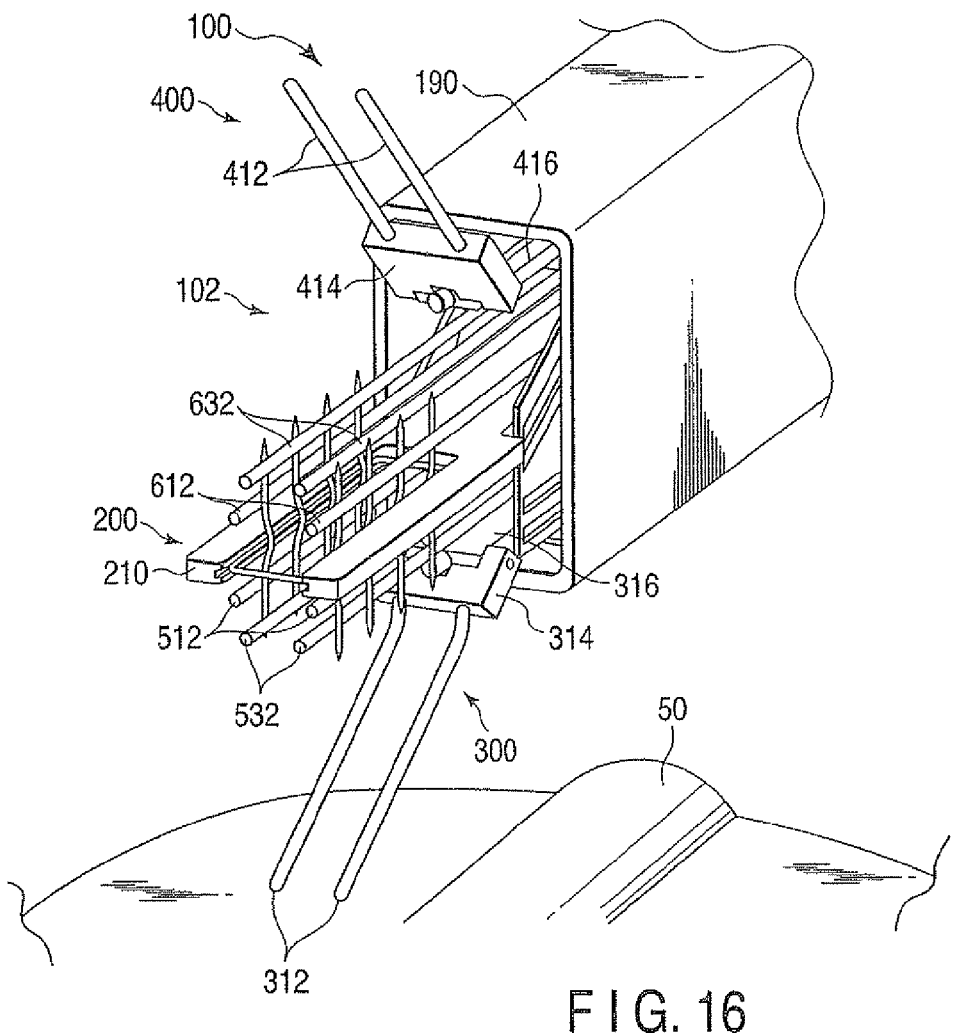
FIG. 16 is a perspective view of the treatment unit of the hollow tissue inosculation apparatus into which the staple is inserted.
Figure 17:
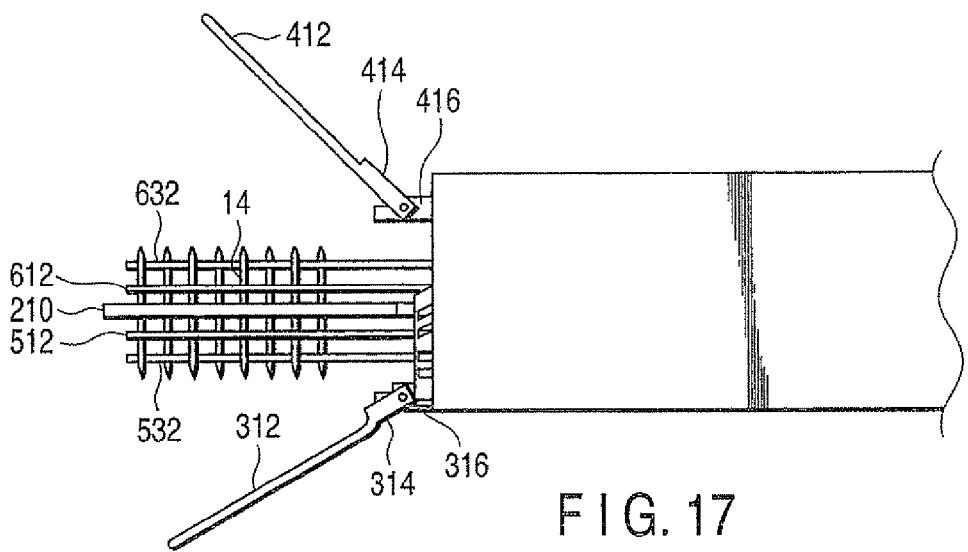
FIG. 17 is a side view of the treatment unit depicted in FIG. 16.

FIGS. 16 and 17 show a state where the staple 10 is inserted into the staple holder 200 and the staple pins 14 are straightened.

Figure 19:
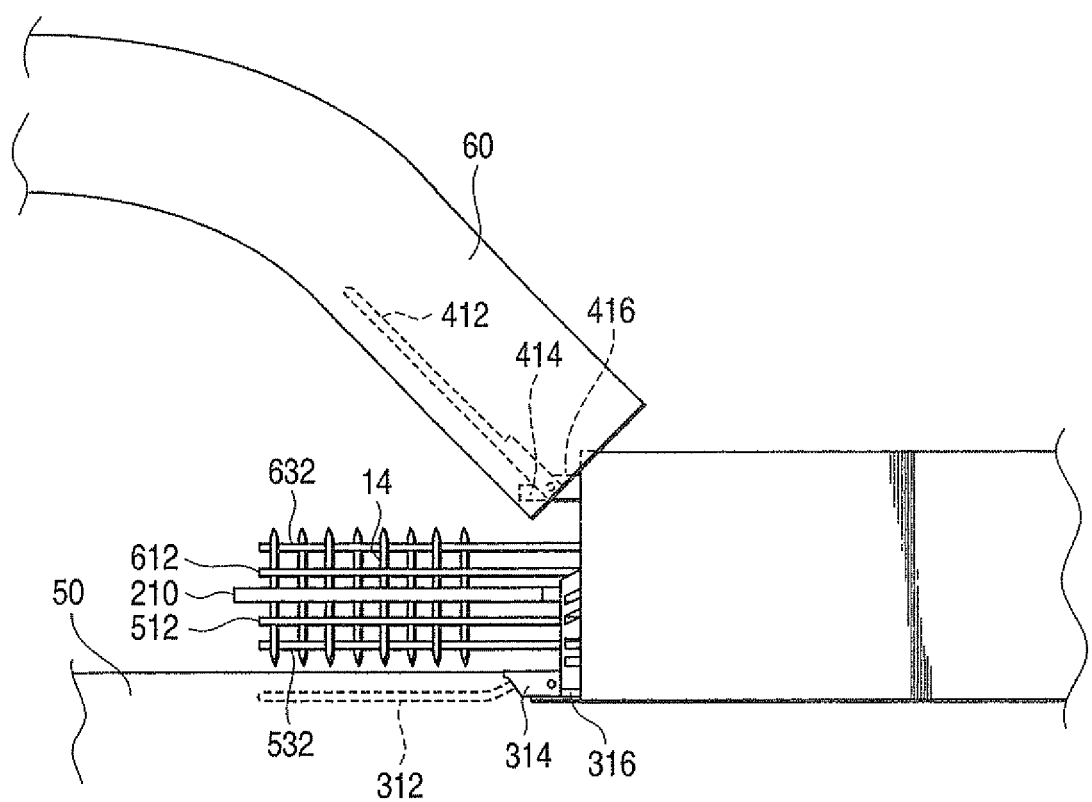
FIG. 19 is a side view of the treatment unit depicted in FIG. 18.

Subsequently, as shown in FIGS. 18 and 19, the coronary-artery supports 312 are stuck into a coronary artery 50 and the coronary-artery support mechanism 300 is then closed, and the graft supports 412 and the fixing portion 414 are inserted into a graft 60 from its end face. Further, the graft holding mechanism is used to hold the graft 60 on the fixing portion 414.

Figure 22:
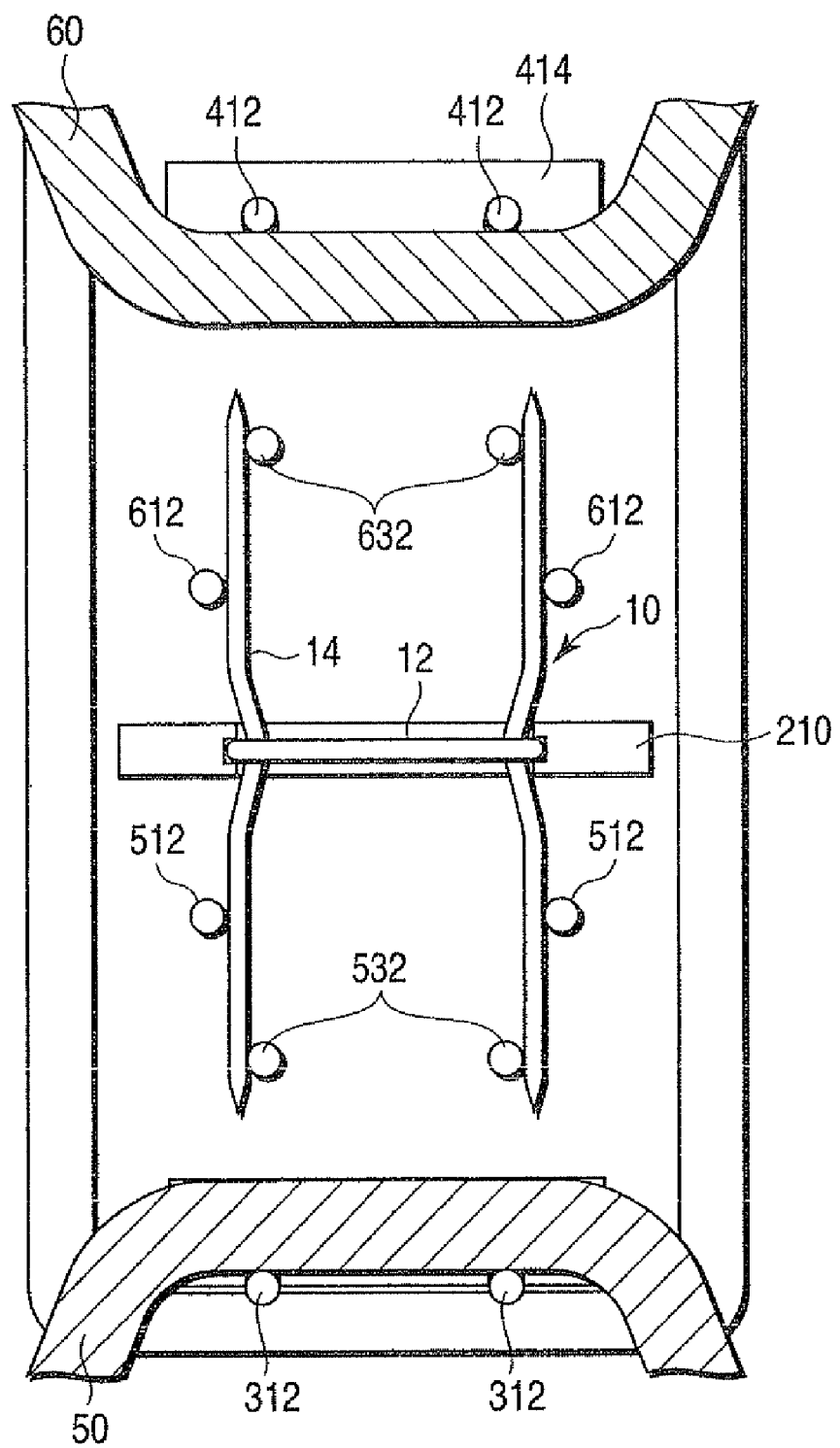
FIG. 22 is a front view of the treatment unit depicted in FIG. 20.

Then, as shown in FIGS. 20 to 22, the graft support mechanism 400 is closed. As a result, the coronary artery 50 and the graft 60 are arranged in substantially parallel to each other.

Figure 23:
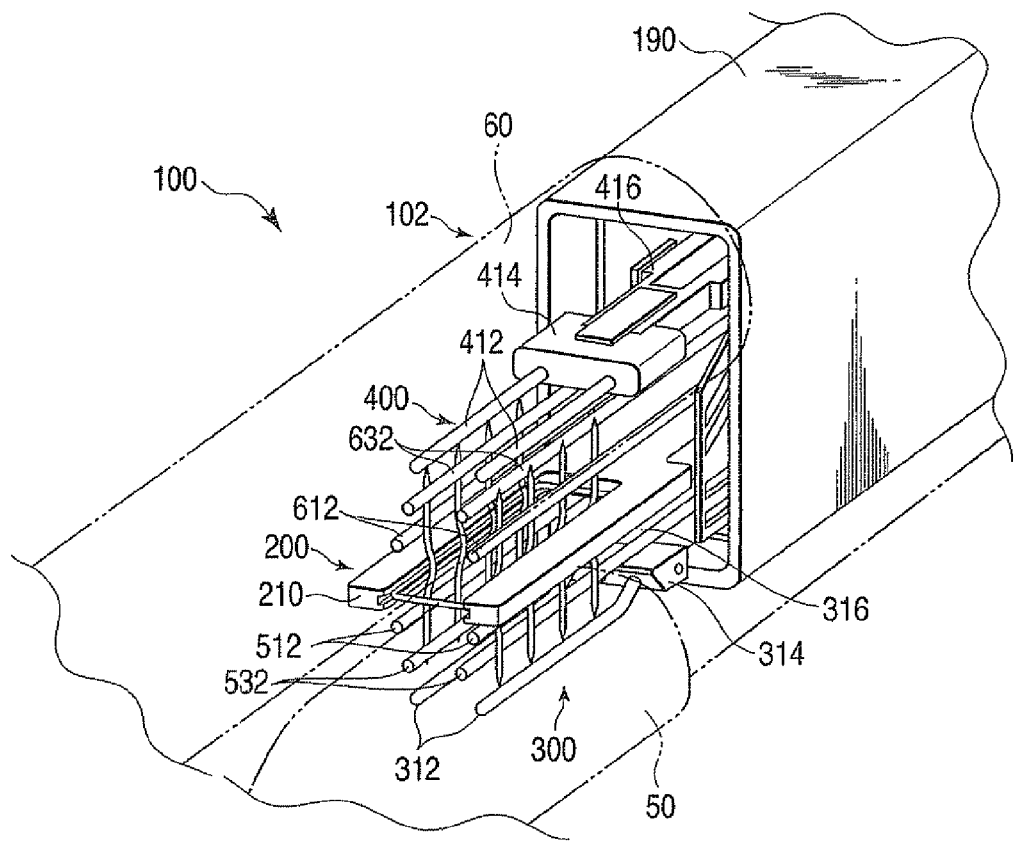
FIG. 23 is a perspective view of the treatment unit in which end portions of the staple pins are stuck in the graft and the coronary artery.
Figure 24:
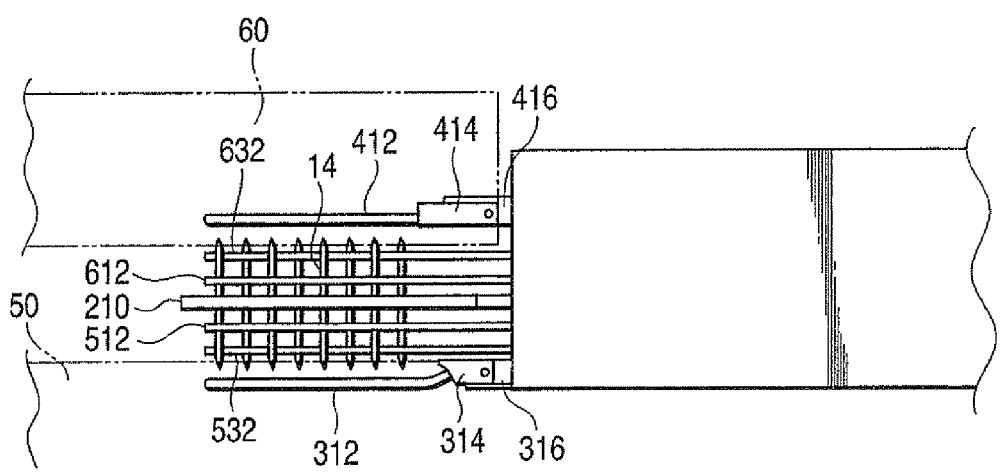
FIG. 24 is a side view of the treatment unit depicted in FIG. 23.
Figure 25:
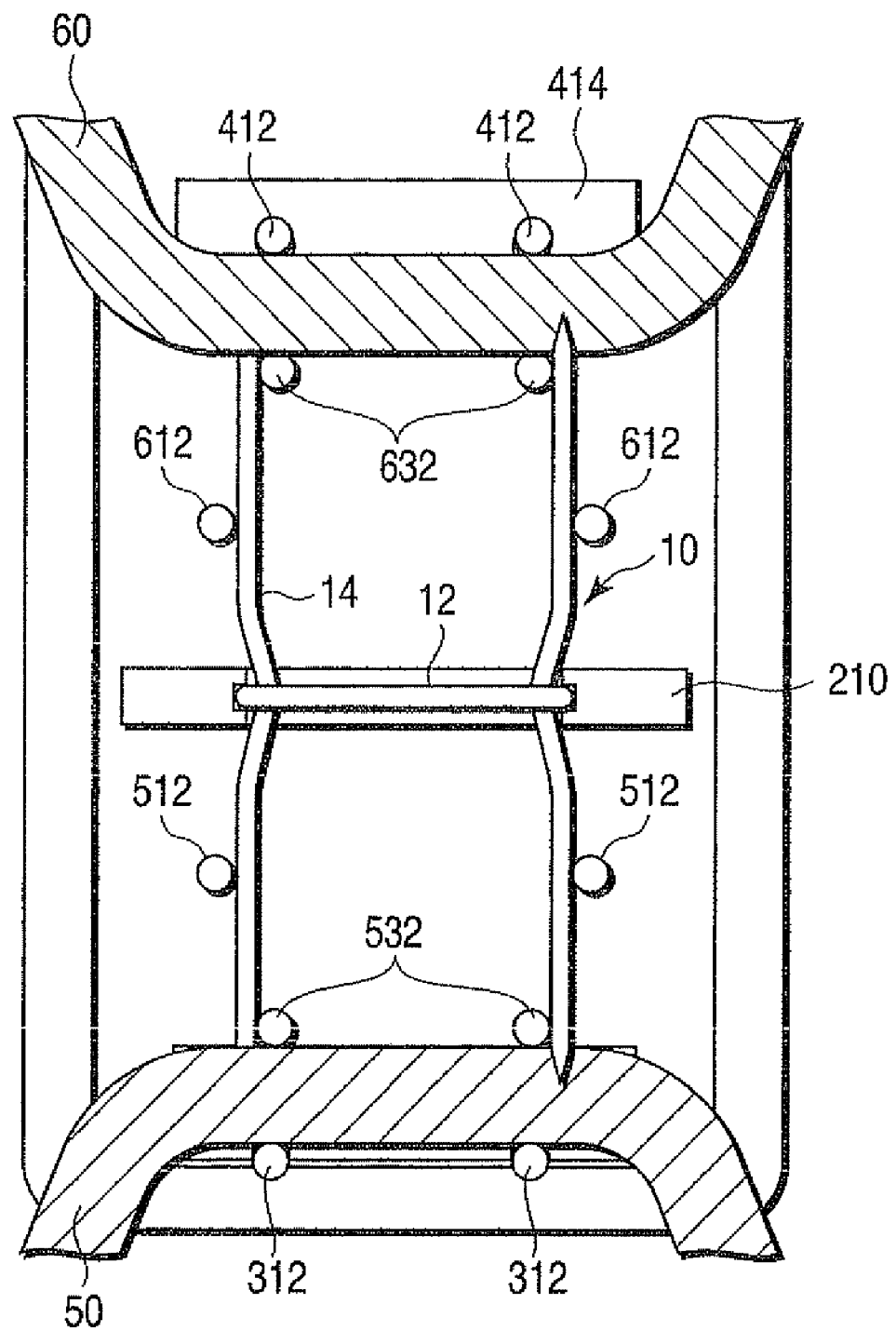
FIG. 25 is a front view of the treatment unit depicted in FIG. 23.

Subsequently, as shown in FIGS. 23 to 25, the graft support mechanism 400 and the staple holder 200 are moved closer to the coronary-artery support mechanism 300 to narrow gaps of the graft support mechanism 400 and the coronary-artery support mechanism 300 with respect to the staple holder 200, so that end portions of the staple pins 14 of the staple 10 are stuck into the coronary artery 50 and the graft 60. The coronary-artery supports 312 and the graft supports 412 respectively support the coronary artery 50 and the graft 60 when the staple pins 14 of the staple 10 are stuck into the coronary artery 50 and the graft 60. Stick of the staple pins 14 is moderately performed so that the staple pins 14 do not penetrate through the coronary artery 50 and the graft 60.

Figure 26:
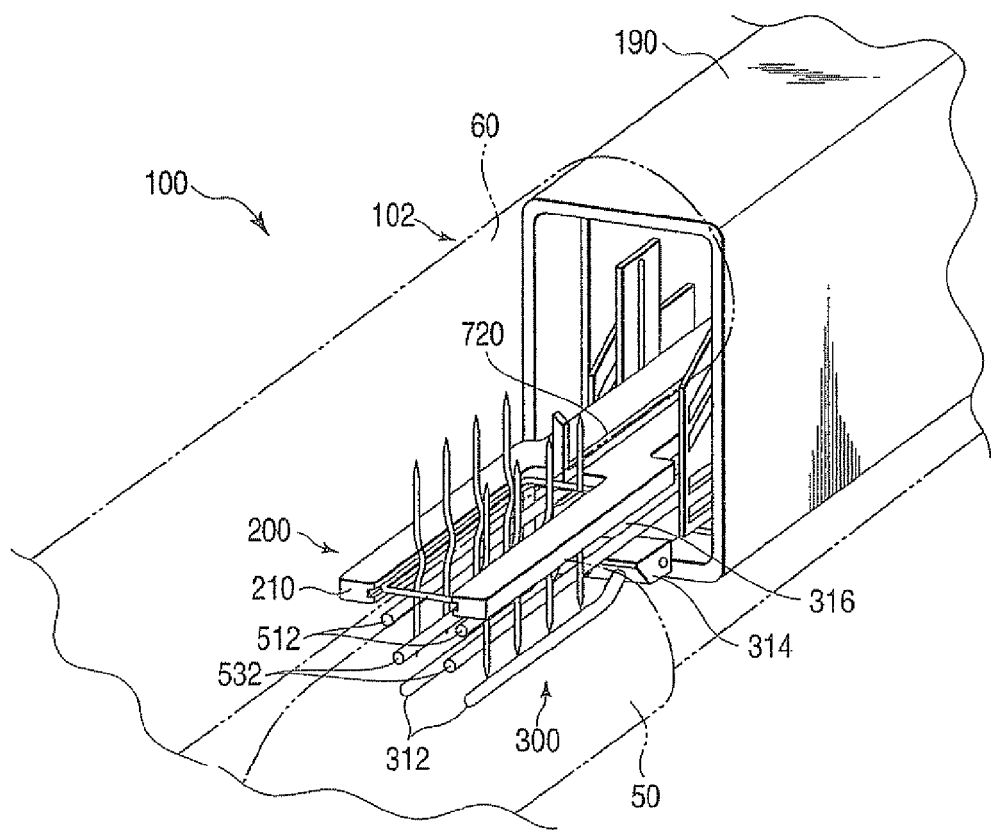
FIG. 26 is a perspective view of the treatment unit in which blades of cutters are arranged between the graft and the coronary artery.
Figure 27:
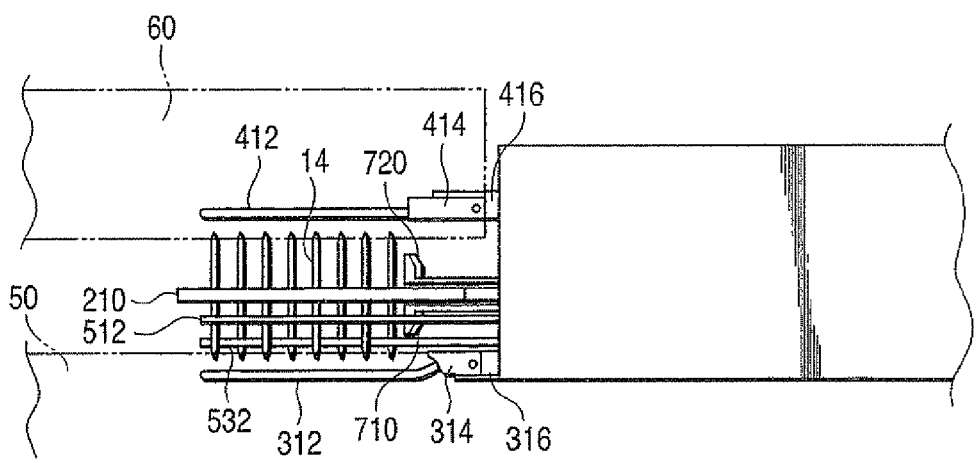
FIG. 27 is a side view of the treatment unit depicted in FIG. 26.
Figure 28:
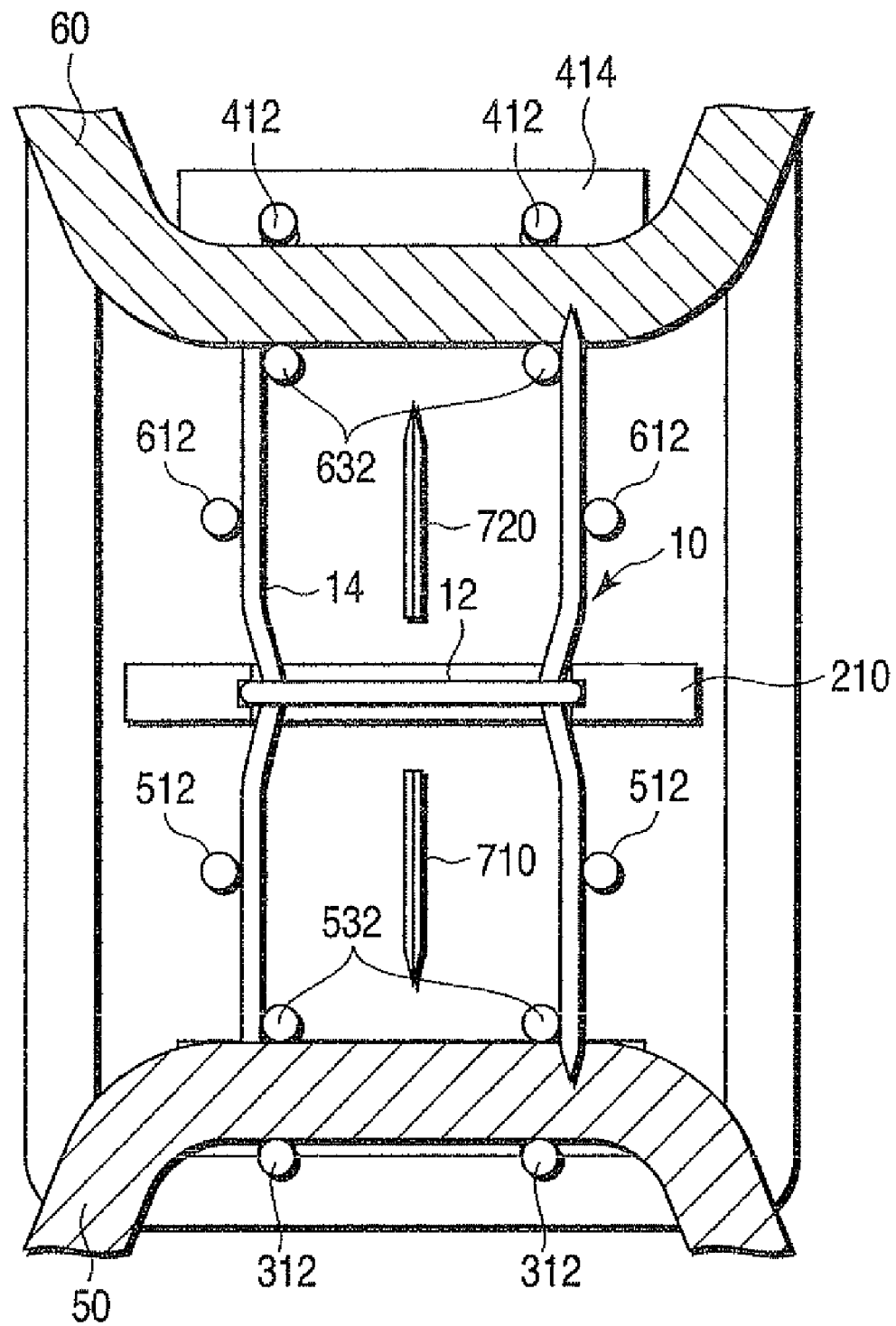
FIG. 28 is a front view of the treatment unit depicted in FIG. 26.

Subsequently, as shown in FIGS. 26 to 28, the cutters 710 and 720 of the incision mechanism 700 are moved in the forward direction to arrange the blades 712 and 722 at the back of the inside of the ring member 12 of the staple 10. In FIGS. 26 and 27, the outer pillars 612 and the inner pillars 632 are omitted to facilitate visualization of the cutter 710.

Figure 29:
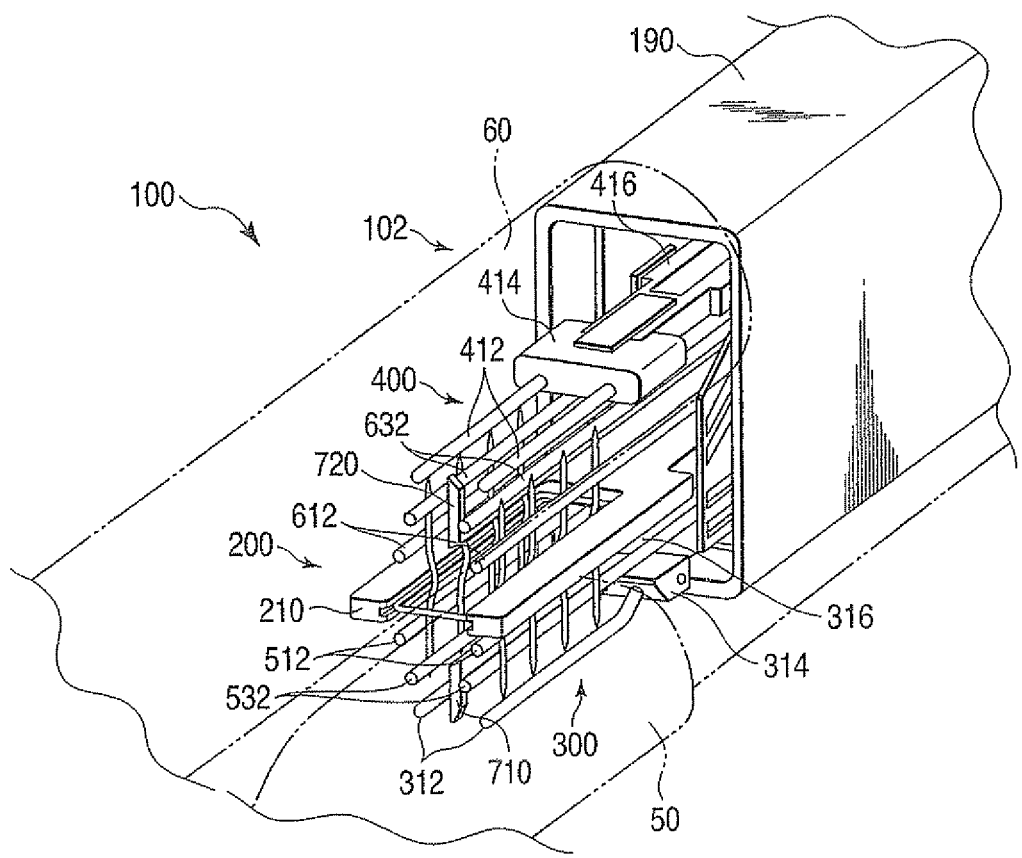
FIG. 29 is a perspective view of the treatment unit in which incision of the graft and the coronary artery is finished.
Figure 30:
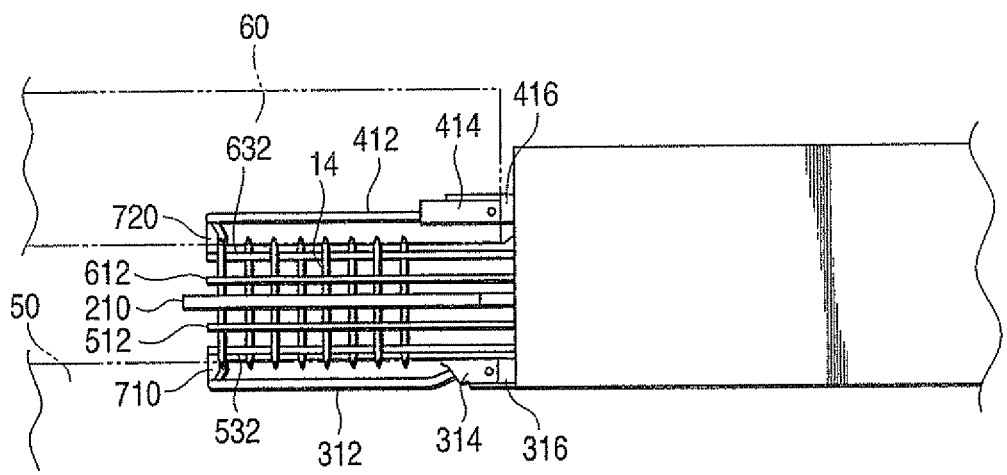
FIG. 30 is a side view of the treatment unit depicted in FIG. 29.
Figure 31:
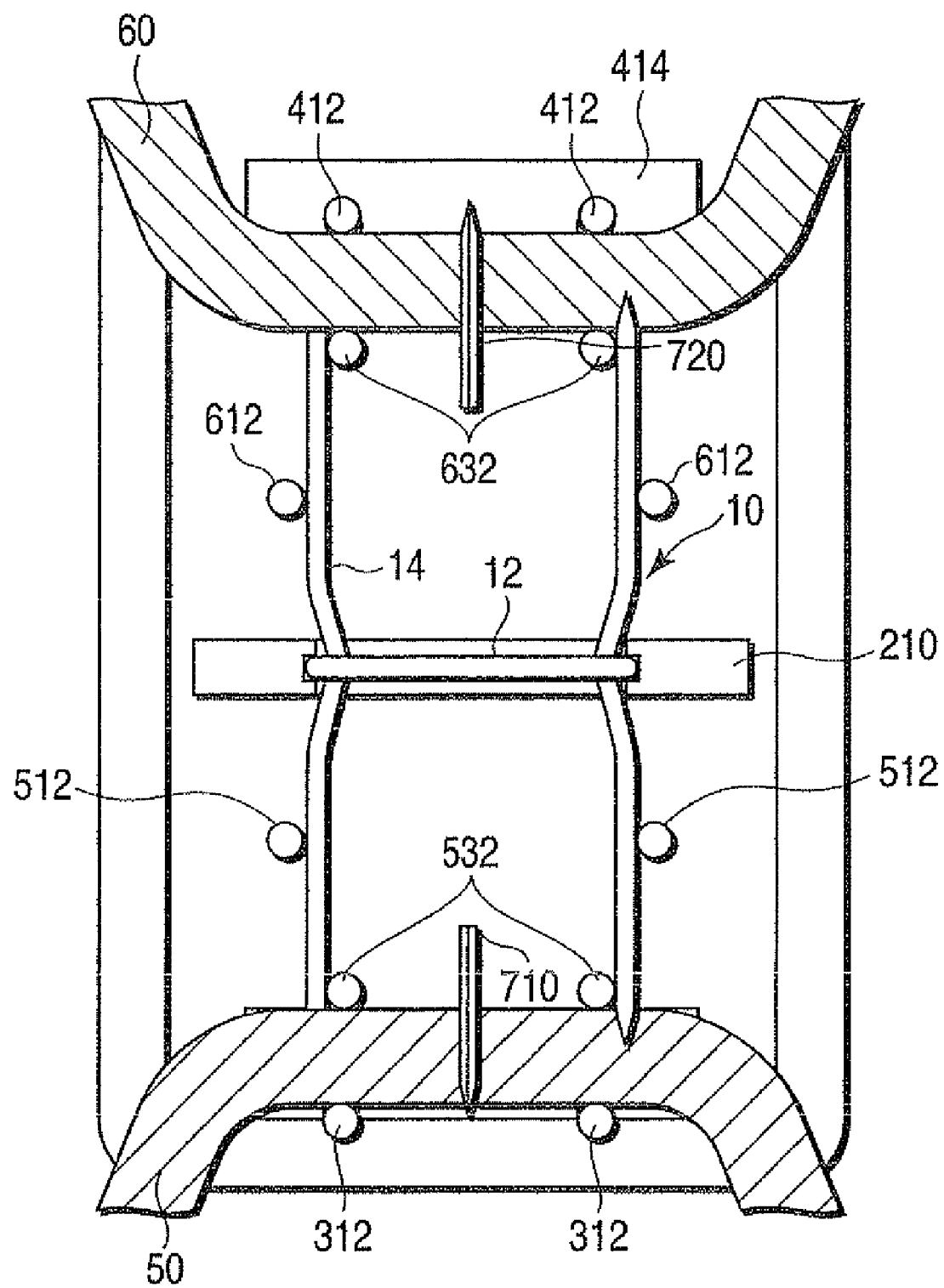
FIG. 31 is a front view of the treatment unit depicted in FIG. 29.

Then, the cutter 710 is moved in the downward direction to cause the blade 712 to stick through the coronary artery 50, and the cutter 720 is moved in the upward direction to cause the blade 722 to stick through the graft 60. Thereafter, both the cutter 710 and the cutter 720 are moved in the forward direction to incise the coronary artery 50 and the graft 60, respectively. FIGS. 29 to 31 show a state when incision is finished.

Although FIGS. 26 to 28 show an example of incising the coronary artery 50 and the graft 60 at the same position for the same length, but the position and the length for incision of the coronary artery 50 may be different from those of the graft 60. That is, the coronary artery 50 and the graft 60 may be incised at the same position for different lengths, or they may be incised at different positions for the same length or at different positions for different lengths.

As explained above, according to the incision mechanism 700, the blades 712 and 722 of the cutters 710 and 720 are arranged between the coronary artery 50 and the graft 60 to incise the coronary artery 50 and the graft 60 from the outer side. Further, the staple holder 200 holds the staple 10 in such a manner that the blades 712 and 722 of the cutters 710 and 720 do not come into contact with the staple 10. Specifically, the staple holder 200 holds the staple 10 so that the blades 712 and 722 of the cutters 710 and 720 are placed at the inside of the ring member 12. Further, the staple holder 200 functions as an expansion preventing mechanism to prevent the ring member 12 of the staple 10 from expanding generally while the staple 10 is held, at least while the coronary artery 50 and the graft 60 are incised.

Figure 32:
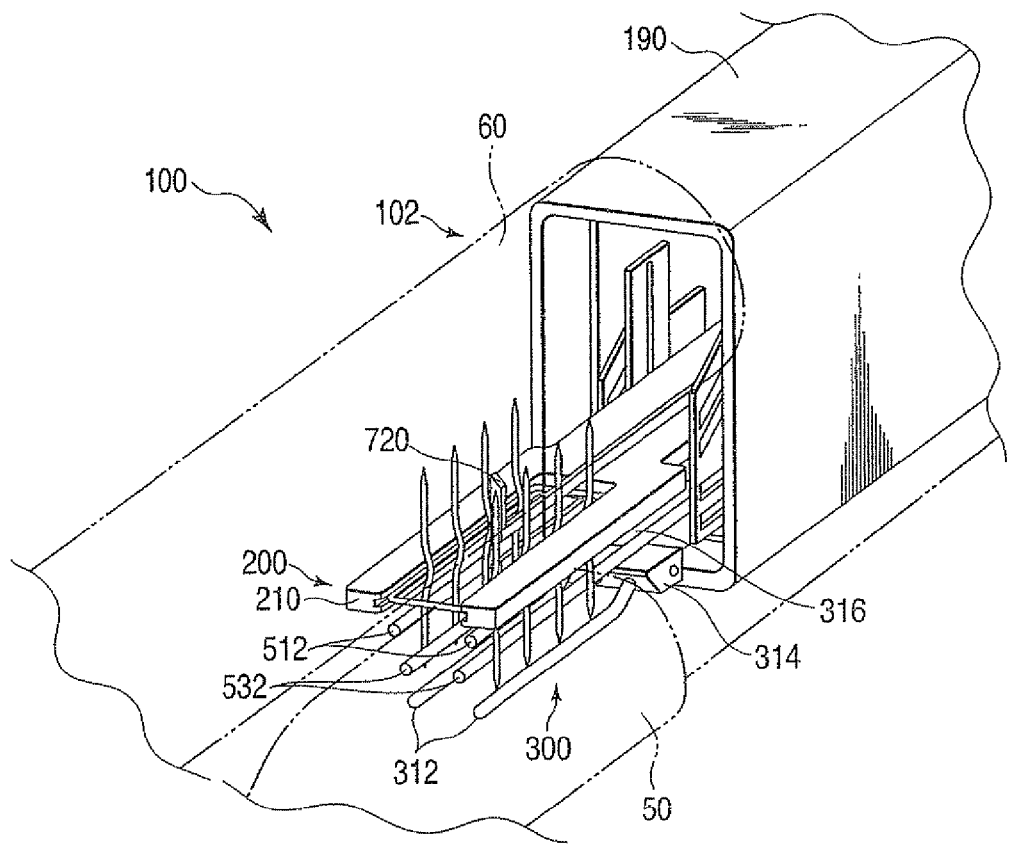
FIG. 32 is a perspective view of the treatment unit while the cutters are retracted into a housing.
Figure 33:
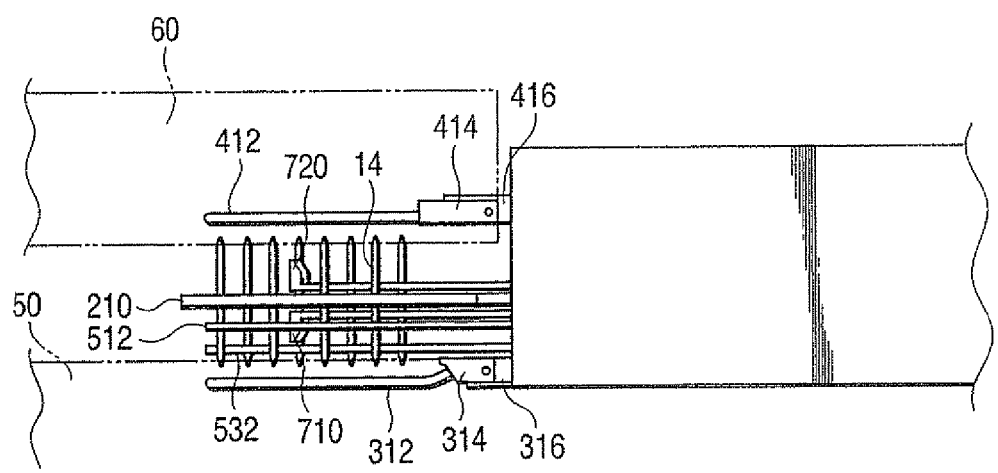
FIG. 33 is a side view of the treatment unit depicted in FIG. 32.

Then, the cutter 710 is moved in the upward direction to pull out the blade 712 from the coronary artery 50, and the cutter 720 is moved in the downward direction to pull out the blade 722 from the graft 60. Thereafter, both the cutters 710 and 720 are moved in the backward direction to be retracted into the housing 190. FIGS. 32 to 34 show a state while the cutters 710 and 720 are retracted. In FIGS. 32 and 33, the outer pillars 612 and the inner pillars 632 are omitted to facilitate visualization of the cutter 710.

In the hollow tissue inosculation apparatus 100 according to this embodiment, the four wires 852, 862, 872, and 882 connected with the incision mechanism 700 are coupled with different operation knobs of the operation unit 106, respectively. Alternatively, the two wires 852 and 872 are coupled with a common operation knob so that directions of their operations are opposite to each other, and the two wires 862 and 882 are coupled with another common operation knob so that directions of their operations are opposite to each other. The operation knob coupled with the wires 852 and 862 and the operation knob coupled with the wires 872 and 882 may be individually operated, enabling the coronary artery 50 and the graft 60 to be incised at different positions or for different lengths, or at different positions for different lengths.

Furthermore, if the hollow tissue inosculation apparatus 100 is always used for a purpose of incising the coronary artery 50 and the graft 60 at the same position for different lengths, the two wires 852 and 872 may be coupled with a common operation knob of the operation unit 106 and the two wires 862 and 882 may be coupled with another common operation knob of the operation unit 106 in the hollow tissue inosculation apparatus 100. Alternatively, the pair of wires 852 and 872 and the pair of wires 862 and 882 may be coupled with a common operation knob in such a manner that directions of operations of the respective pairs are opposite to each other.

Figure 35:
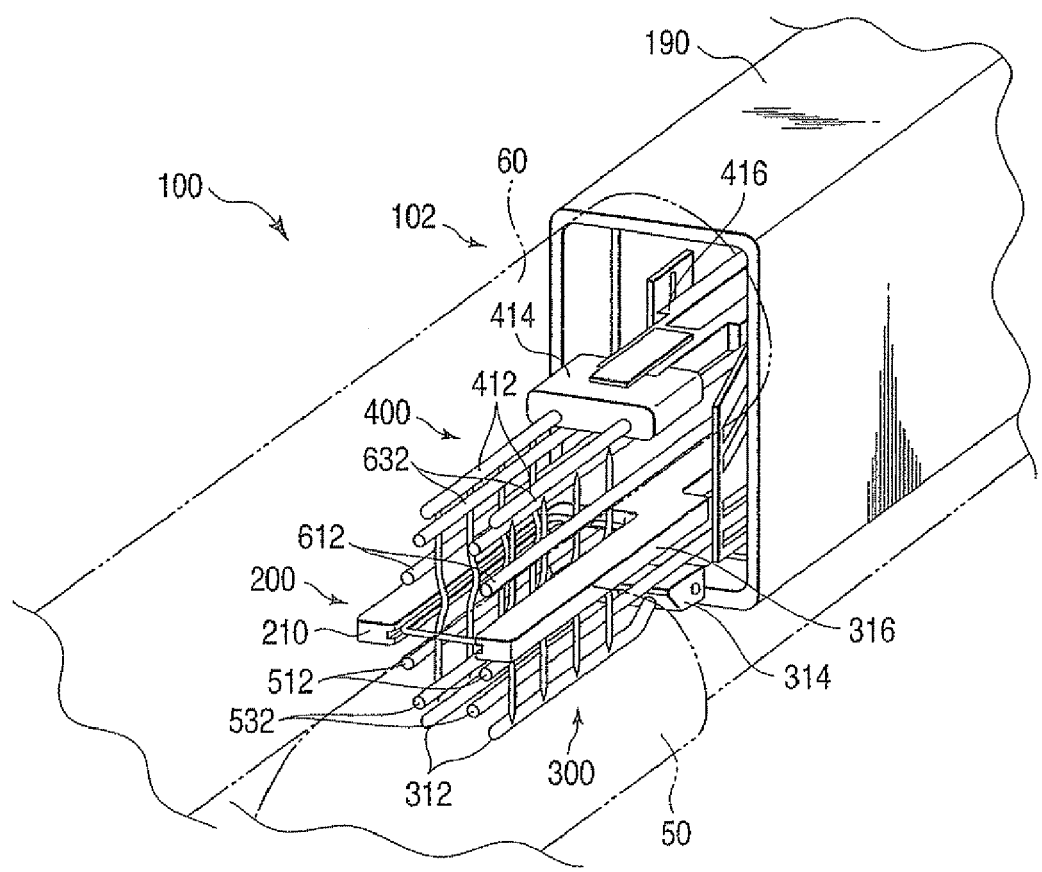
FIG. 35 is a perspective view of the treatment unit in which staple pins are further stuck into the graft and the coronary artery.
Figure 36:
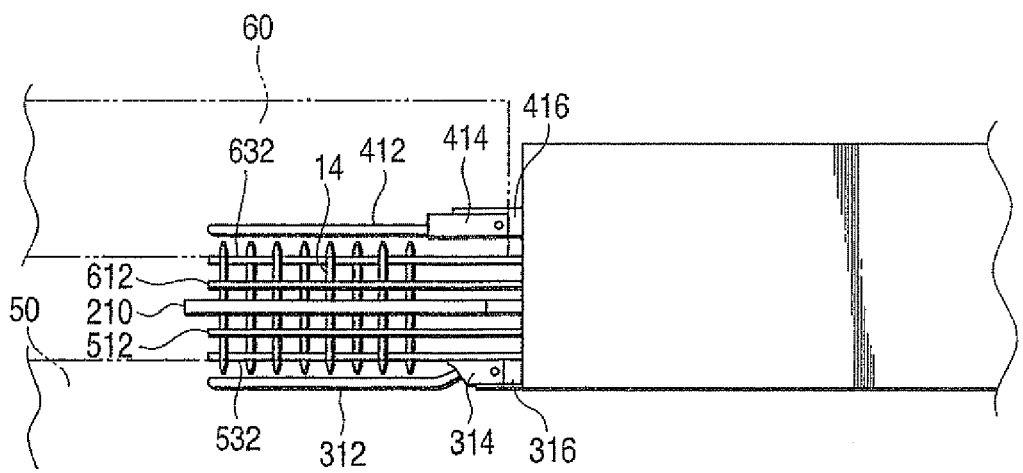
FIG. 36 is a side view of the treatment unit depicted in FIG. 35.
Figure 37:
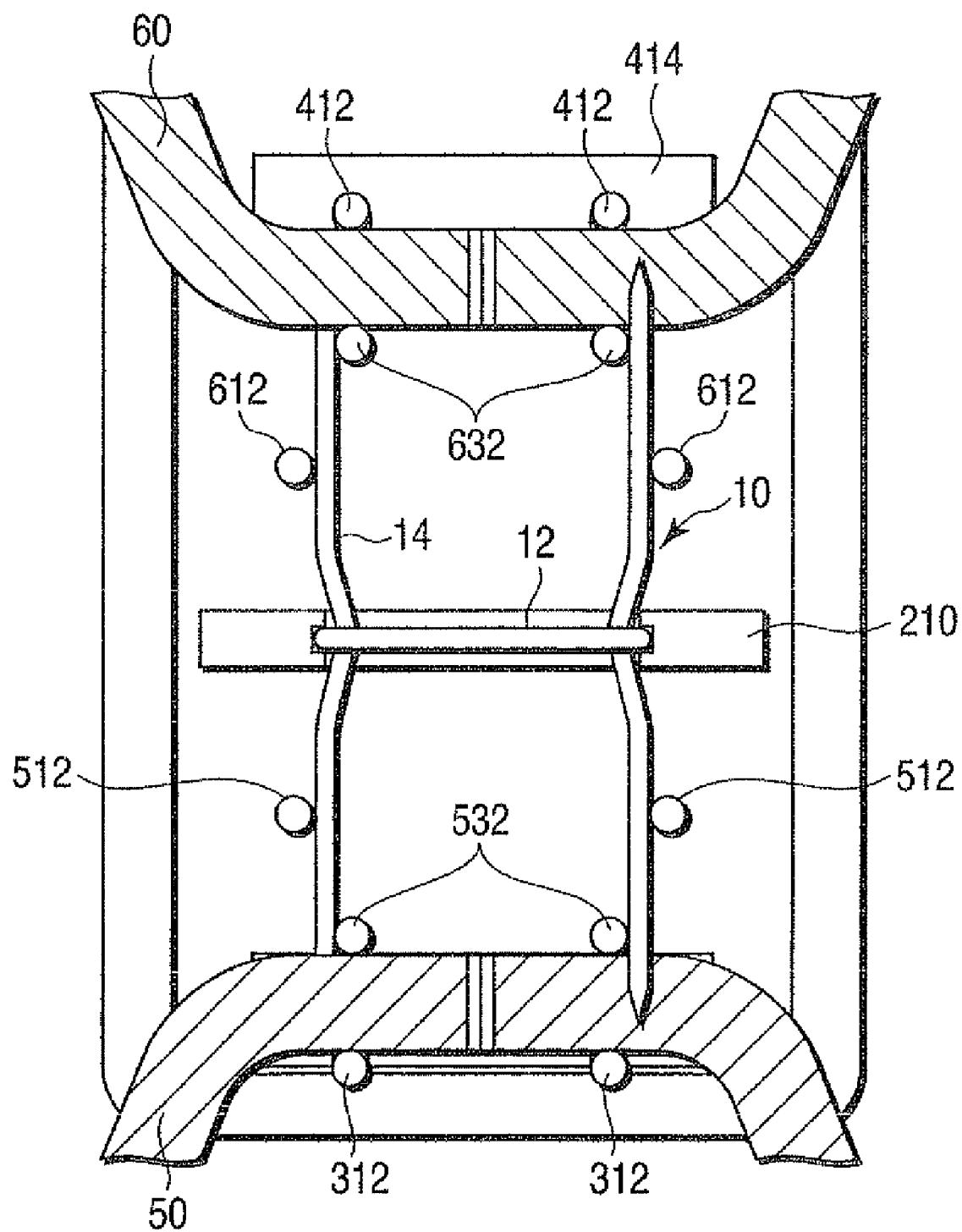
FIG. 37 is a front view of the treatment unit depicted in FIG. 35.
Figure 38:
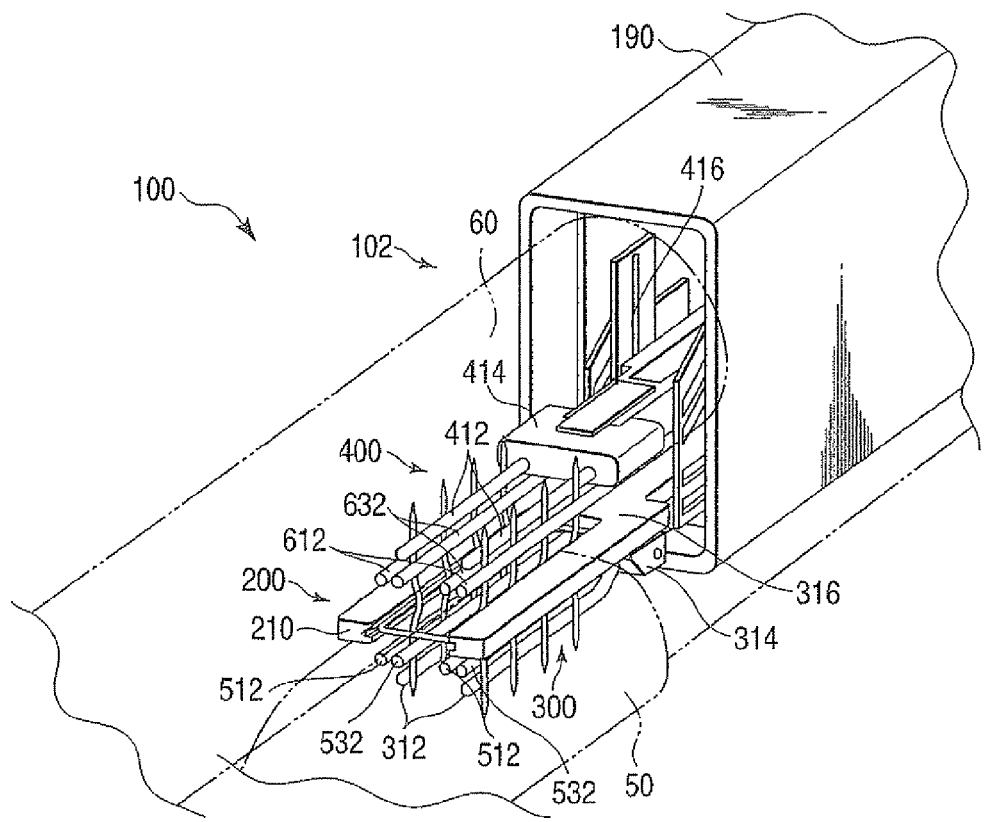
FIG. 38 is a perspective view of the treatment unit in which the end portions of the staple pins have penetrated through the graft and the coronary artery.
Figure 39:
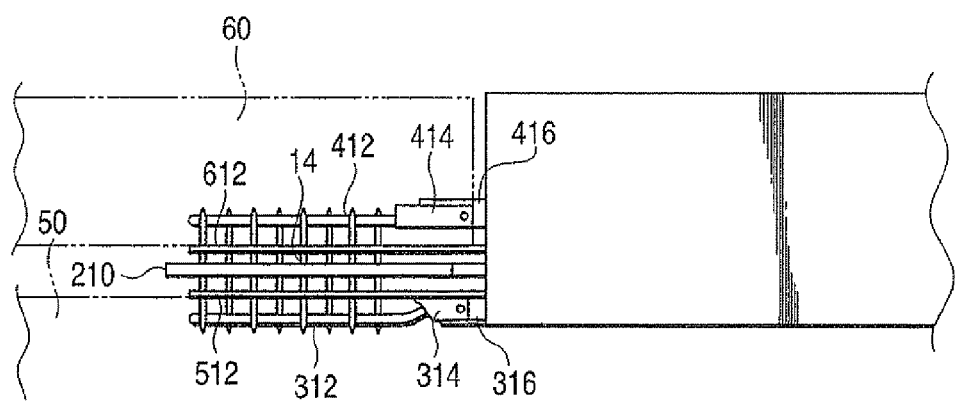
FIG. 39 is a side view of the treatment unit depicted in FIG. 38.

Then, as shown in FIGS. 35 to 37, the graft support mechanism 400 and the staple holder 200 are further moved closer to the coronary-artery support mechanism 300 to narrow gaps of the graft support mechanism 400 and the coronary-artery support mechanism 300 with respect to the staple holder 200. At this time, the inner pillars 632 and the inner pillars 532 move closer to the staple holder 200 in cooperation with the graft support mechanism 400 and the coronary-artery support mechanism 300, but both the outer pillars 612 and the outer pillars 512 do not move with respect to the staple holder 200. The graft support mechanism 400 and the coronary-artery support mechanism 300 are moved closer to the staple holder 200 in this manner, causing the end portions of the staple pins 14 of the staple 10 to penetrate through the coronary artery 50 and the graft 60. Meanwhile, the coronary-artery supports 312 and the graft supports 412 support the coronary artery 50 and the graft 60, respectively. Furthermore, contact positions of the coronary-artery supports 312 and the graft supports 412 with the coronary artery 50 and the graft 60 deviate from positions at which the staple pins 14 of the staple 10 penetrate through the coronary artery 50 and the graft 60. FIGS. 38 to 40 show a state where the end portions of the staple pins 14 of the staple 10 penetrate through the coronary artery 50 and the graft 60, respectively.

As shown in FIG. 40, the coronary-artery supports 312 and the graft supports 412 are positioned at the inner side of the end portions of the staple pins 14 having penetrated through the coronary artery 50 and the graft 60, respectively. Therefore, the end portions of the staple pins 14 having penetrated through the coronary artery 50 or the graft 60 are to be restored to the bent state as the natural state, but they come into contact with the coronary-artery supports 312 and the graft supports 412, and the coronary-artery supports 312 and the graft supports 412 obstruct deformation for restoration to the original bent state. That is, in this embodiment, the coronary-artery supports 312 and the graft supports 412 function as suppression members to suppress deformation of the staple pins 14 to the original bent shape thereof, i.e., restoration of the staple pins 14.

Figure 41:
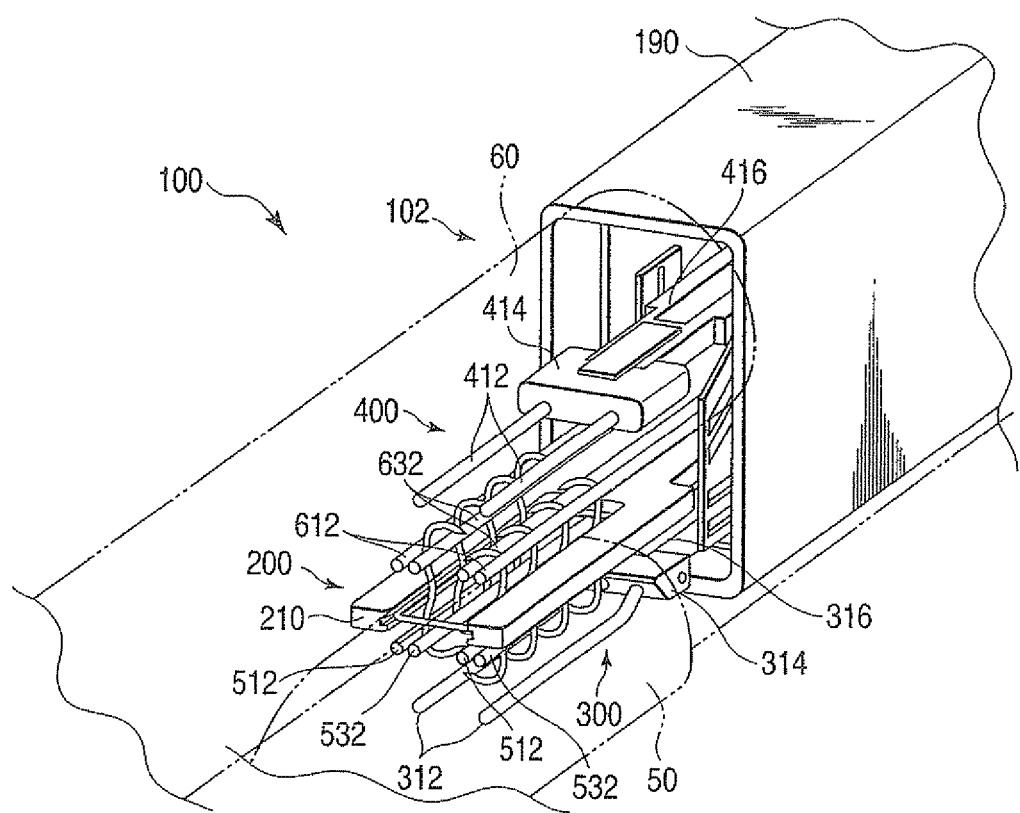
FIG. 41 is a perspective view of the treatment unit in which the graft supports and the coronary-artery supports have been moved away from a staple holder.
Figure 42:
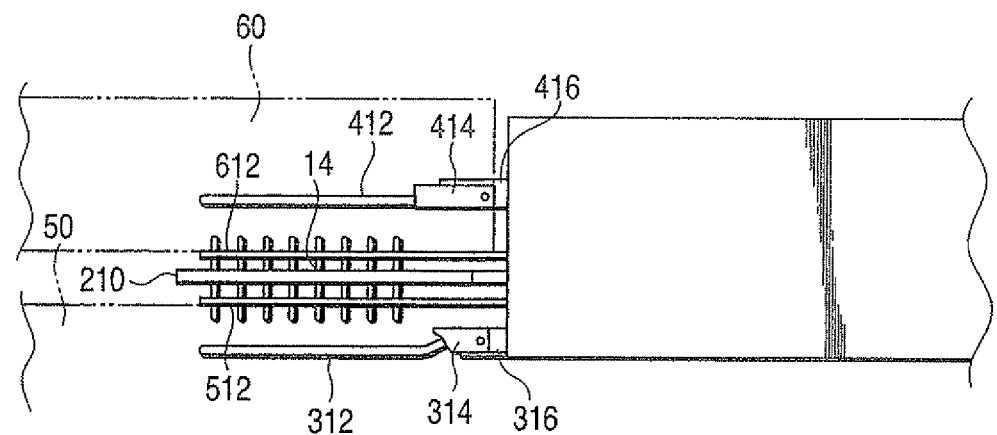
FIG. 42 is a side view of the treatment unit depicted in FIG. 41.
Figure 43:
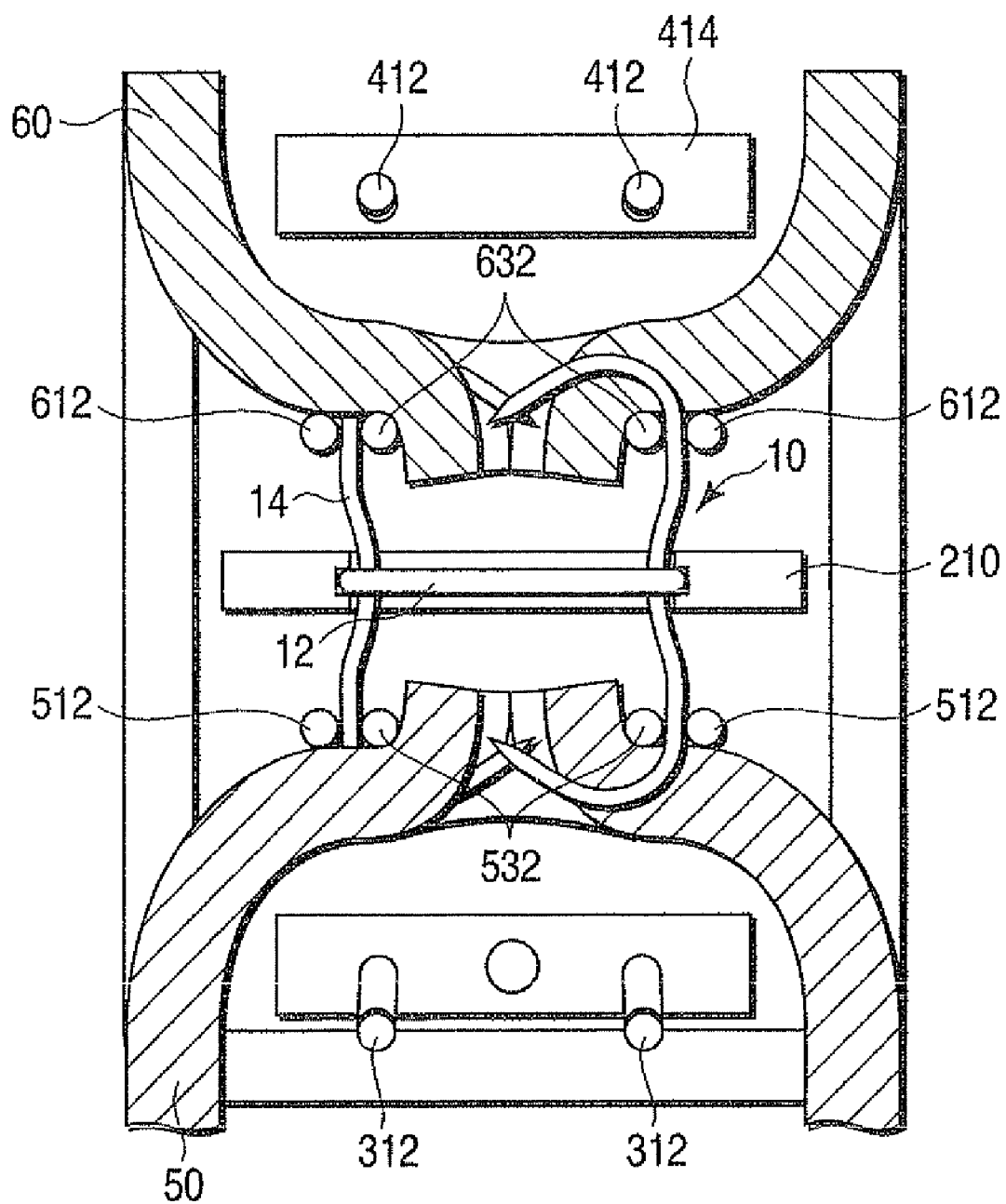
FIG. 43 is a front view of the treatment unit depicted in FIG. 41.

Then, as shown in FIGS. 41 to 43, the graft support mechanism 400 and the staple holder 200 are moved away from the coronary-artery support mechanism 300 to widen the gaps of the graft support mechanism 400 and the coronary-artery support mechanism 300 with respect to the staple holder 200, releasing contact between the end portions of the staple pins 14 having penetrated through the coronary artery 50 and the coronary-artery supports 312 and contact between the end portions of the staple pins 14 having penetrated through the graft 60 and the graft supports 412. As a result, the end portions of the staple pins 14 having penetrated through the coronary artery 50 and the end portions of the staple pins 14 having penetrated through the graft 60 return to the original bent shape. With this deformation of the end portions of the staple pins 14, a part around an incised position of the coronary artery 50 is pulled upward, and a part around an incised position of the graft 60 is pulled downward. As a result, a section of the coronary artery 50 faces a section of the graft 60.

Figure 44:
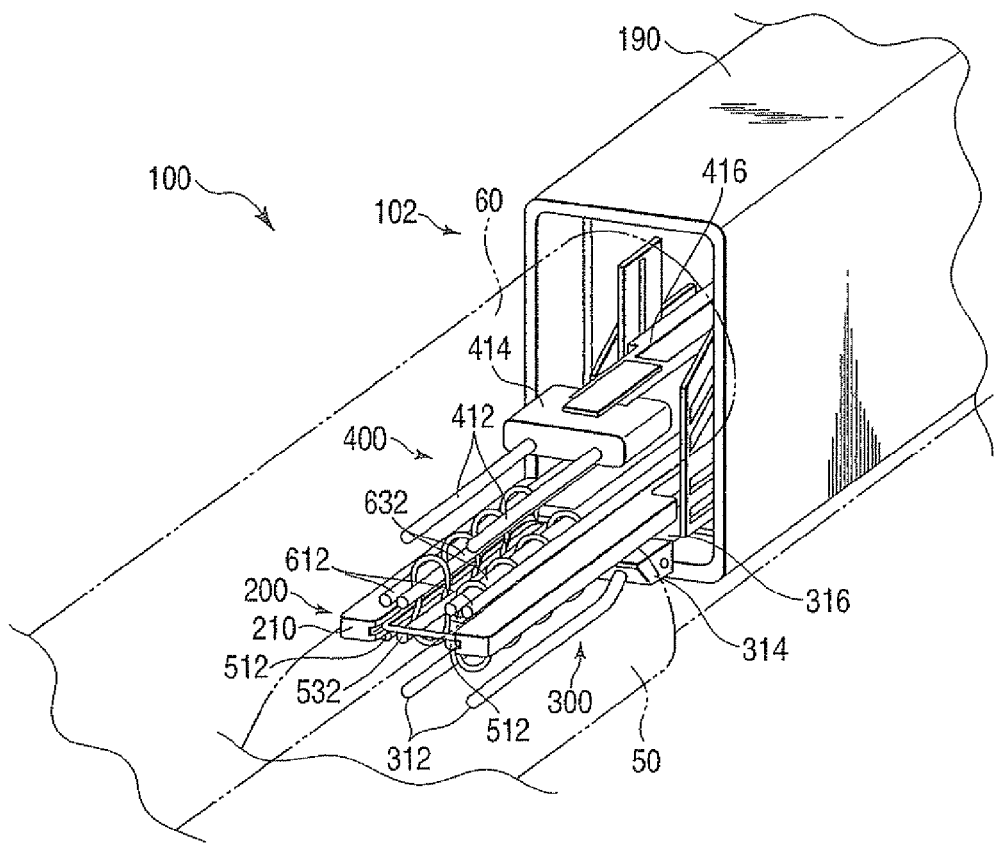
FIG. 44 is a perspective view of the treatment unit in which pillars have been moved closer to the staple holder.
Figure 45:
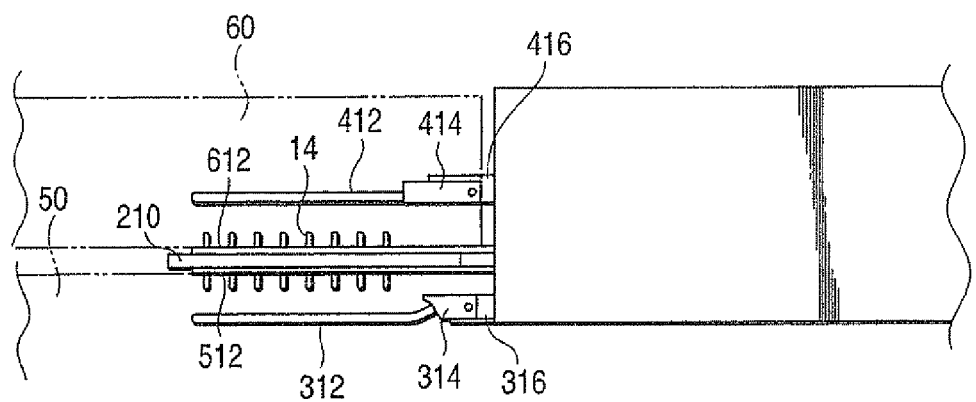
FIG. 45 is a side view of the treatment unit depicted in FIG. 44.

Subsequently, as shown in FIGS. 44 to 46, the outer pillars 512, the inner pillars 532, the outer pillars 612, and the inner pillars 632 are moved closer to the staple holder 200. Consequently, as shown in FIGS. 46, the section of the coronary artery 50 comes into contact with the section of the graft 60, and each staple pin 14 is restored to its original bent shape.

Figure 47:
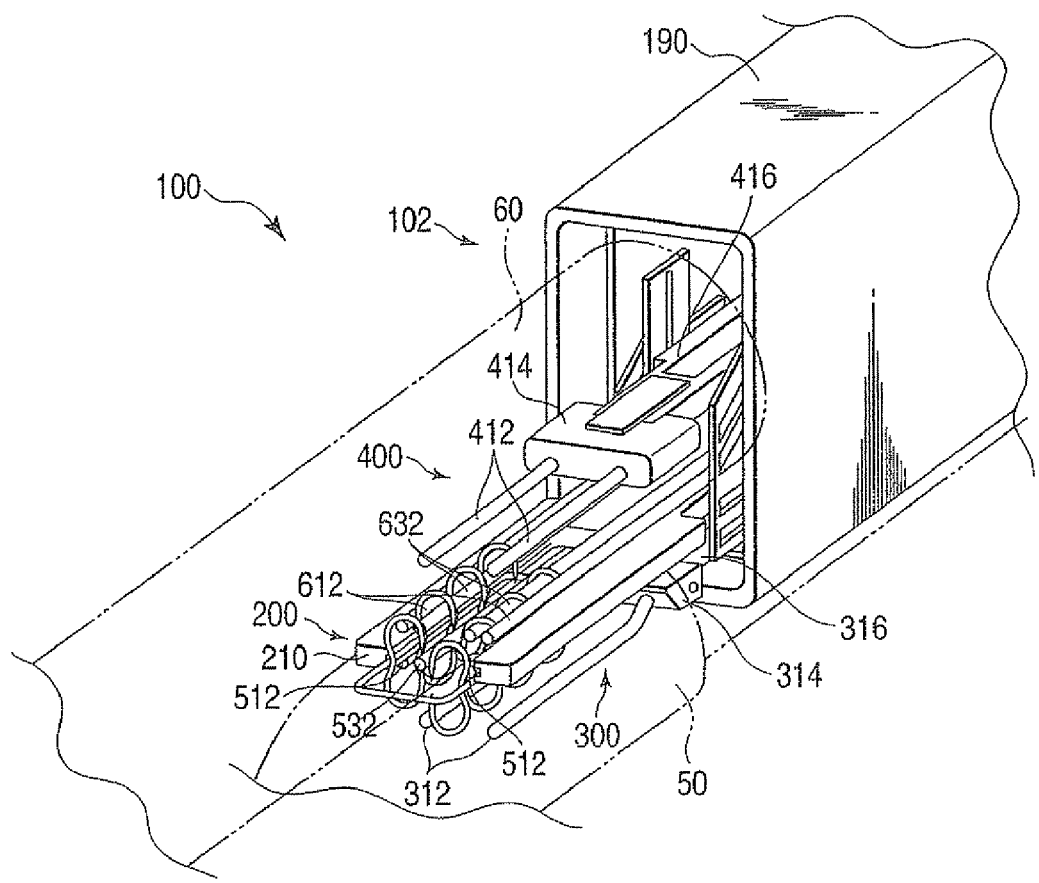
FIG. 47 is a perspective view of the treatment unit that is being removed from the graft and the coronary artery.
Figure 48:
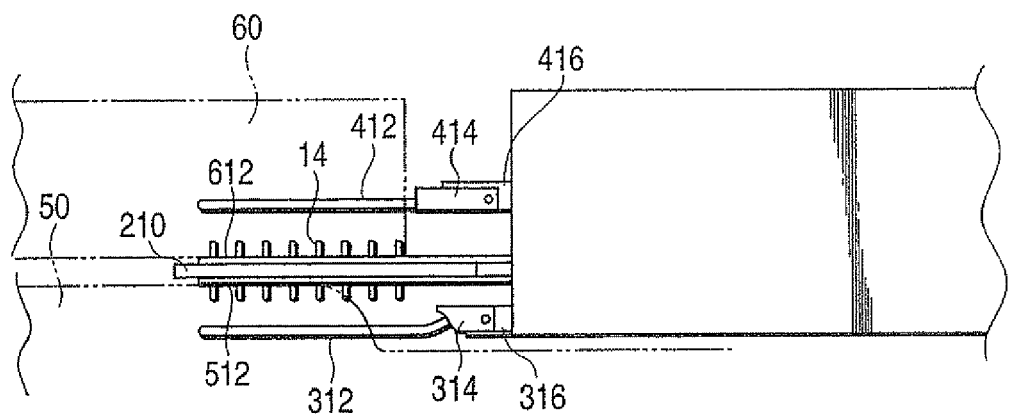
FIG. 48 is a side view of the treatment unit depicted in FIG. 47.
Figure 49:
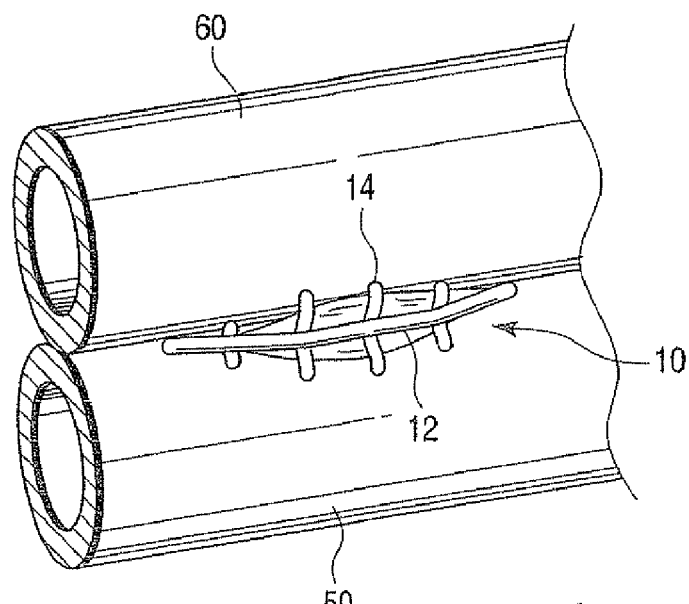
FIG. 49 is a perspective view of the graft and the coronary artery that are inosculated to each other.
Figure 50:
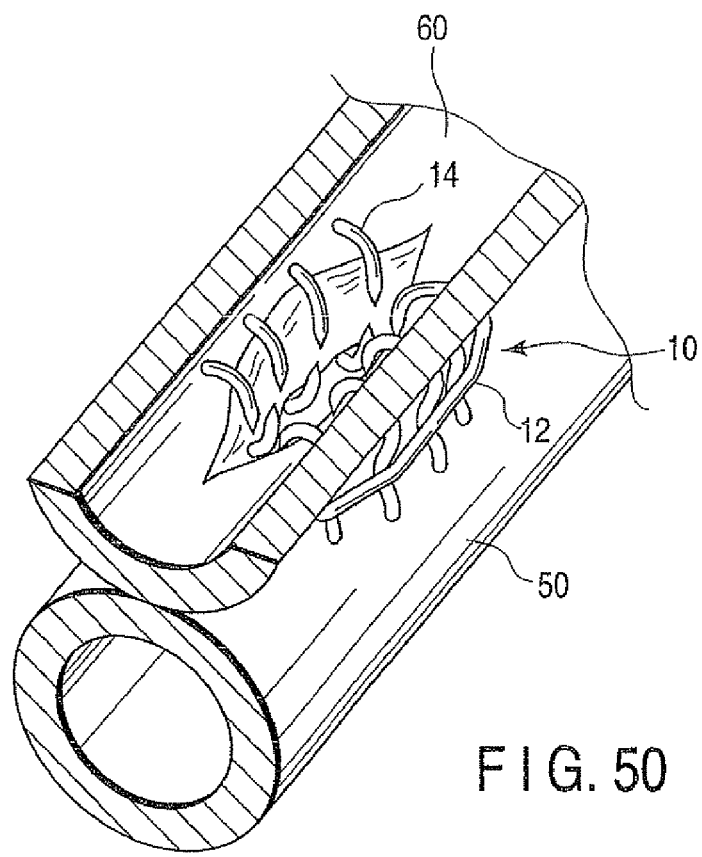
FIG. 50 is a perspective view showing the partially cutaway graft depicted in FIG. 49.
Figure 51:
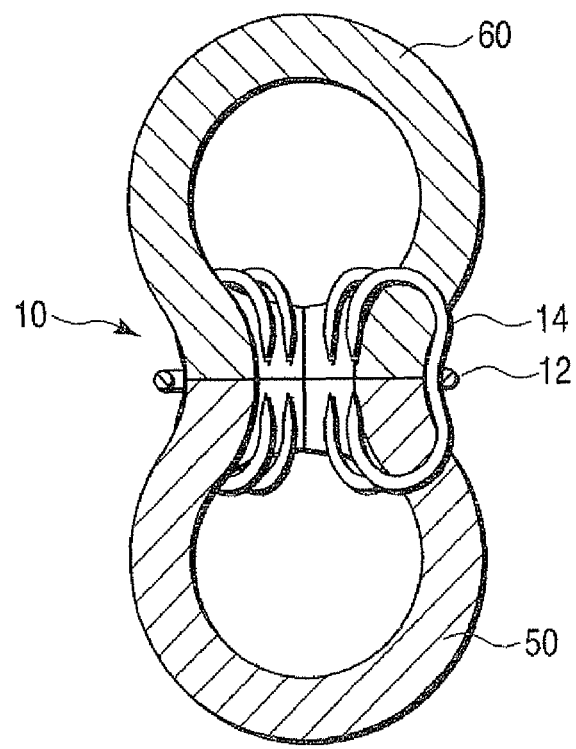
FIG. 51 is a cross-sectional view of the graft and the coronary artery that are inosculated to each other and shown in FIG. 49.

Thereafter, as shown in FIGS. 47 and 48, the staple holder 200, the coronary-artery supports 312, the graft supports 412, and others are removed from the staple 10 that has inosculated the coronary artery 50 and the graft 60 with each other. As a result, the staple 10 comes off the staple holder 200, so that the ring member 12 is restored to its original expanded shape. Consequently, an inosculated portion of the coronary artery 50 and the graft 60 widens outwardly, so that a flow path is assured between the coronary artery 50 and the graft 60. FIGS. 49 to 51 show the coronary artery 50 and the graft 60 that are inosculated to each other.

When piercing the coronary artery 50 or the graft with the staple pins 14 of the staple 10, it is preferable that the staple pins 14 of the staple 10 have penetrated through the coronary artery 50 or the graft 60 can be confirmed. Therefore, the treatment unit 102 further includes penetration detector to detect the staple pins 14 of the staple 10 that have penetrated through the coronary artery 50 or the graft 60.

Figure 52:
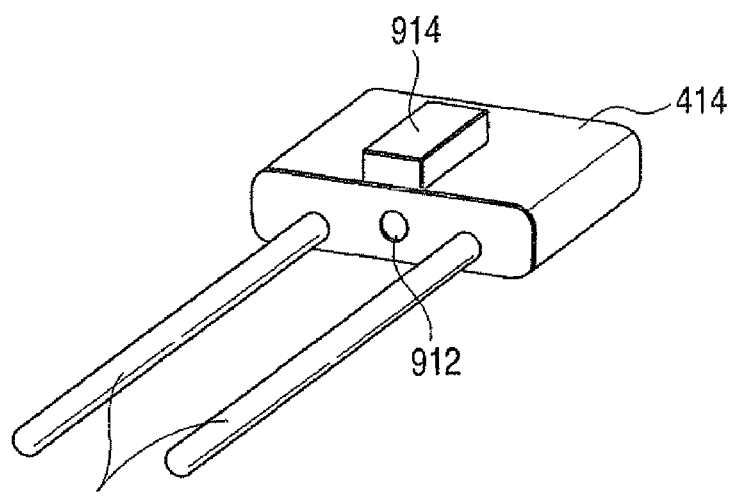
FIG. 52 shows a configuration to detect the staple pins of the staple that have penetrated through the graft.

The penetration detector to detect the staple pins 14 of the staple 10 that have penetrated through the graft 60 includes an LED 912 and an imaging camera 14 as shown in FIG. 52. The LED 912 illuminates the periphery of the graft supports 412. The imaging camera 914 images the periphery of the graft supports 412. The imaging camera 914 may be constituted by, but not limited to, a CCD camera, for example.

Figure 53:
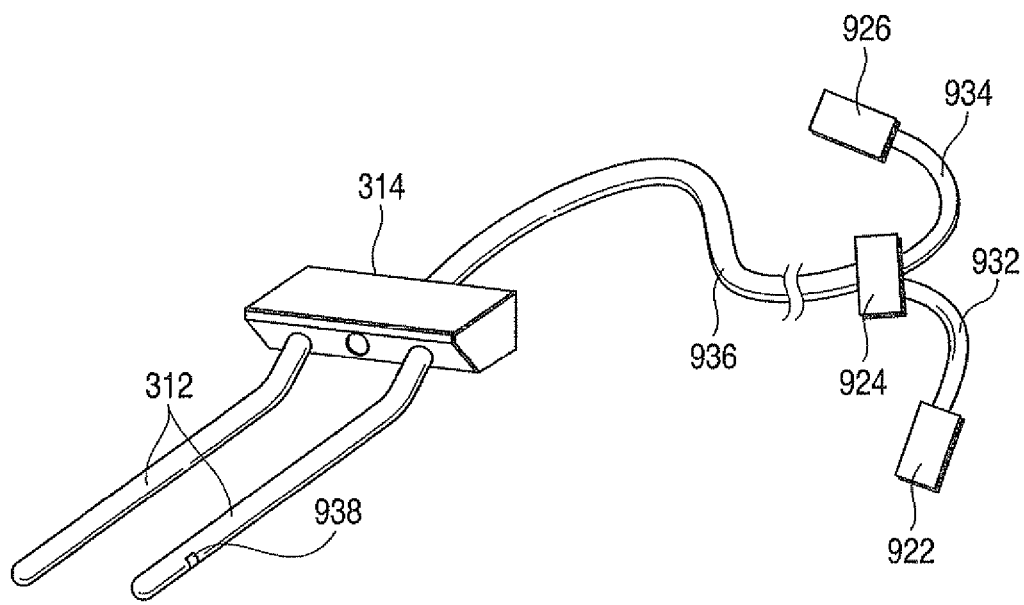
FIG. 53 shows a configuration to detect the staple pins of the staple that have penetrated through the coronary artery.

Further, the penetration detector to detect the staple pins 14 of the staple 10 that have penetrated through the coronary artery 50 includes a light source 922, an optical coupler 924, a CCD camera 926, a side-view lens 938, and a plurality of optical fibers 932, 934, and 936 as shown in FIG. 53.

The light source 922 is optically coupled with the optical coupler 924 through the optical fiber 932. The CCD camera 926 is optically coupled with the optical coupler 924 through the optical fiber 934. The optical coupler 924 is optically coupled with the side-view lens 938 through the optical fiber 936.

The light source 922 emits illumination light. The side-view lens 938 is provided on each coronary-artery support 312. The side-view lens 938 applies illumination light to a lateral side of the coronary-artery support 312 and takes reflected light from a physical body positioned on the lateral side of the coronary-artery support 312. The optical coupler 924 separates the reflected light took into the side-view lens 938 from the illumination light. The CCD camera 926 captures an optical image obtained from the reflected light.

The illumination light emitted from the light source 922 is sent to the side-view lens 938 through the optical fiber 932, the optical coupler 924, and the optical fiber 936 to be applied to the lateral side of the coronary-artery support 312 from the side-view lens 938. The illumination light applied from the side-view lens 938 is reflected by the physical body positioned on the lateral side of the coronary-artery support 312. Part of the reflected light enters the side-view lens 938. The reflected light that has entered the side-view lens 938 is sent to the CCD camera 926 through the optical fiber 936, the optical coupler 924, and the optical fiber 934 to be focused. The CCD camera 926 captures the formed image.

The image captured by each of the imaging camera 914 and the CCD camera 926 is displayed in a non-illustrated monitor. A user can confirm that the staple pins 14 of the staple 10 have penetrated through the coronary artery by observing the image displayed in the monitor.

This embodiment has the following advantages.

Since the blades 712 and 722 of the cutters 710 and 720 are arranged between the coronary artery 50 and the graft 60 to Incise the coronary artery 50 and the graft 60 from the outside, the hollow tissue inosculation apparatus 100 can be used for the narrow coronary artery 50 and graft 60.

Further, since the cutter 710 and the cutter 720 in the incision mechanism 700 can be independently operated in the upward-and-downward directions and the forward-and-backward directions, the coronary artery 50 and the graft 60 can be incised at positions that are equal to or different from each other for lengths that are equal to or different from each others. As a result, the coronary artery 50 and the graft 60 having different blood vessel wall thicknesses can be appropriately inosculated to each other.

Since the staple holder 200 holds the staple 10 in such a manner that the blades 712 and 722 of the cutters 710 and 720 do not come into contact with the staple 10, foreign particles can be prevented from being generated due to collision of the blades 712 and 722 of the cutters 710 and 720 and the staple 10. The foreign particles generated due to collision of the blades 712 and 722 of the cutters 710 and 720 and the staple 10 do not enter blood vessels.

Since the staple holder 200 prevents the ring member 12 of the staple 10 from being expanded, a load applied to the blood vessels when incising the coronary artery 50 and the graft 60 is small.

Since the coronary-artery supports 312 and the graft supports 412 deviate from the position where the staple pins 14 of the staple 10 penetrate through the coronary artery 50 and the graft 60, a load applied to the blood vessels when penetrating the staple pins 14 of the staple 10 through the coronary artery 50 and the graft 60 is small.

The section of the coronary artery 50 is brought into contact with the section of the graft 60 to inosculate the coronary artery 50 to the graft 60, and hence cell proliferation due to the self-reparative function hardly occurs, thereby reducing block of a blood flow owing to cell proliferation.

Observing the image captured by each of the imaging camera 914 and the CCD camera 926 enables confirming an inosculated state of the graft 60 and the coronary artery 50, e.g., a state that the staple pins 14 of the staple 10 have penetrated through the coronary artery 50 or that inosculation of the graft 60 and the coronary artery 50 is finished.

[Modification of Stapler]

Figure 54:
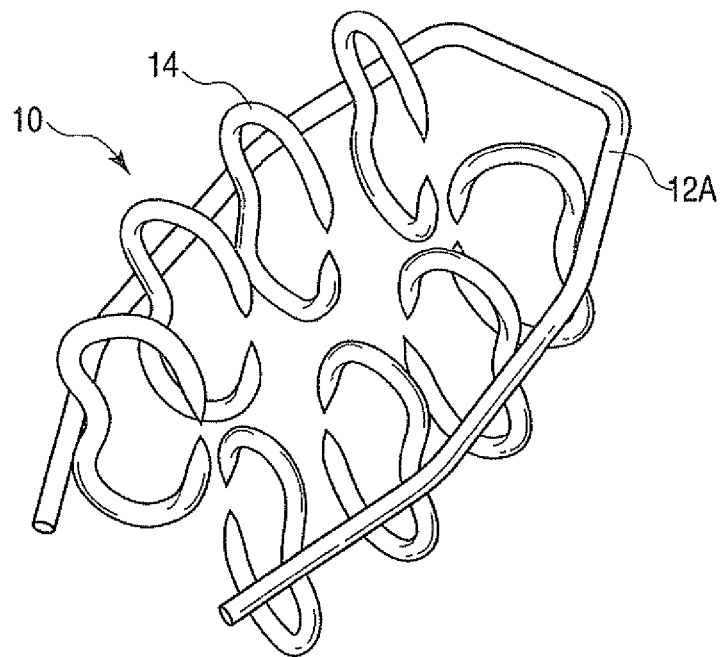
FIG. 54 shows another staple that can be used in place of the staple depicted in FIGS. 1 and 2.

A modification of the staple will now be described. In the above-described embodiment, the ring member 12 in the staple 10 has a closed ring-like shape, but the shape of the ring member 12 is not restricted thereto. As a modification of the staple 10, FIG. 54 shows another staple 10A that can be used in place of the staple 10 depicted in FIGS. 1 and 2. As shown in FIG. 54, in a staple 10A according to this modification, a ring member 12A has an opened ring-like shape. Other structures are the same as those of the staple 10 depicted in FIGS. 1 and 2. This staple 10A is used in the hollow tissue inosculation apparatus 100 in completely the same manner as the staple 10 depicted in FIGS. 1 and 2.

Second Embodiment

This embodiment is different from the first embodiment in disposing positions of coronary-artery supports 312 and graft supports 412 with respect to a fixing portion 314 and a fixing portion 414 and penetration detector to detect staple pins 14 of a staple 10 that have penetrated through a coronary artery 50 or a graft 60, but any other structures are basically the same.

In this embodiment, as shown in FIG. 55, for example, contact positions of the coronary-artery supports 312 and the graft supports 412 with the coronary artery 50 and the graft 60 are positioned on an outer side of positions that the staple pins 14 of the staple 10 penetrate through the coronary artery 50 and the graft 60.

An operation of inosculating the coronary artery with the graft with the staple 10 by using a hollow tissue inosculation apparatus according to this embodiment will now be described hereinafter with reference to FIGS. 55 to 65.

First, like the first embodiment, the staple 10 is attached to a staple holder 200. Then, outer pillars 512, inner pillars 532, outer pillars 612, and inner pillars 632 are moved away from the staple holder 200 to straighten the staple pins 14 of the staple 10. Subsequently, the coronary-artery supports 312 are stuck into the coronary artery 50 and a coronary-artery support mechanism 300 is then closed. Furthermore, the graft supports 412 and the fixing portion 414 are inserted into the graft 60 and fix the graft 60, and a graft support mechanism 400 is then closed. FIG. 55 shows this state.

Then, as shown in FIG. 56, the graft support mechanism 400 and the staple holder 200 are moved closer to the coronary-artery support mechanism 300 to narrow gaps of the graft support mechanism 400 and the coronary-artery support mechanism 300 with respect to the staple holder 200, so that end portions of the staple pins 14 of the staple 10 are stuck into the coronary artery 50 and the graft 60. The coronary-artery supports 312 and the graft supports 412 respectively support the coronary artery 50 and the graft 60 when the staple pins 14 of the staple 10 are stuck into the coronary artery 50 and the graft 60. Stick of the staple pins 14 is moderately performed so that the staple pins 14 do not penetrate through the coronary artery 50 and the graft 60.

Figure 57:
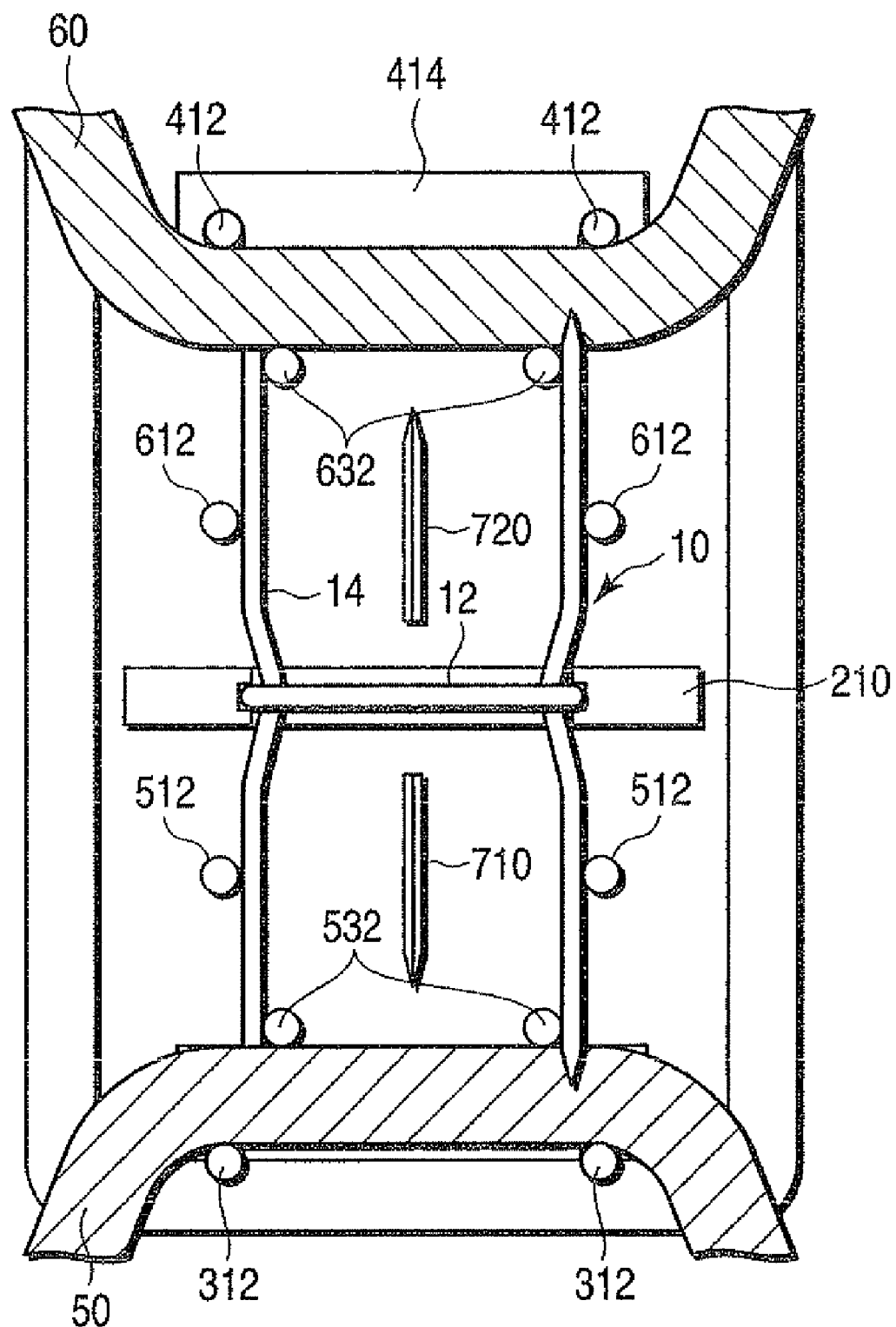
FIG. 57 is a front view of the treatment unit in which blades of cutters are arranged between the graft and the coronary artery.

Thereafter, as shown in FIG. 57, cutters 710 and 720 of an incision mechanism 700 are moved in the forward direction to arrange blades 712 and 722 on a rear side in a ring member 12 of the staple 10.

Figure 58:
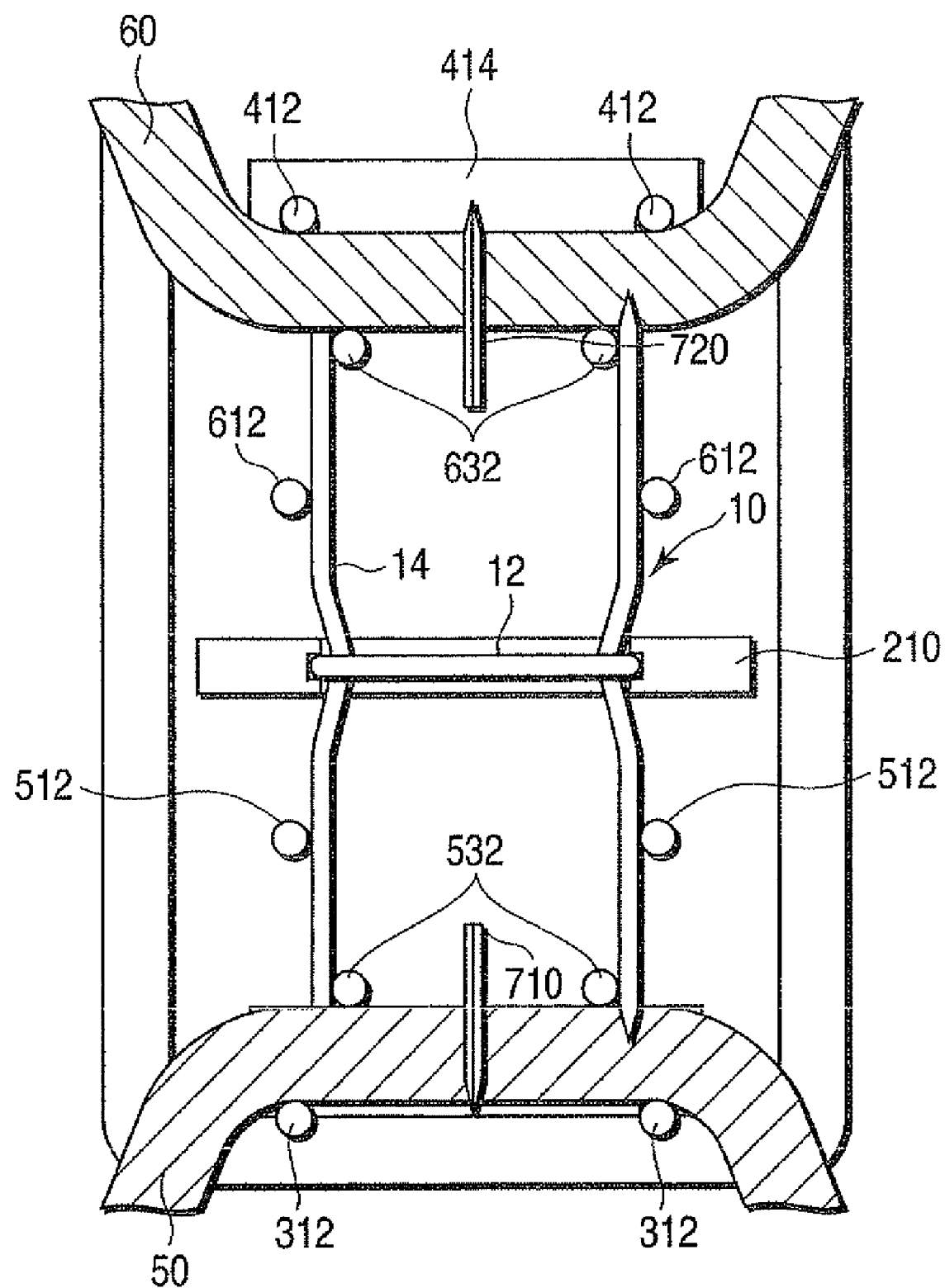
FIG. 58 is a front view of the treatment unit in which incision of the graft and the coronary artery is finished.

Subsequently, as shown in FIG. 58, the cutter 710 is moved in the downward direction to stick the blade 712 into the coronary artery 50, the cutter 720 is moved in the upward to stick the blade 722 into the graft 60, and then both the cutter 710 and the cutter 720 are moved in the forward direction to incise the coronary artery 50 and the graft 60, respectively.

Figure 59:
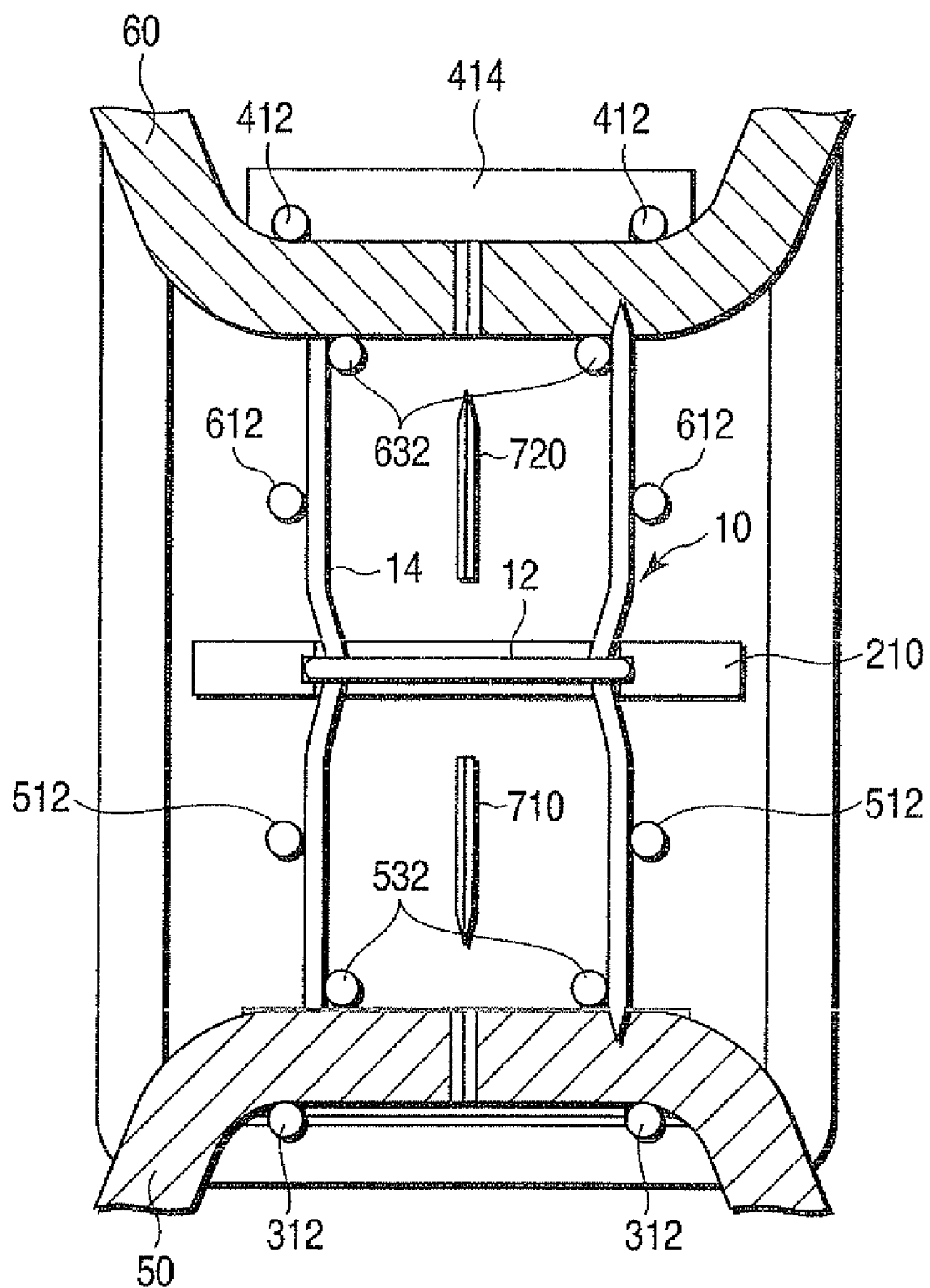
FIG. 59 is a front view of the treatment unit while the cutters are retracted into a housing.

Then, as shown in FIG. 59, the cutter 710 is moved in the upward direction to pull out the blade 712 from the coronary artery 50, the cutter 720 is moved in the downward direction to pull out the blade 722 from the graft 60, and then both the cutters 710 and 720 are moved in the backward direction to be retracted into a housing 190.

Figure 60:
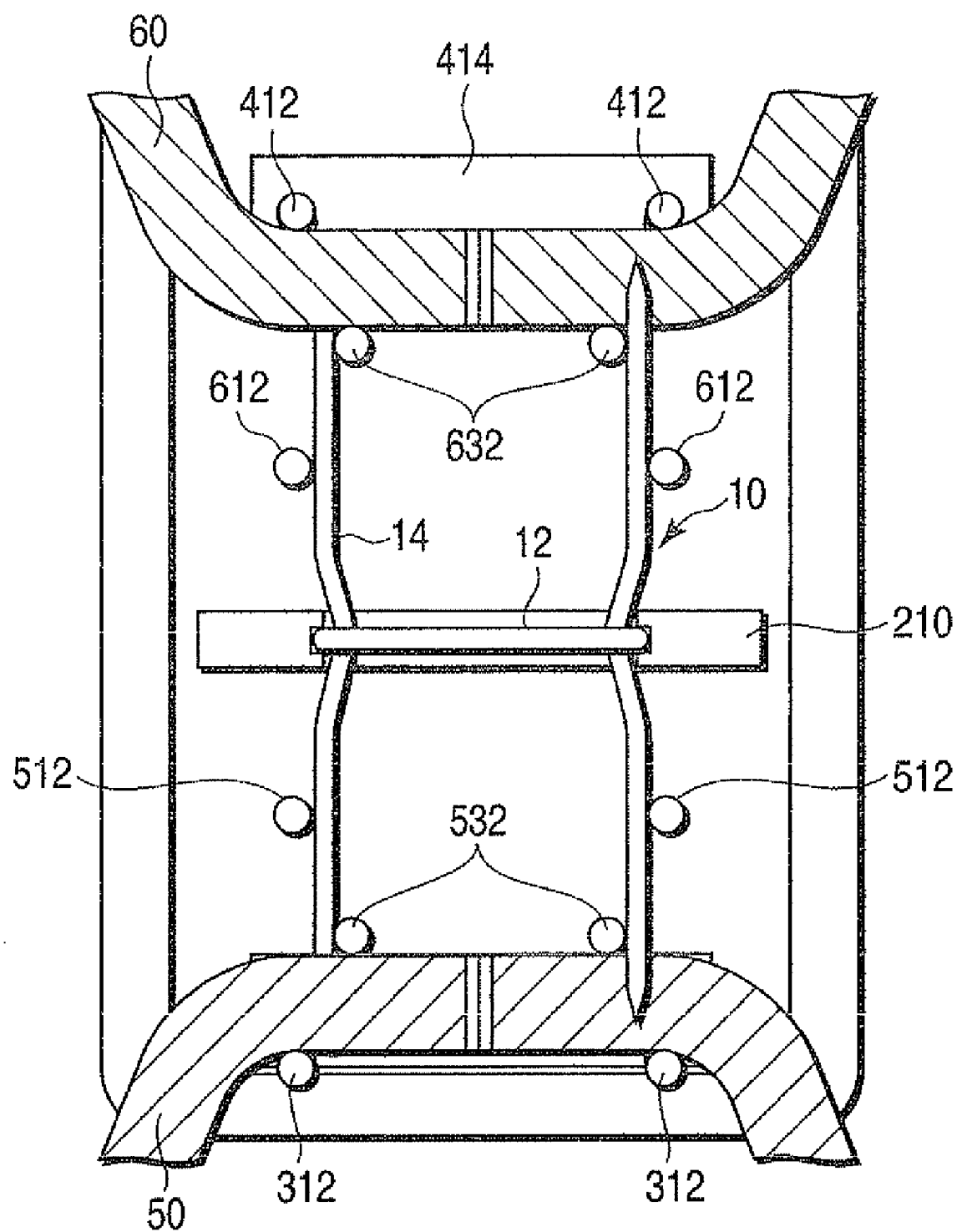
FIG. 60 is a front view of the treatment unit in which the staple pins of the staple are further stuck into the graft and the coronary artery.

Thereafter, as shown in FIG. 60, the graft support mechanism 400 and the staple holder 200 are further moved closer to the coronary artery support mechanism 300 to narrow the gaps of the graft support mechanism 400 and the coronary-artery support mechanism 300 with respect to the staple holder 200. At this time, the inner pillars 632 and the inner pillars 532 move closer to the staple holder 200 in cooperation with the graft support mechanism 400 and the coronary-artery support mechanism 300, but both the outer pillars 612 and the outer pillars 512 do not move with respect to the staple holder 200. The graft support mechanism 400 and the coronary-artery support mechanism 300 are moved closer to the staple holder 200 in this manner, causing the end portions of the staple pins 14 of the staple 10 to penetrate through the coronary artery 50 and the graft 60, respectively.

The end portions of the staple pins 14 that have stuck into the coronary artery 50 or the graft 60 are to be restored to a bent shape as a natural state. Since the coronary-artery supports 312 and the graft supports 412 are positioned on the outer side of the end portions of the staple pins 14 that have penetrated through the coronary artery 50 or the graft 60, they do not obstruct the deformation of the end portions of the staple pins 14 that are restored to the original bent shape. Consequently, as shown in FIG. 61, the end portions of the staple pins 14 of the staple 10 penetrate through the coronary artery 50 and the graft 60 while being restored to the bent shape.

Subsequently, as shown in FIG. 62, the graft support mechanism 400 and the staple holder 200 are moved closer to the coronary-artery support mechanism 300 to narrow gaps of the outer pillars 512 and the inner pillars 532 with respect to the staple holder 200 and gaps of the outer pillars 612 and the inner pillars 632 with respect to the staple holder 200. As a result, the staple pins 14 are substantially restored to the original bent shape.

Figure 63:
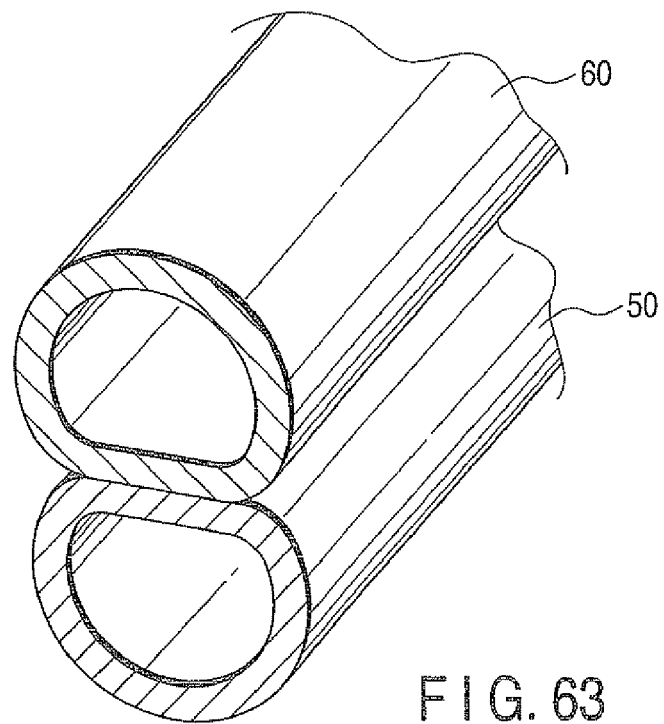
FIG. 63 is a perspective view of the graft and the coronary artery inosculated to each other.
Figure 64:
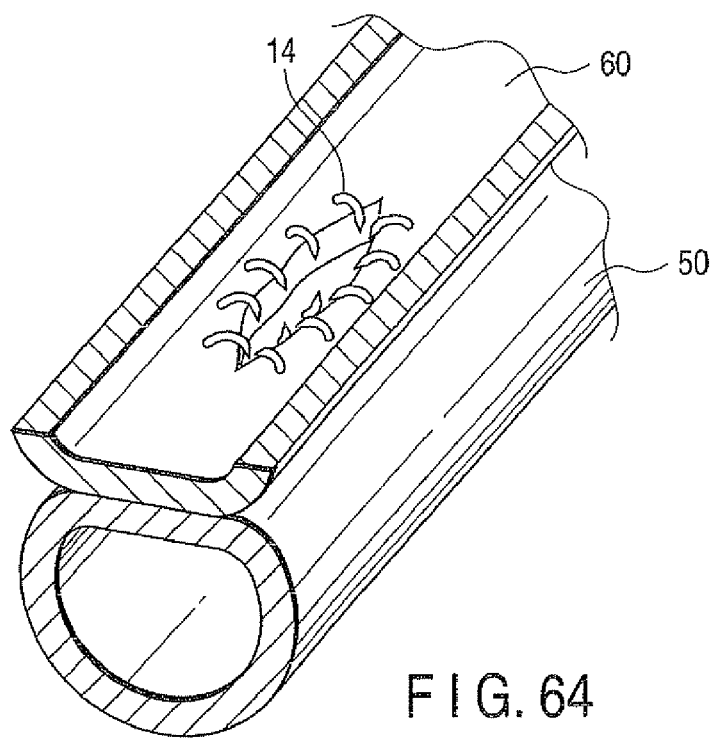
FIG. 64 is a perspective view showing the partially cutaway graft depicted in FIG. 63.

Thereafter, the staple holder 200, the coronary-artery supports 312, the graft supports 412, and others are removed from the staple 10 that has inosculated the coronary artery 50 and the graft 60 with each other. As a result, the staple 10 comes off the staple holder 200, so that the ring member 12 is restored to its original expanded shape. Consequently, an inosculated portion of the coronary artery 50 and the graft widens outwardly, so that a flow path is assured between the coronary artery 50 and the graft 60. FIGS. 63 to 65 show the coronary artery 50 and the graft 60 inosculated with each other. In this embodiment, as shown in FIGS. 63 to 65, the coronary artery 50 and the graft 60 are inosculated with each other with their side surfaces being in contact with each other.

Figure 67:
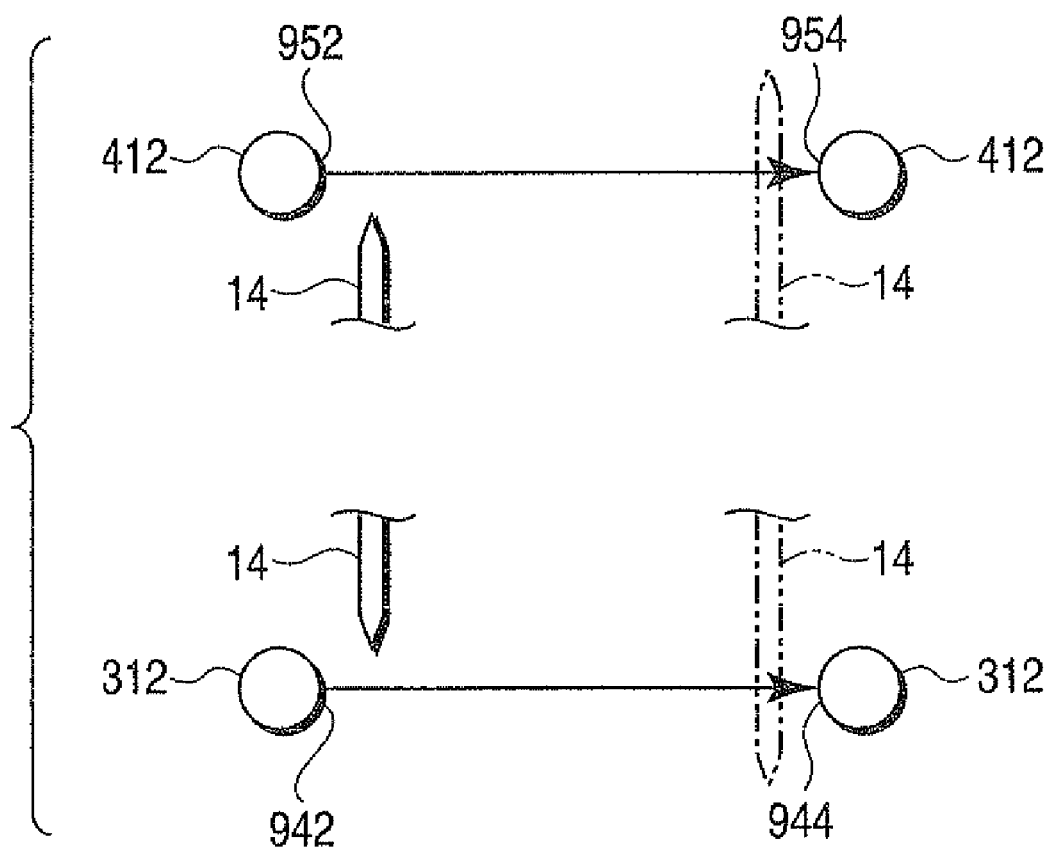
FIG. 67 schematically shows a positional relationship of the staple pins of the staple with respect to the coronary-artery supports and the graft supports depicted in FIG. 66.

In this embodiment, as shown in FIGS. 66 and 67, penetration detector to detect the staple pins 14 of the staple 10 that have penetrated through the coronary artery 50 includes an optical sensor constituted by a light emitting element 942 provided on one on the coronary-artery supports 312 and a light receiving element 944 provided on the other of the coronary-artery supports 312. The light emitting element 942 and the light receiving element 944 are arranged on the inner sides of the coronary-artery supports 312 so as to face each other. The light emitting element 942 emits light toward the light receiving element 944. The light receiving element 944 detects an intensity of the received light, i.e., incident light.

Moreover, penetration detector to detect the staple pins 14 of the staple 10 that have penetrated through the graft 60 includes an optical sensor constituted by a light emitting element 952 provided on one of the graft supports 412 and a light receiving element 954 provided on the other of the graft supports 412. The light emitting element 952 and the light receiving element 954 are arranged on the inner sides of the graft supports 412 so as to face each other. The light emitting element 952 emits light toward the light receiving element 954. The light receiving element 954 detects an intensity of the received light, i.e., incident light.

The staple pins 14 of the staple 10 that have penetrated through the coronary artery 50 are detected as follows.

As can be understood from FIG. 67, in a state where the staple pins 14 of the staple 10 have not penetrated through the coronary artery 50, the light emitted from the light emitting element 942 enters the light receiving element 944 without being blocked by the staple pins 14 (indicated by a solid line). On the other hand, in a state where the staple pins 14 of the staple 10 have penetrated through the coronary artery 50, part of the light emitted from the light emitting element 942 is blocked by the staple pins 14 (indicated by a phantom line), and remaining part enters the light receiving element 944. Therefore, the intensity of the incident light detected by the light receiving element 944 in the state where the staple pins 14 have not penetrated through the coronary artery 50 is higher than the intensity of the incident light detected by the light receiving element 944 in the state where the staple pins 14 have penetrated through the coronary artery 50.

With an appropriate value between the intensity of the incident light detected by the light receiving element 944 in the state where the staple pins 14 have not penetrated through the coronary artery 50 and the intensity of the incident light detected by the light receiving element 944 in the state where the staple pins 14 have penetrated through the coronary artery 50 being set to a threshold value in advance, the intensity of the incident light detected by the light receiving element 944 is compared with the threshold value. It is determined that the staple pins 14 have not penetrated through the coronary artery 50 if the intensity of the incident light detected by the light receiving element 944 is smaller than the threshold value and, on the other hand, it is determined that the staple pins 14 have penetrated through the coronary artery 50 if the intensity of the incident light detected by the light receiving element 944 is larger than the threshold value.

The detection of the staple pins 14 of the staple 10 that have penetrated through the graft 60 is carried out by the same manner using a light emitting element 952 and a light receiving element 954.

As described above, in this embodiment, comparing the light intensity detected by the light emitting element 944 and the light receiving element 954 with the threshold value enables confirming that the staple pins 14 of the staple 10 have penetrated through the graft 60 and the coronary artery 50.

Although the embodiment according to the present invention has been described with reference to the accompanying drawings, the present invention is not restricted thereto, and various modifications or changes can be carried out without departing from the scope of the invention.

The mechanism to move the staple holder 200, the graft support mechanism 400, the outer pillars 512, the inner pillars 532, the outer pillars 612, and the inner pillars 632 in the upward-and-downward directions is formed of the groove cam mechanism in the foregoing embodiment, but the present invention is not restricted thereto. This mechanism may be constituted of a mechanism that utilizes a translation link, an oscillation link, screws, gears, and others. Likewise, the mechanism to move the cutters 710 and 720 is not restricted to the groove cam mechanism, and it may be constituted of a mechanism that utilizes a translation link, an oscillation link, screws, gears, and others. These mechanisms are operated by the wires in the embodiment, but the present invention is not restricted thereto, and the mechanisms may be operated by an arbitrary force transmission member such as a multi-node link. In place of using the force transmission member, an actuator may be provided to these mechanisms and used to operate them.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A hollow tissue inosculation apparatus to inosculate two hollow tissues to each other with a staple having a plurality of elastically deformable bent staple pins, comprising:
 a staple holder to hold the staple;
 a curvature control mechanism to control curvature of the staple pins of the staple held in the staple holder, the curvature control mechanism substantially straightening the staple pins; and
 a gap control mechanism to control gaps of the hollow tissues with respect to the staple holder, the gap control mechanism reducing the gaps to cause the substantially straightened staple pins to penetrate through the hollow tissues; and
 a detector to detect the staple pins of the staple that have penetrated through the hollow tissue.

2. The apparatus according to claim 1, wherein the detector includes an imager.

3. The apparatus according to claim 1, wherein the detector includes an optical sensor.

4. The apparatus according to claim 1, further comprising an incision mechanism to incise the hollow tissues.

* * * * *